(12) United States Patent
Kjeldsen et al.

(10) Patent No.: US 6,521,738 B2
(45) Date of Patent: Feb. 18, 2003

(54) METHOD FOR MAKING INSULIN PRECURSORS AND INSULIN PRECURSOR ANALOGS

(75) Inventors: Thomas Borglum Kjeldsen, Virum (DK); Svend Ludvigsen, Lynge (DK); Niels C. Kaarsholm, Vanlose (DK)

(73) Assignee: Novo Nordisk A/S, Bagsvaerd (DK)

( * ) Notice: Subject to any disclaimer, the term of this patent is extended or adjusted under 35 U.S.C. 154(b) by 64 days.

(21) Appl. No.: 09/736,611

(22) Filed: Dec. 14, 2000

(65) Prior Publication Data

US 2001/0023069 A1 Sep. 20, 2001

Related U.S. Application Data

(60) Provisional application No. 60/181,443, filed on Feb. 10, 2000, and provisional application No. 60/211,441, filed on Jun. 13, 2000.

(30) Foreign Application Priority Data

Dec. 29, 1999 (DK) ........................................ 1999 01868
Mar. 17, 2000 (DK) ........................................ 2000 00440

(51) Int. Cl.[7] ........................ C07K 14/62; C12N 15/17; C12N 1/15; C12N 1/21
(52) U.S. Cl. .................... 530/303; 435/69.1; 435/69.7; 435/320.1; 435/325; 435/252.3; 435/254.2; 435/254.21; 536/23.4; 536/23.5
(58) Field of Search .................... 530/303; 435/69.1, 435/69.7, 320.1, 252.3, 254.2, 254.21, 325; 536/23.4, 23.5

(56) References Cited

U.S. PATENT DOCUMENTS 5,962,267 A  10/1999  Shin et al. .................. 435/69.4

FOREIGN PATENT DOCUMENTS

EP          0 163 529        12/1985
WO         WO 95/16708       6/1995

OTHER PUBLICATIONS

Howey et al. Diabetes 43:396–402, 1994, abstract only cited.*

Pfeffer et al., Ann. Rev. Biochem., vol. 56, pp. 829–852 (1987).

Frank et al., Rich & Gross, pp. 729–739 (1981).

Chan et al., Proc. Natl, Acad. Sci, vol. 78. No. 9, pp. 5401–5405 (1981).

Thim et al., Proc. Natl, Acad. Sci, vol. 83, pp. 6766–6670 (1986).

Johnson, Ann. Rev. Biophys. Chem, vol. 17, pp. 145–166 (1988).

Pace, CRC Critical Reviews in Biochemistry, vol. 3, pp. 1–43 (1975).

Seung–Gu Chang et al., Biochemical Journal, vol. 329, pp. 631–635 (1998).

* cited by examiner

*Primary Examiner*—Mary E. Mosher
(74) *Attorney, Agent, or Firm*—Reza Green

(57) ABSTRACT

Novel insulin precursors and insulin precursor analogs having a mini C-peptide comprising at least one aromatic amino acid residue have an increased folding stability. The novel insulin precursors and insulin precursor analogs can be expressed in yeast in high yields and are preferably not more 15 amino acid residues in length. Also provided are polynucleotide sequences encoding the claimed precursors or precursor analogs, and vectors and cell lines containing such polynucleotide sequences.

40 Claims, 9 Drawing Sheets

```
                              EcoRI     BglII
                              ~~~~~~~   ~~~~~   -
 901  TCTTGCTTAA ATCTATAACT ACAAAAAACA CATACAGGAA TTCCATTCAA
      AGAACGAATT TAGATATTGA TGTTTTTTGT GTATGTCCTT AAGGTAAGTT

BglII
      ~~~~~
 951  GATCTGTTCA AACAAGAAGA TTACAAACTA TCAATTTCAT ACACAATATA
      CTAGACAAGT TTGTTCTTCT AATGTTTGAT AGTTAAAGTA TGTGTTATAT

+3                 M   R   F   P   S   I   F   T   A   V   L   F
                                                    PstI
                                                    ~~~~~~~
1001  AACGATTAAA AGAATGAGAT TTCCTTCAAT TTTTACTGCA GTTTTATTCG
      TTGCTAATTT TCTTACTCTA AAGGAAGTTA AAAATGACGT CAAAATAAGC

+3  A   A   S   A   L   A   A   P   V   N   T   T   T     E   D   E
1051  CAGCATCCTC CGCATTAGCT GCTCCAGTCA ACACTACAAC AGAAGATGAA
      GTCGTAGGAG GCGTAATCGA CGAGGTCAGT TGTGATGTTG TCTTCTACTT

+3  T   A   Q   I   P   A   E   A   V   I   G   Y   S   D   L   E   G
1101  ACGGCACAAA TTCCGGCTGA AGCTGTCATC GGTTACTCAG ATTTAGAAGG
      TGCCGTGTTT AAGGCCGACT TCGACAGTAG CCAATGAGTC TAAATCTTCC

+3   D   F   D   V   A   V   L   P   F   S   N   S   T   N   N   G
1151  GGATTTCGAT GTTGCTGTTT TGCCATTTTC AACAGCACA  AATAACGGGT
      CCTAAAGCTA CAACGACAAA ACGGTAAAAG GTTGTCGTGT TTATTGCCCA

+3  L   L   F   I   N   T   T   I   A   S   I   A   A   K   E   E   G
1201  TATTGTTTAT AAATACTACT ATTGCCAGCA TTGCTGCTAA AGAAGAAGGG
      ATAACAAATA TTTATGATGA TAACGGTCGT AACGACGATT TCTTCTTCCC

+3   V   S   M   A   K   R   E   E   A   E   A   E   A   P   K   F   V
           NcoI                                                    HpaI
           ~~~~~~                                                  ~~
1251  GTATCCATGG CTAAGAGAGA AGAAGCTGAA GCTGAAGCTC CAAAGTTCGT
      CATAGGTACC GATTCTCTCT TCTTCGACTT CGACTTCGAG GTTTCAAGCA

+3   N   Q   H   L   C   G   S   H   L   V    E   A   L   Y   L   V
      HpaI                                                 HindIII
      ~~~~                                                 ~~~~~~~
1301  TAACCAACAC TTGTGTGGTT CTCACTTGGT TGAAGCTTTG TACTTGGTTT
      ATTGGTTGTG AACACACCAA GAGTGAACCA ACTTCGAAAC ATGAACCAAA +3  C   G   E   R   G   F   F   Y   T   D   K   G   I   V   E   Q   C
1351  GTGGTGAAAG AGGTTTCTTC TACACTGACA AGGGTATCGT TGAACAATGT
      CACCACTTTC TCCAAAGAAG ATGTGACTGT TCCCATAGCA ACTTGTTACA +3  C   T   S   I   C   S   L   Y   Q   L   E   N   Y   C   N   *
1401  TGTACTTCTA TCTGTTCTTT GTACCAATTG GAAAACTACT GTAACTAGAC
      ACATGAAGAT AGACAAGAAA CATGGTTAAC CTTTTGATGA CATTGATCTG XbaI
              ~~~~~~
1451  GCAGCCCGCA GGCTCTAGAA ACTAAGATTA ATATAATTAT ATAAAAATAT
      CGTCGGGCGT CCGAGATCTT TGATTCTAAT TATATTAATA TATTTTTATA
```

Fig. 2

```
                                                          EcoRI    BglII
                                                         ~~~~~~~    ~
 901  TCTTGCTTAA ATCTATAACT ACAAAAAACA CATACAGGAA TTCCATTCAA
      AGAACGAATT TAGATATTGA TGTTTTTTGT GTATGTCCTT AAGGTAAGTT
       BglII
      ~~~~~
 951  GATCTGTTCA AACAAGAAGA TTACAAACTA TCAATTTCAT ACACAATATA
      CTAGACAAGT TTGTTCTTCT AATGTTTGAT AGTTAAAGTA TGTGTTATAT
   +3             M  R  F   P  S  I   F  T  A    V  L  F
                                              PstI
                                             ~~~~~~~
1001  AACGATTAAA AGAATGAGAT TTCCTTCAAT TTTTACTGCA GTTTTATTCG
      TTGCTAATTT TCTTACTCTA AAGGAAGTTA AAAATGACGT CAAAATAAGC

+3  A  A  S  S    A  L  A    A  P  V  N    T  T  T    E  D  E
1051  CAGCATCCTC CGCATTAGCT GCTCCAGTCA ACACTACAAC AGAAGATGAA
      GTCGTAGGAG GCGTAATCGA CGAGGTCAGT TGTGATGTTG TCTTCTACTT

+3  T  A  Q    I  P  A  E    A  V  I    G  Y  S    D  L  E  G
1101  ACGGCACAAA TTCCGGCTGA AGCTGTCATC GGTTACTCAG ATTTAGAAGG
      TGCCGTGTTT AAGGCCGACT TCGACAGTAG CCAATGAGTC TAAATCTTCC

+3  D  F  D    V  A  V  L    P  F  S    N  S  T    N  N  G
1151  GGATTTCGAT GTTGCTGTTT TGCCATTTTC CAACAGCACA AATAACGGGT
      CCTAAAGCTA CAACGACAAA ACGGTAAAAG GTTGTCGTGT TTATTGCCCA

+3  L  L  F  I    N  T  T    I  A  S  I    A  A  K    E  E  G
1201  TATTGTTTAT AAATACTACT ATTGCCAGCA TTGCTGCTAA AGAAGAAGGG
      ATAACAAATA TTTATGATGA TAACGGTCGT AACGACGATT TCTTCTTCCC

+3  V  S  M  A    K  R  E    E  A  E    A  E  A  P    K  F  V
            NcoI                                              HpaI
          ~~~~~~                                               ~~
1251  GTATCCATGG CTAAGAGAGA AGAAGCTGAA GCTGAAGCTC CAAAGTTCGT
      CATAGGTACC GATTCTCTCT TCTTCGACTT CGACTTCGAG GTTTCAAGCA

+3  N  Q  H    L  C  G  S    H  L  V    E  A  L    Y  L  V
      HpaI                                  HindIII
      ~~~~                                  ~~~~~~~
1301  TAACCAACAC TTGTGTGGTT CTCACTTGGT TGAAGCTTTG TACTTGGTTT
      ATTGGTTGTG AACACACCAA GAGTGAACCA ACTTCGAAAC ATGAACCAAA +3  C  G  E  R    G  F  F    Y  T  D  K   E  W  K   G  I  V
1351  GTGGTGAAAG AGGTTTCTTC TACACTGACA AGGAGTGGAA GGGTATCGTT
      CACCACTTTC TCCAAAGAAG ATGTGACTGT TCCTCACCTT CCCATAGCAA +3  E  Q  C  C    T  S  I    C  S  L    Y  Q  L  E    N  Y  C
1401  GAACAATGTT GTACTTCTAT CTGTTCTTTG TACCAATTGG AAAACTACTG
      CTTGTTACAA CATGAAGATA GACAAGAAAC ATGGTTAACC TTTTGATGAC +3  N  *
                                     XbaI
                                    ~~~~~~
1451  TAACTAGACG CAGCCCGCAG GCTCTAGAAA CTAAGATTAA TATAATTATA
      ATTGATCTGC GTCGGGCGTC CGAGATCTTT GATTCTAATT ATATTAATAT
                              Fig. 3
```

```
 901 TTCTTGCTTA AATCTATAAC TACAAAAAAC ACATACAGGA ATTCCATTCA
     AAGAACGAAT TTAGATATTG ATGTTTTTTG TGTATGTCCT TAAGGTAAGT

951 AGAATAGTTC AAACAAGAAG ATTACAAACT ATCAATTTCA TACACAATAT
     TCTTATCAAG TTTGTTCTTC TAATGTTTGA TAGTTAAAGT ATGTGTTATA

+1                  M  K  L  K  T  V  R  S  A  V  L  S
                                          BglII
                                          ~~~~~~
1001 AAACGATTAA AAGAATGAAA CTGAAAACTG TAAGATCTGC GGTCCTTTCG
     TTTGCTAATT TTCTTACTTT GACTTTTGAC ATTCTAGACG CCAGGAAAGC

+1  S  L  F  A  S  Q  V  L  G  Q  P  I  D  D  T  E  S
                            MscI
                            ~~~~
1051 TCACTCTTTG CATCTCAGGT CCTTGGCCAA CCAATTGACG ACACTGAATC
     AGTGAGAAAC GTAGAGTCCA GGAACCGGTT GGTTAACTGC TGTGACTTAG

+1   N  T  T  S  V  N  L  M  A  D  D  T  E  S  R  F
                                              XbaI
                                              ~~~~~~
1101 TAACACTACT TCTGTCAACT TGATGGCTGA CGACACTGAA TCTAGATTCG
     ATTGTGATGA AGACAGTTGA ACTACCGACT GCTGTGACTT AGATCTAAGC

+1 A  T  N  T  T  L  A  G  G  L  D  V  V  N  L  I  S
                                        HpaI      NcoI
                                        ~~~~~~~   ~~
1151 CTACTAACAC TACTTTGGCT GGTGGTTTGG ATGTTGTTAA CTTGATCTCC
     GATGATTGTG ATGAAACCGA CCACCAAACC TACAACAATT GAACTAGAGG

+1  M  A  K  R  E  E  G  E  P  K  F  V  N  Q  H  L  C
      NcoI                             HpaI
      ~~~~                             ~~~~~~
1201 ATGGCTAAGA GAGAAGAAGG TGAACCAAAG TTCGTTAACC AACACTTGTG
     TACCGATTCT CTCTTCTTCC ACTTGGTTTC AAGCAATTGG TTGTGAACAC

+1  G  S  H  L  V  E  A  L  Y  L  V  C  G  E  R  G
                  HindIII
                  ~~~~~~~
1251 TGGTTCCCAC TTGGTTGAAG CTTTGTACTT GGTTTGTGGT GAAAGAGGTT
     ACCAAGGGTG AACCAACTTC GAAACATGAA CCAAACACCA CTTTCTCCAA +1 F  F  Y  T  D  K  E  W  K  G  I  V  E  Q  C  C  T
1301 TCTTCTACAC TGACAAGGAA TGGAAGGGTA TCGTTGAACA ATGTTGTACT
     AGAAGATGTG ACTGTTCCTT ACCTTCCCAT AGCAACTTGT TACAACATGA +1  S  I  C  S  L  Y  Q  L  E  N  Y  C  N  *
1351 TCTATCTGTT CTTTGTACCA ATTGGAAAAC TACTGTAACT AGACGCAGCC
     AGATAGACAA GAAACATGGT TAACCTTTTG ATGACATTGA TCTGCGTCGG XbaI
         ~~~~~~~
1401 CGCAGGCTCT AGAAACTAAG ATTAATATAA TTATATAAAA ATATTATCTT
     GCGTCCGAGA TCTTTGATTC TAATTATATT AATATATTTT TATAATAGAA
```

Fig. 8

```
 901  TTCTTGCTTA AATCTATAAC TACAAAAAAC ACATACAGGA ATTCCATTCA
      AAGAACGAAT TTAGATATTG ATGTTTTTTG TGTATGTCCT TAAGGTAAGT

951  AGAATAGTTC AAACAAGAAG ATTACAAACT ATCAATTTCA TACACAATAT
      TCTTATCAAG TTTGTTCTTC TAATGTTTGA TAGTTAAAGT ATGTGTTATA

+1                   M   K   L   K   T   R   S   A   V   L   S
                                               BglII
                                               ~~~~~~
1001  AAACGATTAA AAGAATGAAA CTGAAAACTG TAAGATCTGC GGTCCTTTCG
      TTTGCTAATT TTCTTACTTT GACTTTTGAC ATTCTAGACG CCAGGAAAGC

+1   S   L   F   A   S   Q   V   L   G   Q   P   I   D   D   T   E   S
                                       MscI
                                       ~~~~~~
1051  TCACTCTTTG CATCTCAGGT CCTTGGCCAA CCAATTGACG ACACTGAATC
      AGTGAGAAAC GTAGAGTCCA GGAACCGGTT GGTTAACTGC TGTGACTTAG

+1   Q   T   T   S   V   N   L   M   A   D   D   T   E   S   A   F
1101  TCAAACTACT TCTGTCAACT TGATGGCTGA CGACACTGAA TCTGCTTTCG
      AGTTTGATGA AGACAGTTGA ACTACCGACT GCTGTGACTT AGACGAAAGC

+1  A   T   Q   T   N   S   G   L   D   V   V   G   L   I   S   M
                                                                   NcoI
                                                                   ~~~~~
1151  CTACTCAAAC TAACTCTGGT GGTTTGGATG TTGTTGGTTT GATCTCCATG
      GATGAGTTTG ATTGAGACCA CCAAACCTAC AACAACCAAA CTAGAGGTAC

+1   A   K   R   E   G   E   P   K   F   V   N   Q   H   L   C   G
       NcoI                                 HpaI
       ~                                    ~~~~~~
1201  GCTAAGAGAG AAGAAGGTGA ACCAAAGTTC GTTAACCAAC ACTTGTGCGG
      CGATTCTCTC TTCTTCCACT TGGTTTCAAG CAATTGGTTG TGAACACGCC

+1   S   H   L   V   E   A   L   Y   L   V   C   G   E   R   G   F
                   HindIII
                   ~~~~~~
1251  TTCCCACTTG GTTGAAGCTT TGTACTTGGT TTGCGGTGAA AGAGGTTTCT
      AAGGGTGAAC CAACTTCGAA ACATGAACCA AACGCCACTT TCTCCAAAGA +1  F   Y   T   D   K   E   W   K   G   I   V   E   Q   C   C   T   S
1301  TCTACACTGA CAAGGAATGG AAGGGTATCG TTGAACAATG CTGTACCTCC
      AGATGTGACT GTTCCTTACC TTCCCATAGC AACTTGTTAC GACATGGAGG +1   I   C   S   L   Y   Q   L   E   N   Y   C   N   *
1351  ATCTGCTCCT TGTACCAATT GGAAAACTAC TGCAACTAGA CGCAGCCCGC
      TAGACGAGGA ACATGGTTAA CCTTTTGATG ACGTTGATCT GCGTCGGGCG XbaI
            ~~~~~~
1401  AGGCTCTAGA AACTAAGATT AATATAATTA TATAAAAATA TTATCTTCTT
      TCCGAGATCT TTGATTCTAA TTATATTAAT ATATTTTTAT AATAGAAGAA
```

Fig. 9

METHOD FOR MAKING INSULIN PRECURSORS AND INSULIN PRECURSOR ANALOGS

CROSS-REFERENCE TO RELATED APPLICATIONS

This application claims priority under 35 U.S.C. 119 of U.S. provisional application Nos. 60/181,443 filed on Feb. 10, 2000; 60/211,441 filed on Jun. 13, 2000, and Danish application Nos. PA 1999 01868 filed on Dec. 29, 1999 and PA 2000 00440 filed on Mar. 17, 2000, the contents of which are fully incorporated herein by reference.

BACKGROUND

Yeast organisms produce a number of proteins that have a function outside the cell. Such proteins are referred to as secreted proteins. These secreted proteins are expressed initially inside the cell in a precursor or a pre-form containing a pre-peptide sequence ensuring effective direction (translocation) of the expressed product across the membrane of the endoplasmic reticulum (ER). The pre-peptide, normally named a signal peptide, is generally cleaved off from the desired product during translocation. Once entered in the secretory pathway, the protein is transported to the Golgi apparatus. From the Golgi, the protein can follow different routes that lead to compartments such as the cell vacuole or the cell membrane, or it can be routed out of the cell to be secreted to the external medium (Pfeffer et al. (1987) Ann. Rev. Biochem. 56:829–852).

Insulin is a polypeptide hormone secreted by β-cells of the pancreas and consists of two polypeptide chains, A and B, which are linked by two inter-chain disulphide bridges. Furthermore, the A-chain features one intra-chain disulphide bridge.

The hormone is synthesized as a single-chain precursor proinsulin (preproinsulin) consisting of a prepeptide of 24 amino acid followed by proinsulin containing 86 amino acids in the configuration: prepeptide - B - Arg Arg - C - Lys Arg -A, in which C is a connecting peptide of 31 amino acids. Arg-Arg and Lys-Arg are cleavage sites for cleavage of the connecting peptide from the A and B chains.

Three major methods have been used for the production of human insulin in microorganisms. Two involve *Escherichia coli*, with either the expression of a large fusion protein in the cytoplasm (Frank et al. (1981) in Peptides: Proceedings of the 7$^{th}$ American Peptide Chemistry Symposium (Rich & Gross, eds.), Pierce Chemical Co., Rockford, Ill. pp 729–739), or use a signal peptide to enable secretion into the periplasmic space (Chan et al. (1981) PNAS 78:5401–5404). A third method utilizes *Saccharomyces cerevisiae* to secrete an insulin precursor into the medium (Thim et al. (1986) PNAS 83:6766–6770). The prior art discloses a limited number of insulin precursors which are expressed in either *E. coli* or *Saccharomyces cerevisiae*, vide U.S. Pat. No. 5,962,267, WO 95/16708, EP 0055945, EP 0163529, EP 0347845 and EP 0741188.

Circular Dichroism (CD) is used to determine protein stability and relative stabilities of molecules. CD observed below 240 nm is due to the peptide amide chromophore and may be used to estimate protein secondary structure (Johnson (1988) Ann. Rev. Biophys.Chem. 17:145–166). The spectrum of insulin is characterized by minima at 220 and 209 nm, a negative to positive crossover near 203 nm, and a maximum at 195 nm. Upon denaturation, the negative CD in the 240–218-nm range gradually diminishes, consistent with the loss of ordered secondary structure that accompanies protein unfolding. Consequently, the folding stability of an insulin precursor may be quantitated by measuring the loss of secondary structure as a function of added denaturant, e.g., guanidinium hydrochloride (GuHCl) (see e.g., Pace (1975) CRC Crit. Rev. Biochem. 3:1–43).

SUMMARY OF THE INVENTION

The present invention features novel connecting peptides (C-peptides) which confer an increased production yield and/or increased stability in insulin precursor molecules and insulin precursor analog molecules when expressed in a transformed microorganism, in particular yeast. Such insulin precursors or insulin precursor analogs can then be converted into insulin or an insulin analog by one or more suitable, well known conversion steps.

The connecting peptides of the present invention contain at least one aromatic amino acid residue Phe, Trp, or Tyr and will generally be shorter than the natural human C peptide which, including the flanking dibasic cleavage sites, consists of 35 amino acids. Thus the novel connecting peptides will in general not be of more than 15 amino acid residues in length and preferably not more than 9 amino acid residues. Typically the novel connecting peptides will be of up to 7 or up to 5 amino acid residues and preferably not more than 4 amino acid residues.

As in the natural human insulin molecule, the connecting peptide will contain a cleavage site at its C and N termini enabling in vitro cleavage of the connecting peptide from the A and B chains. Such cleavage sites may be any convenient cleavage sites known in the art, e.g. a Met cleavable by cyanogen bromide; a single basic amino acid residue or a pair of basic amino acid residues (Lys or Arg) cleavable by trypsin or trypsin like proteases; *Acromobactor lyticus* protease or by a carboxypeptidase protease. The cleavage site enabling cleavage of the connecting peptide from the A-chain is preferably a single basic amino acid residue Lys or Arg, preferably Lys.

Alternatively, cleavage of the connecting peptide from the B chain may be enabled by cleavage at the natural Lys$^{B29}$ amino acid residue in the B chain giving rise to a desB30 insulin precursor or desB30 insulin precursor analog. The desired B30 amino acid residue may then be added by well known in vitro, enzymatic procedures.

In one embodiment the connecting peptide will not contain two adjacent basic amino acid residues (Lys, Arg). In this embodiment, cleavage from the A-chain may be accomplished at a single Lys or Arg located at the N-terminal end of the A-chain and the natural Lys in position B29 in the B-chain.

The connecting peptide may comprise more than one aromatic amino acid residue but preferably not more than 5. The aromatic amino acid residues may be the same or different. The connecting peptide will preferably not comprise more than 3 aromatic amino acid residues and most preferred it will only comprise a single aromatic amino acid residue.

In one embodiment of the present invention one of the aromatic amino acid residues in the connecting peptide is immediately N-terminal to the cleavage site adjacent to the A chain. Furthermore, one of the aromatic amino acid residues will preferably be positioned less than 5 Å away from at least one of the residues in positions B11, B12 or B26 in the B chain. In one embodiment, the aromatic amino acid immediately N-terminal to the cleavage site adjacent to the A chain is less than 5 Å away from at least one of the residues in positions B11, B12 or B26 in the B chain.

The insulin precursors or insulin precursor analogs are characterized by having a high folding stability in solution. The precursors according to the present invention will have an increased Cmid stability compared to insulin or insulin analogs, which do not comprise an aromatic amino acid residue in the connecting peptide. The Cmid stability is thus higher than about 5.5 M GuHCl, typically higher than about 6.0 M GuHCl and more typically higher than about 6.5 M GuHCl.

Accordingly, in one aspect the present invention relates to insulin precursors or insulin precursor analogs comprising a connecting peptide (C-peptide) being cleavable from the A and B chains and comprising at least one aromatic amino acid residue and a cleavage site enabling cleavage of the peptide bond between the A-chain and the connecting peptide, wherein one aromatic amino acid residue is immediately N-terminal to said cleavage site.

In another aspect the present invention relates to insulin precursors or insulin precursor analogs comprising a connecting peptide (C-peptide) being cleavable from the A and B chains and consisting of up to 9 amino acid residues of which at least one is an aromatic amino acid residue.

In still a further aspect the present invention relates to an insulin precursor or an insulin precursor analog comprising a connecting peptide (C-peptide) being cleavable from the A and B chains, wherein the connecting peptide contains one aromatic amino acid residue which is less than 5 Å away from at least one of the residues in positions B11, B12 or B26 in the B chain.

In still a further aspect the present invention is related to insulin precursors or insulin precursor analogs comprising a connecting peptide (C-peptide) comprising at least one aromatic amino acid residue and being cleavable from the A and B chains Said insulin precursors or insulin precursor analogs having an increased Cmid stability relative to insulin precursor or insulin precursor analogs which do not comprise an aromatic amino acid residue a the connecting peptide.

The increased activity is determined by a variety of methods known to one of skill in the art, and described below. In one embodiment, increased stability is measured by CD determination of the concentration of guanidine hydrochloride (GuHCl) needed to achieve half-maximum unfolding of an insulin precursor molecule (Cmid).

In a further aspect, the present invention is related to insulin precursors or insulin precursor analogs comprising the formula:

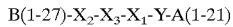

wherein
  $X_1$ is a peptide sequence of 1–15 amino acid residues comprising one aromatic amino acid residue immediately N-terminal to Y,
  $X_2$ is one of Pro, Asp, Lys, or Ile at position 28 of the B chain,
  $X_3$ is one of Pro, Lys, Ala, Arg or Pro-Thr at position 29 of the B chain, and
  Y is Lys or Arg.

In one embodiment, the total number of amino acid residues in $X_1$ will be from 1–10, 1–9, 1–8, 1–7, 1–6, 1–5 or 1–4 amino acid residues in length. In another specific embodiment $X_1$ is 1–3 amino acid residues and preferably 1–2 amino acid residues. The amino acid residues in $X_1$ can be any codable amino acid residue and may be the same or different with the only proviso that one is an aromatic amino acid residue immediately N-terminal to Y.

In a further aspect, the present invention is related to insulin precursors or insulin precursor analogs comprising the formula:

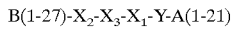

wherein
  $X_1$ is a peptide sequence of 1–15 amino acid residues of which one is an aromatic amino acid residue which is less than 5 Å away from at least one of the amino acid residues in position B11, B12 or B26 in the B chain,
  $X_2$ is one of Pro, Asp, Lys, or Ile at position 28 of the B chain,
  $X_3$ is one of Pro, Lys, Ala, Arg or Pro-Thr at position 29 of the B chain, and
  Y is Lys or Arg.

In one embodiment the number of amino acid residues in $X_1$ is 1–9, 1–5 or 1–4. In another embodiment the number of amino acid residues is 1–3 or 1–2.

In another aspect, the present invention is related to insulin precursors or insulin precursor analogs comprising the formula:

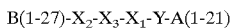

wherein
  $X_1$ is a peptide sequence of 1–8 amino acid residues of which at least one is an aromatic amino acid residue,
  $X_2$ is one of Pro, Asp, Lys, or Ile at position 28 of the B chain,
  $X_3$ is one of Pro, Lys, Ala, Arg or Pro-Thr at position 29 of the B chain, and
  Y is Lys or Arg.

The total number of amino acid residues in $X_1$ will be from 1–7, 1–6, 1–5 or 1–4 amino acid residues. In a more specific embodiment $X_1$ is 1–3 amino acid residues and preferably 1–2 amino acid residues. The amino acid residues in $X_1$ can be any codable amino acid residue and may be the same or different with the only proviso that at least one amino acid residue in $X_1$ is an aromatic amino acid residue.

In the above formulas $X_1$ may comprise up to 5 aromatic amino acid residues which may be the same or different. In a specific embodiment, $X_1$ comprises up to 3 aromatic amino acid residues which may be the same or different and $X_1$ will preferably contain only one aromatic amino acid residue. The aromatic amino acid residues are Trp, Phe or Tyr, preferably Phe or Trp.

In one embodiment, $X_2$ is Asp and $X_3$ is Lys. This embodiment encompasses the insulin precursor analogs containing an Asp in position B28 of the B chain (termed hereinafter "Asp$^{B28}$IP"). In another embodiment $X_2$ is Lys and $X_3$ is Pro. In a further embodiment the sequence $X_1$-Y is selected from the group of:

(a) Met-Trp-Lys; (b) Ala-Trp-Lys; (c) Val-Trp-Lys; (d) Ile-Trp-Lys; (e) Leu-Trp-Lys; (f) Glu-Glu-Phe-Lys (SEQ ID NO:15); (g) Glu-Phe-Lys; (h) Glu-Trp-Lys; (i) Ser-Trp-Lys; (j) Thr-Trp-Lys; (k) Arg-Trp-Lys; (l) Glu-Met-Trp-Lys (SEQ ID NO:1); (m) Gln-Met-Trp-Lys (SEQ ID NO:2); and (n) Asp-Trp-Lys.

In another embodiment $X_2$ is Pro, $X_3$ is Lys and $X_1$ is 1–2 amino acid residues of which one is Trp or Phe.

In another embodiment $X_2$ is Lys, $X_3$ is Pro-Thr and $X_1$ consists of up to 15 amino acid residues of which one is Trp, Tyr or Phe. In this embodiment $X_1$ will contain a cleavage site at the C-terminal end, e.g a mono basic or dibasic (Lys, Arg) cleavage site.

The present invention is also related to polynucleotide sequences which code for the claimed insulin precursors or insulin precursor analogs. In a further aspect the present invention is related to vectors containing such polynucleotide sequences and host cell containing such polynucleotide sequences or vectors.

In another aspect, the invention relates to a process for producing the insulin precursors or insulin precursor analogs in a host cell, said method comprising (i) culturing a host cell comprising a polynucleotide sequence encoding the insulin precursors or insulin precursor analogs of the invention under suitable conditions for expression of said precursor or precursor analog; and (ii) isolating the precursor or precursor analog from the culture medium.

In still a further aspect, the invention relates to a process for producing insulin or insulin analogs in a host cell said method comprising (i) culturing a host cell comprising a polynucleotide sequence encoding an insulin precursor or insulin precursor analogs of the invention; (ii) isolating the precursor or precursor analog from the culture medium and (iii) converting the precursor or precursor analog into insulin or an insulin analog by in vitro enzymatic conversion.

In one embodiment of the present invention the host cell is a yeast host cell and in a further embodiment the yeast host cell is selected from the genus Saccharomyces. In a further embodiment the yeast host cell is selected from the species *Saccharomyces cerevisiae*.

BRIEF DESCRIPTION OF THE DRAWINGS

FIG. 2 is the DNA sequence and inferred amino acid sequence of the encoded fusion protein (α-factor-leader-EEAEAEAPK(SEQ ID NO:4)-Asp$^{B28}$IP portion of pAK1150 (SEQ ID NO: 5 and 6) used as PCR template.

FIG. 3 is the DNA sequence encoding α-factor leader-Asp$^{B28}$IP(GluTrpLys) fusion protein with a synthetic mini C-peptide GluTrpLys generated by randomized optimization (SEQ ID NO:7 and 8). The mini C-peptide (EWK) is indicated by underlining.

FIG. 8 is the DNA and inferred amino acid sequence of the expression cassette expressing the YAP3-TA39-EEGEPK(SEQ ID NO:17)-Asp$^{B28}$IP fusion protein with a synthetic mini C-peptide GluTrpLys (SEQ ID NO:9 and 10) and FIG. 9 is the DNA and inferred amino acid sequence of the expression cassette expressing plasmid expressing the YAP3-TA57-EEGEPK(SEQ ID NO:17)-Asp$^{B28}$IP fusion protein with a synthetic mini C-peptide GluTrpLys (SEQ ID NO:11 and 12).

DETAILED DESCRIPTION

Abbreviations and Nomenclature

Figure 1:
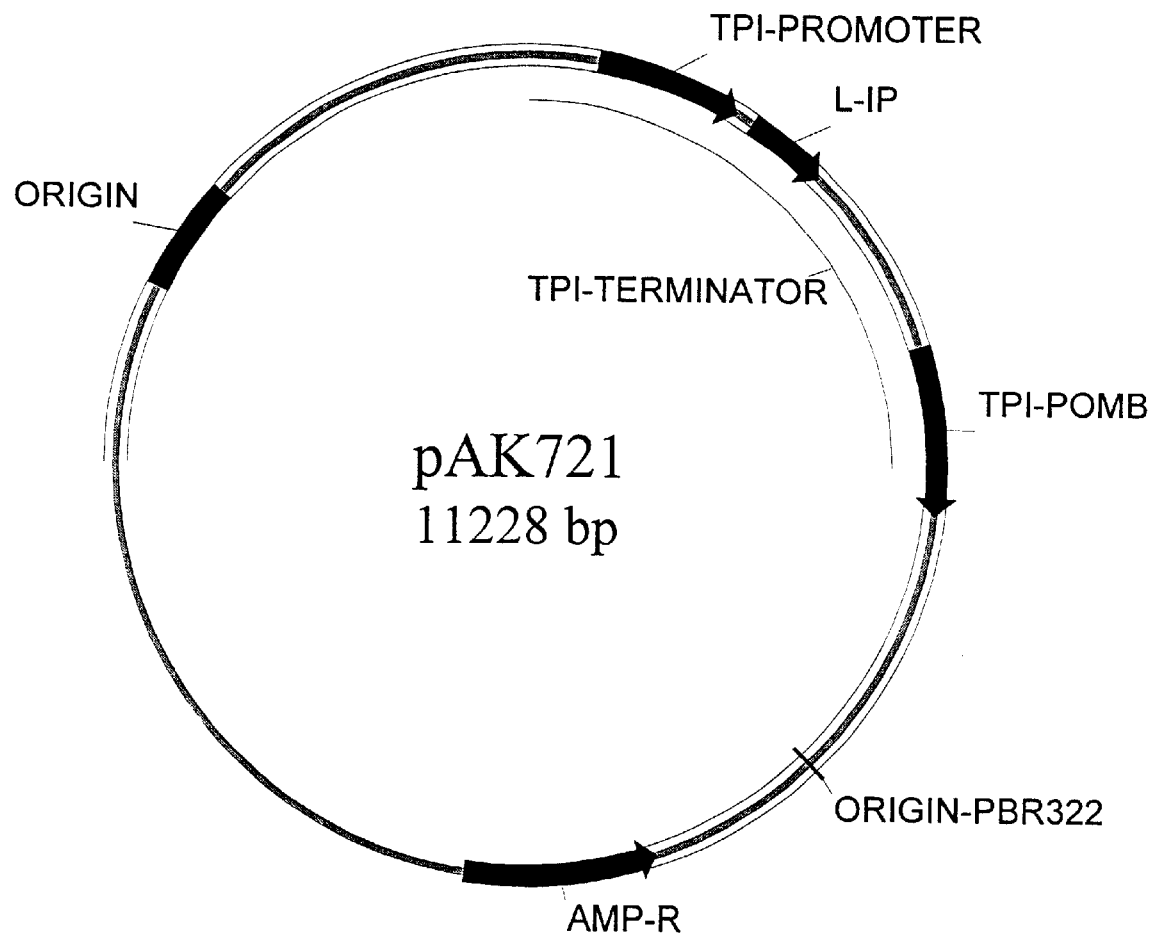
FIG. 1 represents the pAK721 *S. cerevisiae* expression plasmid expressing the LA19 leader-EEAEAEAEPK(SEQ ID NO:3)-IP(AlaAlaLys) fusion protein.
Figure 4:
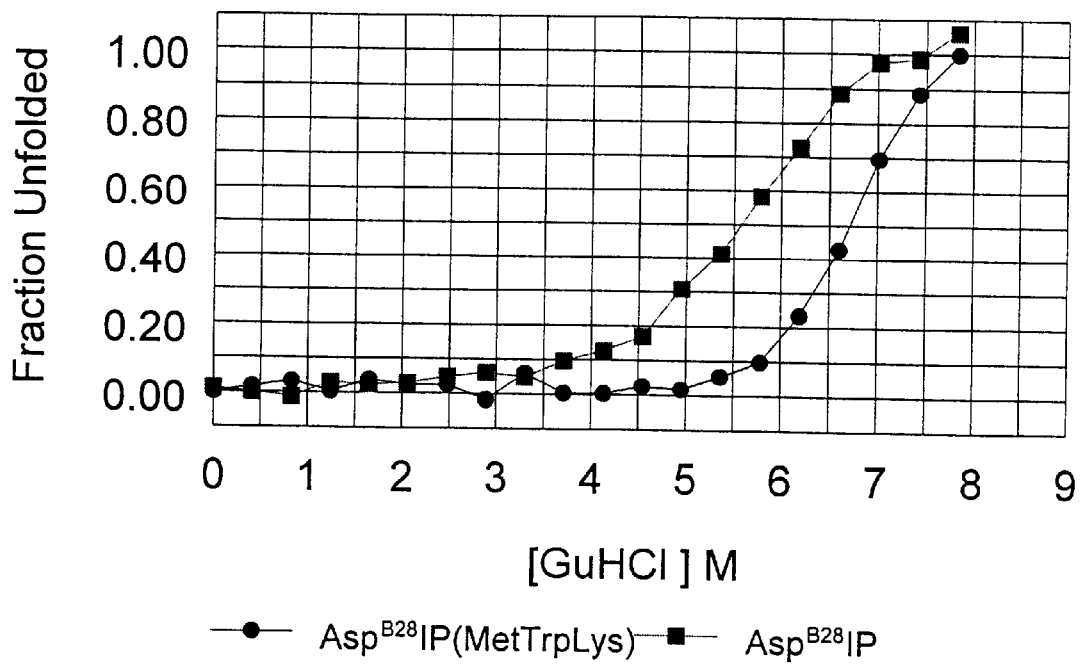
FIG. 4 shows folding stability of the insulin analog Asp$^{B28}$IP(MetTrpLys) relative to Asp$^{B28}$IP.

By "connecting peptide" or "C-peptide" is meant the connection moiety "C" of the B-C-A polypeptide sequence of a single chain preproinsulin-like molecule. Specifically, in the natural insulin chain, the C-peptide connects position 30 of the B chain and position 1 of the A chain. A "mini C-peptide" or "connecting peptide" such as those described herein, connect B29 or B30 to A1, and differ in sequence and length from that of the natural C-peptide.

By "IP" is meant a single-chain insulin precursor in which a desB30 chain is linked to the A chain of insulin via a connecting peptide. The single-chain insulin precursor will contain correctly positioned disulphide bridges (three) as in human insulin.

With "desB30" or "B(1–29)" is meant a natural insulin B chain lacking the B30 amino acid residue, "A(1–21)" means the natural insulin A chain, "B(1–27)" means the natural B chain lacking the B28, B29, and B30 amino acid residues; "Asp$^{B28}$IP" means a single-chain insulin precursor with aspartic acid at position 28 of the B-chain and no C-peptide (B29 is linked to A1). The mini C-peptide and its amino acid sequence is indicated in the three letter amino acid code in parenthesis following the IP; Thus "Asp$^{B28}$IP(MetTrpLys)" means a single-chain insulin precursor with aspartic acid at position 28 of the B-chain and a mini C-peptide with the sequence Met-Trp-Lys connecting B29 to A1.

By "insulin precursor" is meant a single-chain polypeptide which by one or more subsequent chemical and/or enzymatic processes can be converted into human insulin.

By "insulin precursor analog" is meant an insulin precursor molecule having one or more mutations, substitutions, deletions and or additions of the A and/or B amino acid chains relative to the human insulin molecule. The insulin analogs are preferably such wherein one or more of the naturally occurring amino acid residues, preferably one, two, or three of them, have been substituted by another codable amino acid residue. In one embodiment, the instant invention comprises analog molecules having position 28 of the B chain altered relative to the natural human insulin molecule. In this embodiment, position 28 is modified from the natural Pro residue to one of Asp, Lys, or Ile. In a preferred embodiment, the natural Pro residue at position B28 is modified to an Asp residue. In another embodiment Lys at position B29 is modified to Pro; Also, Asn at position A21 may be modified to Ala, Gln, Glu, Gly, His, Ile, Leu, Met, Ser, Thr, Trp, Tyr or Val, in particular to Gly, Ala, Ser, or Thr and preferably to Gly. Furthermore, Asn at position B3 may be modified to Lys. Further examples of insulin precursor analogs are des(B30) human insulin, insulin analogs wherein Phe$^{B1}$ has been deleted; insulin analogs wherein the A-chain and/or the B-chain have an N-terminal extension and insulin analogs wherein the A-chain and/or the B-chain have a C-terminal extension. Thus one or two Arg may be added to position B1.

The term "immediately N-terminal to" is meant to illustrate the situation where an amino acid residue or a peptide sequence is directly linked at its C-terminal end to the N-terminal end of another amino acid residue or amino acid sequence by means of a peptide bond.

In the present context, the term "functional analog of insulin" and the like, is meant to indicate a polypeptide with a similar biological action as the native human insulin protein.

By a distance shorter than 5 Å between two amino acid residues is meant the shortest inter-atomic distance less than 5 Å between any atom in the first amino acid and any atom in the second amino acid. Atomic distances are measured from three-dimensional structures of the molecule determined either by NMR (Wüthrich, K., 1986, NMR of Proteins and Nucleic Acids, Wiley, New York) or by X-ray crystallography (Drenth, J., 1994, Principles of Protein X-ray crystallography, Springer Verlag Berlin). A distance from one amino acid to another is measured as the shortest inter-atomic distance between any atom in the first amino acid and any atom in the second amino acid if not stated differently.

The present invention features novel mini C-peptides connecting position 29 of the insulin B chain and position 1 of the insulin A chain which significantly increased production yields in a yeast host cell. By the term "significantly increased production," "increased fermentation yield," and the like, is meant an increase in secreted amount of the insulin precursor molecule or insulin precursor analog molecule present in the culture supernatant compared to the yield of an insulin precursor or insulin precursor analog with no aromatic amino acid residue in the mini C peptide. An "increased" fermentation yield is an absolute number larger than the control; preferably, the increase is 50% or more larger than the control ($AspB^{28}$ IP) level; even more preferably, the increase is 100% or more larger than control levels.

By the term "increase in stability" is meant, for example, an increased value of Cmid in solution relative to that obtained for an insulin analog precursor (e.g., $Asp^{B28}IP$) without an aromatic amino acid residue in the mini C-peptide. By the term "Cmid" is meant the concentration of GuHCl necessary to unfold one-half of the protein population in an assay measuring the far-UV circular dichroism of the insulin molecule as a function of increasing concentrations of denaturant.

"POT" is the *Schizosaccharomyces pombe* triose phosphate isomerase gene, and "TPI1" is the *S. cerevisiae* triose phosphate isomerase gene.

By a "leader" is meant an amino acid sequence consisting of a pre-peptide (the signal peptide) and a pro-peptide.

The term "signal peptide" is understood to mean a pre-peptide which is present as an N-terminal sequence on the precursor form of a protein. The function of the signal peptide is to allow the heterologous protein to facilitate translocation into the endoplasmic reticulum. The signal peptide is normally cleaved off in the course of this process. The signal peptide may be heterologous or homologous to the yeast organism producing the protein. A number of signal peptides which may be used with the DNA construct of the invention including yeast aspartic protease 3 (YAP3) signal peptide or any functional analog (Egel-Mitani et al. (1990) YEAST 6:127–137 and U.S. Pat. No. 5,726,038) and the α-factor signal of the MFα1 gene (Thorner (1981) in *The Molecular Biology of the Yeast Saccharomyces cerevisiae*, Strathern et al., eds., pp 143–180, Cold Spring Harbor Laboratory, NY and U.S. Pat. No. 4,870,00.

The term "pro-peptide" means a polypeptide sequence whose function is to allow the expressed polypeptide to be directed from the endoplasmic reticulum to the Golgi apparatus and further to a secretory vesicle for secretion into the culture medium (i.e. exportation of the polypeptide across the cell wall or at least through the cellular membrane into the periplasmic space of the yeast cell). The pro-peptide may be the yeast α-factor pro-peptide, vide U.S. Pat. No. 4,546,082 and 4,870,008. Alternatively, the pro-peptide may be a synthetic pro-peptide, which is to say a pro-peptide not found in nature. Suitable synthetic pro-peptides are those disclosed in U.S. Pat. Nos. 5,395,922; 5,795,746; 5,162,498 and WO 98/32867. The pro-peptide will preferably contain an endopeptidase processing site at the C-terminal end, such as a Lys-Arg sequence or any functional analog thereof.

The polynucleotide sequence of the invention may be prepared synthetically by established standard methods, e.g. the phosphoamidite method described by Beaucage et al. (1981) Tetrahedron Letters 22:1859–1869, or the method described by Matthes et al. (1984) EMBO Journal 3:801–805. According to the phosphoamidite method, oligonucleotides are synthesized, for example, in an automatic DNA synthesizer, purified, duplexed and ligated to form the synthetic DNA construct. A currently preferred way of preparing the DNA construct is by polymerase chain reaction (PCR).

The polynucleotide sequence of the invention may also be of mixed genomic, cDNA, and synthetic origin. For example, a genomic or cDNA sequence encoding a leader peptide may be joined to a genomic or cDNA sequence encoding the A and B chains, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides.

The invention encompasses a vector which is capable of replicating in the selected microorganism or host cell and which carries a polynucleotide sequence encoding the insulin precursors or insulin precursor analogs of the invention. The recombinant vector may be an autonomously replicating vector, i.e., a vector which exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome.

In a preferred embodiment, the recombinant expression vector is capable of replicating in yeast Examples of sequences which enable the vector to replicate in yeast are the yeast plasmid 2 μm replication genes REP 1–3 and origin of replication.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Selectable markers for use in a filamentous fungal host cell include amdS (acetamidase), argB (ornithine carbamoyl-transferase), pyrG (orotidine-5'-phosphate decarboxylase) and trpC (anthranilate synthase. Suitable markers for yeast host cells are ADE2, HIS3, LEU2, LYS2, MET3, TRP1, and URA3. A preferred selectable marker for yeast is the *Schizosaccharomyces pompe* TPI gene (Russell (1985) Gene 40:125–130).

In the vector, the polynucleotide sequence is operably connected to a suitable promoter sequence. The promoter may be any nucleic acid sequence which shows transcriptional activity in the host cell of choice including mutant, truncated, and hybrid promoters, and may be obtained from genes encoding extra-cellular or intra-cellular polypeptides either homologous or heterologous to the host cell.

Examples of suitable promoters for directing the transcription in a bacterial host cell, are the promoters obtained from the E. coli lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), and *Bacillus licheniformis* penicillinase gene (penP). Examples of suitable promoters for directing the transcription in a filamentous fungal host cell are promoters obtained from the genes for *Aspergillus oryzae* TAKA amylase, *Rhizomucor miehei* aspartic proteinase, *Aspergillus niger* neutral alpha-amylase, and *Aspergillus niger* acid stable alpha-amylase. In a yeast host, useful promoters are the *Saccharomyces cerevisiae* Ma1, TPI, ADH or PGK promoters.

The polynucleotide construct of the invention will also typically be operably connected to a suitable terminator. In yeast a suitable terminator is the TPI terminator (Alber et al. (1982) J. Mol. Appl. Genet. 1:419–434).

The procedures used to ligate the polynucleotide sequence of the invention, the promoter and the terminator, respectively, and to insert them into suitable yeast vectors containing the information necessary for yeast replication, are well known to persons skilled in the art. It will be understood that the vector may be constructed either by first preparing a DNA construct containing the entire DNA sequence encoding the insulin precursors or insulin precursor analogs of the invention, and subsequently inserting this fragment into a suitable expression vector, or by sequentially inserting DNA fragments containing genetic information for the individual elements (such as the signal, pro-peptide, mini C-peptide, A and B chains) followed by ligation.

The present invention also relates to recombinant host cells, comprising a polynucleotide sequence encoding the insulin precursors or the insulin precursor analogs of the invention. A vector comprising such polynucleotide sequence is introduced into the host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source. The host cell may be a unicellular microorganism, e.g., a prokaryote, or a non-unicellular microorganism, e.g., a eukaryote. Useful unicellular cells are bacterial cells such as gram positive bacteria including, but not limited to, a Bacillus cell, Streptomyces cell, or gram negative bacteria such as *E. coli* and Pseudomonas sp. Eukaryote cells may be mammalian, insect, plant, or fungal cells. In a preferred embodiment, the host cell is a yeast cell. The yeast organism used in the process of the invention may be any suitable yeast organism which, on cultivation, produces large amounts of the insulin precursor and insulin precursor analogs of the invention. Examples of suitable yeast organisms are strains selected from the yeast species *Saccharomyces cerevisiae, Saccharomyces kluyveri, Schizosaccharomyces pombe, Sacchoromyces uvarum, Kluyveromyces lactis, Hansenula polymorpha, Pichia pastoris, Pichia methanolica, Pichia kluyveri, Yarrowia lipolytica*, Candida sp., *Candida utilis, Candida cacaoi*, Geotrichum sp., and *Geotrichum fermentans*.

The transformation of the yeast cells may for instance be effected by protoplast formation followed by transformation in a manner known per se. The medium used to cultivate the cells may be any conventional medium suitable for growing yeast organisms. The secreted insulin precursor or insulin precursor analogs of the invention, a significant proportion of which will be present in the medium in correctly processed form, may be recovered from the medium by conventional procedures including separating the yeast cells from the medium by centrifugation, filtration or catching the insulin precursor or insulin precursor analog by an ion exchange matrix or by a reverse phase absorption matrix, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

The insulin precursors and insulin precursor analogs of the invention may be expressed with an N-terminal amino acid residue extension, as described in U.S. Pat. No. 5,395, 922, and European Patent No. 765,395A, both of which patents are herein specifically incorporated by reference. The extension is found to be stably attached to the insulin precursor or insulin precursor analogs of the invention during fermentation, protecting the N-terminal end of the insulin precursor or insulin precursor analog against the proteolytic activity of yeast proteases such as DPAP. The presence of an N-terminal extension on the insulin precursor or insulin precursor analog may also serve as a protection of the N-terminal amino group during chemical processing of the protein, i.e. it may serve as a substitute for a BOC (t-butyl-oxycarbonyl) or similar protecting group. The N-terminal extension may be removed from the recovered insulin precursor or insulin precursor analog by means of a proteolytic enzyme which is specific for a basic amino acid (e.g., Lys) so that the terminal extension is cleaved off at the Lys residue. Examples of such proteolytic enzymes are trypsin or *Achromobacter lyticus* protease.

After secretion to the culture medium and recovery, the insulin precursor or insulin precursor analogs of the invention will be subjected to various in vitro procedures to remove the possible N-terminal extension sequence and the mini C-peptide to give insulin or the desired insulin analog. Such methods include enzymatic conversion by means of trypsin or an *Achromobacter lyticus* protease in the presence of an L-threonine ester followed by conversion of the threonine ester of the insulin or insulin analog into insulin or the insulin analog by basic or acid hydrolysis as described in U.S. Pat. Nos. 4,343,898 or 4,916,212 or Research Disclosure, September 1994/487 the disclosures of which are incorporated by reference hereinto.

As described below, insulin precursors or insulin precursor analogs with synthetic C-peptides were constructed featuring at least one aromatic amino acid (Example 1). *Saccharomyces cerevisiae* expression plasmids containing a polynucleotide sequence encoding the claimed insulin precursors or insulin precursor analogs were constructed by PCR and used to transform a *S. cerevisiae* host cell. The amount of expressed product, e.g. an insulin analog was measured as a percentage of the relevant control level, e.g. amount of expressed $Asp^{B28}IP$ lacking mini C-peptide (Table 1) and $Asp^{B28}IP(AlaAlaLys)$ with a mini C-peptide without an aromatic amino acid residue (Table 2). The novel C-peptides of the invention gave increased yields by up to 7-fold levels.

The present invention is described in further detain in the following examples which are not in any way intended to limit the scope of the invention as claimed. The attached Figures are meant to be considered as integral parts of the specification and description of the invention. All references cited are herein specifically incorporated by reference for all that is described therein.

EXAMPLES

General Procedures

All expressions plasmids are of the C-POT type, similar to those described in EP 171, 142, which are characterized by containing the *Schizosaccharomyces pombe* triose phosphate isomerase gene (POT) for the purpose of plasmid selection and stabilization in *S. cerevisiae*. The plasmids also contain the *S. cerevisiae* triose phosphate isomerase promoter and terminator. These sequences are similar to the corresponding sequences in plasmid pKFN1003 (described in WO 90/100075) as are all sequences except the sequence of the EcoRl-Xbal fragment encoding the fusion protein of the leader and the insulin precursor product. In order to express different fusion proteins, the EcoRI-Xbal fragment of pKFN1003 is simply replaced by an EcoRI-Xbal fragment encoding the leader-insulin precursor-fusion of interest. Such EcoRI-Xbal fragments may be synthesized using synthetic oligonucleotides and PCR according to standard techniques.

Yeast transformants were prepared by transformation of the host strain *S. cerevisiae* strain MT663 (MATa/MATα pep4-3/pep4-3 HIS4/his4 tpi::LEU2/tpi::LEU2 Cir$^+$). The yeast strain MT663 was deposited in the Deutsche Sammlung von Mikroorganismen und Zellkulturen in connection with filing WO 92/11378 and was given the deposit number DSM 6278.

MT663 was grown on YPGaL (1% Bacto yeast extract, 2% Bacto peptone, 2% galactose, 1% lactate) to an O.D. at 600 nm of 0.6. 100 ml of culture was harvested by centrifugation, washed with 10 ml of water, recentrifuged and resuspended in 10 ml of a solution containing 1.2 M sorbitol, 25 mM $Na_2EDTA$ pH=8.0 and 6.7 mg/ml dithiotreitol. The suspension was incubated at 30° C. for 15 minutes, centrifuged and the cells resuspended in 10 ml of a solution containing 1.2 M sorbitol, 10 mM $Na_2EDTA$, 0.1 M sodium citrate, pH 0 5.8, and 2 mg Novozym®234. The suspension was incubated at 30° C. for 30 minutes, the cells collected by centrifugation, washed in 10 ml of 1.2 M sorbitol and 10 ml of CAS (1.2 M sorbitol, 10 mM $CaCl_2$, 10 mM Tris HCl (Tris=Tris(hydroxymethyl)aminomethane) pH=7.5) and resuspended in 2 ml of CAS. For transformation, 1 ml of CAS-suspended cells was mixed with approx. 0.1 mg of plasmid DNA and left at room temperature for 15 minutes. 1 ml of (20% polyethylene glycol 4000, 10 mM $CaCl_2$, 10 mM Tris HCl, pH=7.5) was added and the mixture left for a further 30 minutes at room temperature. The mixture was centrifuged and the pellet resuspended in 0.1 ml of SOS (1.2 M sorbitol, 33% v/v YPD, 6.7 mM $CaCl_2$) and incubated at 30° C. for 2 hours. The suspension was then centrifuged and the pellet resuspended in 0.5 ml of 1.2 M sorbitol. Then, 6 ml of top agar (the SC medium of Sherman et al. (1982) *Methods in Yeast Genetics*, Cold Spring Harbor Laboratory) containing 1.2 M sorbitol plus 2.5% agar) at 52° C. was added and the suspension poured on top of plates containing the same agar-solidified, sorbitol containing medium.

*S. cerevisiae* strain MT663 transformed with expression plasmids was grown in YPD for 72 h at 30° C. Quantitation of the insulin-precursor yield in the culture supernatants was performed by reverse-phase HPLC analysis with human insulin as an external standard (Snel & Damgaard (1988) Proinsulin heterogenity in pigs. Horm. Metabol. Res. 20:476–488).

Example 1

Construction of Synthetic C-peptides With Aromatic Amino Acid(s)

Synthetic genes encoding fusion proteins, consisting of $Asp^{B28}$IP associated with a leader sequence consisting of a pre-peptide (signal peptide) and a pro-peptide, were constructed using PCR under standard conditions (Sambrook et al. (1989) Molecular Cloning, Cold Spring Harbor Laboratory Press) and E.H.F. polymerase (Boehringer Mannheim GmbH, Sandhoefer Strasse 116, Mannheim, Germany). The resulting DNA fragments were isolated and digested with endonucleases and purified using the Gene Clean kit (Bio101 Inc., La Jolla, Calif., USA). Standard methods were used for DNA ligation and transformation of *E. coli* cells were performed by the $CaCl_2$ method (Sambrook et al. (1989) supra). Plasmids were purified from transformed *E. coli* cells using QIAGEN columns (QIAGEN, Hilden, Germany). Nucleotide sequences were determined using the ALF Pharmacia Biotech DNA sequencing system with purified double-stranded plasmid DNA as template. Oligonucleotide primers for PCR were obtained from DNA technology (Århus, Denmark).

Secretory expression of the $Asp^{B28}$IP in *S. cerevisiae* was performed using the *S. cerevisiae* strain MT663 and the 2 μm based yeast expression vector CPOT (see FIG. 1) as described in Thim, L. et al. (1986) Proc. Natl. Acad. Sci. USA 83:6766–6770. The yeast expression vector contains the *Schizosaccharomyces pombe* triose phosphate isomerase gene (POT) for plasmid selection and stabilization in *S. cerevisiae*. Furthermore, the *S. cerevisiae* triose phosphate isomerase gene (TPI1) promoter and terminator are used for transcription initiation and termination of the recombinant gene encoding the leader-$Asp^{B28}$IP fusion protein. Secretion of the $Asp^{B28}$IP was facilitated by the α-factor leader, although a variety of known yeast leader sequences may be used.

As shown in FIG. 1, the pAK721 *S. cerevisiae* expression plasmid expressing the LA19 leader-EEAEAEAEPK(SEQ ID NO:3)-IP fusion protein was constructed based on the *S. cerevisiae-E. coli* shuttle POT plasmid (U.S. Pat. No. 5,871, 957). In FIG. 1 L-IP indicates the fusion protein expression cassette encoding the leader-IP fusion protein; TPI-PROMOTER is the *S. cerevisiae* TPI1 promoter, TPI-TERMINATOR is the *S. cerevisiae* TPI1 terminator; TPI-POMBE indicates the *S. pombe* POT gene used for selection in *S. cerevisiae*; ORIGIN indicates a *S. cerevisiae* origin of replication derived from the 2 μm plasmid; AMP-R indicates the β-lactamase gene conferring resistance toward ampicillin, facilitating selection in *E. coli*; and ORIGIN-PBR322 indicates an *E. coli* origin of replication.

DNA encoding a number of fusions proteins of leader sequences and $Asp^{B28}$IP with different mini C-peptides was generated by PCR using appropriate oligonucleotides as primers, as described below. Standard methods were used to subclone DNA fragments encoding the leader-$Asp^{B28}$IP fusion proteins into the CPOT expression vector in the following configuration: leader-Lys-Arg-spacer-$Asp^{B28}$IP, where Lys-Arg is a potential dibasic endoprotease processing site and spacer is an N-terminal extension. To optimize processing of the fusion protein by the *S. cerevisiae* Kex2 endoprotease, DNA encoding a spacer peptide (N-terminal extension), e.g. EEAEAEAPK (SEQ ID NO:4), was inserted between the DNA encoding the leader and the $Asp^{B28}IP$ (Kjeldsen et al. (1996) *Gene* 170, 107–112.). However, the present of the spacer peptide is not mandatory. The mature $Asp^{B28}IP$ was secreted as a single-chain N-terminally extended insulin precursor with a mini C-peptide, connecting $Lys^{B29}$ and $Gly^{A1}$. After purification of the $Asp^{B28}IP$ and proteolytic removal of the N-terminal extension and the mini C-peptide, the amino acid $Thr^{B30}$ can be added to $Lys^{B29}$ by enzyme-mediated transpeptidation, to generate $Asp^{B28}$ human insulin (Markussen, et al. (1987) in "Peptides 1986" (Theodoropoulos, D., Ed.), pp. 189–194, Walter de Gruyter & Co., Berlin.).

Development of synthetic mini C-peptides was performed by randomization of one or more codon(s) encoding the amino acids in the mini C-peptide. All synthetic mini C-peptides feature an enzymatic processing site (Lys) at the C-terminus which allows enzymatic removal of the synthetic mini C-peptide (U.S. Pat. No. 4,916,212, herein specifically incorporated by reference). Randomization was performed using doped oligonucleotides which introduced codon(s) variations at one or more positions of the synthetic mini C-peptides. Typically one of the two primers (oligonucleotides) used for PCR was doped. An example of an oligonucleotides pair used for PCR generation of leader-$Asp^{B28}IP$ with randomized synthetic mini C-peptides used to generated synthetic mini C-peptides with the general formula: Xaa-Trp-Lys (XWK) are as follows:

Primer A:
5'-TAAATCTATAACTACAAAAAACACATA-3' (SEQ ID NO:13) and

Primer B:
3'-CCAAAGAAGATGTGACTGTTCNNMACCTTCCCA-TAGCAACTTGTTACAACATGAAGATAGACAAGAA-ACATGGTTAACCTTTTGATGACATTGATCAGATCTT-TGA-TTC-5' (SEQ ID NO:14), where N is A, C, G, or T and M is C or A.

Polymerase chain reaction. PCR was typically performed as indicated below: 5 µl Primer A (20 pmol), 5 µl Primer B (20 pmol), 10 µl 10X PCR buffer, 8 µl dNTP mix, 0.75 µl E.H.F. enzyme, 1 µl pAK1150 plasmid as template (approximately 0.2 µg DNA) and 70.25 µl distilled water.

Typically between 10 and 15 cycles were performed, one cycle typically was 94° C. for 45 sec.; 55° C. for 1 min; 72° C. for 1.5 min. The PCR mixture was subsequently loaded onto a 2% agarose gel and electrophoresis was performed using standard techniques. The resulting DNA fragment was cut out of the agarose gel and isolated by the Gene Clean kit.

FIG. 2 shows the sequence of pAK1150 DNA used as template for PCR and inferred amino acids of the encoded fusion protein (α-factor-leader-(EEAEAEAPK)(SEQ ID NO:4)-$Asp^{B28}IP$ of pAK1150 (SEQ ID NO:5 and 6). The pAK1150 plasmid is similar to pAK721 shown in FIG. 1. The α-factor-leader's C-terminus was modified to introduced a Nco I restriction endonuclease site, which changes the inferred amino acid sequences from SerLeuAsp to SerMetAla. Moreover, the encoded $Asp^{B28}IP$ does not feature a mini C-peptide but $Lys^{B29}$ is directly connected to $Gly^{A1}$.

The purified PCR DNA fragment was dissolved in water and restriction endonucleases buffer and digested with suitable restriction endonucleases (e.g. Bgl II and Xba I) according to standard techniques. The BglII-XbaI DNA fragments were subjected to agarose electrophoresis and purified using The Gene Clean Kit.

The expression plasmid pAK1150 or a similar plasmid of the CPOT type (see FIG. 1) was digested with the restriction endonucleases Bgl II and Xba I and the vector fragment of 10765 nucleotide basepairs isolated using The Gene Clean Kit.

The two digested and isolated DNA fragments (the vector fragment and the PCR fragment) were ligated together using T4 DNA ligase and standard conditions. The ligation mix was subsequently transformed into a competent *E. coli* strain (R–, M+) followed by selection with ampicillin resistance. Plasmids from the resulting *E. coli*'s were isolated using QIAGEN columns.

The plasmids were subsequently used for transformation of a suitable *S. cerevisiae* host strain, e.g., MT663 (MATa/ MATα pep4-3/pep4-3 HIS4/his4 tpi::LEU2/tpi::LEU2 Cir+). Individual transformed *S. cerevisiae* clones were grown in liquid culture, and the quantity of $Asp^{B28}IP$ secreted to the culture supernatants were determined by RP-HPLC. The DNA sequence encoding the synthetic mini C-peptide of the expression plasmids from *S. cerevisiae* clones secreting increased quantity of the $Asp^{B28}IP$ were then determined. Subsequently, the identified synthetic mini C-peptide sequence might be subjected to another round of randomization optimization.

An example on a DNA sequence encoding a leader-$Asp^{B28}IP$(GluTrpLys) fusion protein featuring a synthetic mini C-peptide (GluTrpLys) resulting from the randomized optimization process described is shown in FIG. 3 (SEQ ID NO:7 and 8).

Table 1 and 2 show the insulin precursors analogs generated by the above method and production yield expressed as a percent of control. Fermentation was conducted at 30° C. for 72 h in 5 ml YPD. Yield of the insulin precursor was determined by RP-HPLC of the culture supernatant, and is expressed relative to the yield of a control strain expressing either a leader-$Asp^{B28}IP$ fusion protein in which the B29 residue is linked to the A1 residue by a peptide bond; or leader-$Asp^{B28}IP$ fusion protein in which the B29 residue is linked to the A1 residue by a mini C-peptide, respectively. In the tables, "α*" indicates an α-factor leader in which the C-terminus up to the LysArg has been modified from "SLD (SerLeuAsp)" to "SMA (SerMet Ala)" and "ex4" is an N-terminal extension with the amino acid sequence EEAEAEAPK(SEQ ID NO:4). YAP3 is the YAP3 signal sequence TA39 is a synthetic pro-sequence QPID-DTESNTTSVNLMADDTESRFATNTTLAG-GLDWNLISMAKR (SEQ ID NO:16). The sequence EEGEPK (SEQ ID NO:17) is an N-terminal extension to the B-chain of the insulin analogue. TA57 is a synthetic pro-sequence QPIDDTESQTTSVNLMADDTESAFATQT-NSGGLDWGLISMAKR (SEQ ID NO:18).

TABLE 1

| Leader-N-terminal extension | Precursor | mini C-peptide | Yield* | SEQ ID NO: |
|---|---|---|---|---|
| α*-ex4 | $Asp^{B28}IP$ (control) | None | 100 | |
| α*-ex4 | $Asp^{B28}IP$ | MetTrpLys | 378 | |
| α*-ex4 | $Asp^{B28}IP$ | AlaTrpLys | 270 | |
| α*-ex4 | $Asp^{B28}IP$ | ValTrpLys | 284 | |
| α*-ex4 | $ASP^{B28}IP$ | IleTrpLys | 330 | |
| α*-ex4 | $Asp^{B28}IP$ | LeuTrpLys | 336 | |
| α*-ex4 | $Asp^{B28}IP$ | LysTrpLys | 288 | |
| α*-ex4 | $Asp^{B28}IP$ | GluGluPheLys | 272 | SEQ ID NO: 15 |
| α*-ex4 | $Asp^{B28}IP$ | GluPheLys | 379 | |
| α*-ex4 | $Asp^{B28}IP$ | GluTrpLys | 374 | |

TABLE 1-continued

| Leader-N-terminal extension | Precursor | mini C-peptide | Yield* | SEQ ID NO: |
|---|---|---|---|---|
| α*-ex4 | Asp$^{B28}$IP | SerTrpLys | 226 | |
| α*-ex4 | Asp$^{B28}$IP | ThrTrpLys | 270 | |
| α*-ex4 | Asp$^{B28}$IP | ArgTrpLys | 227 | |
| α*-ex4 | Asp$^{B28}$IP | GluMetTrpLys | 212 | SEQ ID NO: 1 |
| α*-ex4 | Asp$^{B28}$IP | GlnMetTrpLys | 239 | SEQ ID NO: 2 |

TABLE 2

| Leader-N-terminal extension | Precursor | Mini C-peptide | Yield* | SEQ ID NO: |
|---|---|---|---|---|
| α*-ex4 | Asp$^{B28}$IP | AlaAlaLys (control) | 100 | |
| α*-ex4 | Asp$^{B28}$IP | GluTrpLys | 626 | |
| α*-ex4 | Asp$^{B28}$IP | GluTyrLys | 466 | |
| α*-ex4 | Asp$^{B28}$IP | GluPheLys | 444 | |
| α*-ex4 | Asp$^{B28}$IP | AspTrpLys | 460 | |
| YAP3-TA57-EEGEPK | Asp$^{B28}$IP | GluTrpLys | 767 | (SEQ ID NO: 17) |
| YAP3-TA39-EEGEPK | Asp$^{B28}$IP | MetTrpLys | 687 | (SEQ ID NO: 17) |

Example 2

Structure Determination of Asp$^{B28}$IP(MetTrpLys) in Aqueous Solution by NMR Spectroscopy NMR spectroscopy. Samples for NMR were prepared by dissolving the lyophilized protein powder in 10/90 D$_2$O/H$_2$O with a 10 mM phosphate buffer and adjusting the pH as desired by addition of small volumes of 1 M DCl or NaOD. All pH meter readings are without correction for isotope effects. Samples of Asp$^{B28}$IP(MetTrpLys) for NMR were prepared at concentrations ranging from 25 µM to 1 mM at pH 8.0. Two-dimensional $^1$H-$^1$H NMR spectra of 1 mM samples, DQF-COSY (Piantini et al. (1982) J. Am. Chem. Soc. 104:6800–6801, Rance et al. (1983) Biochem. Biophys. Res. Commun. 117:479–485), TOCSY (Braunschweiler et al. (1983) J. Magn. Reson. 53:521–528, Bax et al. (1985) J. Magn. Reson. 65:355–360) and NOESY (Jeener et al. (1979) J. Chem. Phys. 71:4546–4553) were recorded at 600 MHz on a Varian Unity Inova NMR spectrometer equipped with a $^1$H/$^{13}$C/$^{15}$N triple resonance probe with a self-shielded triple-axis gradient coil using standard pulse sequences from the Varian user library. The operating temperature was set to 27° C. For each phase sensitive two-dimensional NMR spectrum 512 t$_1$ increments were acquired each with 2048 or 4096 real data points according to the TPPI-States method (Marion et al. (1989) J. Magn. Reson. 85:393–399). Spectral widths of 6983 Hz in both dimensions were used, with the carrier placed exactly on the water resonance which was attenuated by using either saturation between scans for 1.5 seconds or selective excitation by a gradient-tailored excitation pulse sequence (WATERGATE, Piotto et al. (1992) J. Biomol. NMR 2:661–665). DQFCOSY spectra were recorded using a gradient enhanced version applying magic-angle gradients (Mattiello et al. (1996) J. Am. Chem. Soc. 118:3253–3261). For TOCSY spectra mixing times between 30 and 80 ms were used and for NOESY mixing times between 50 and 200 ms.

The processing of the two-dimensional NMR spectra was performed using the software package Xwinnmr (version 2.5, NMR processing software from Bruker Analytische Messtechnik GmbH, D-76275 Ettlingen, Germany). Each dimension was processed with shifted sine-bell apodization and zero-filling performed once in each dimension. Baseline corrections were applied if necessary using Xwinnmr standard procedures.

The spectral assignment, cross peak integration, sequence specific assignment, stereo specific assignment, and all other bookkeeping were performed using the program PRONTO (PRONTO Software Development and Distribution, Copenhagen Denmark) (Kjær et al. (1991) NATO ASI Series (Hoch, J. C., Redfield C., & Poulsen, F. M., Eds.) Plenum, New York). Chemical shifts are measured in ppm and the water resonance set to 4.75 ppm.

Structure calculations. Distance restraints for the subsequent structure calculation were obtained from integrated NOESY cross peaks classified as either weak, medium or strong corresponding to upper distance restraints of 5.5, 3.3, and 2.7 Å, respectively. For distance restraints involving methyl groups, an additional 0.5 Å was added to the upper limit (Wagner et al. (1985) J. Mol. Biol. 196:611–639). Structure calculations were performed using the hybrid method combining distance geometry (Crippen et al. (1988) Distance Geometry and Molecular Conformation, Research Studies Press, Taunton, Somerset, England; Kuszewski et al. (1992) J. Biomol NMR 2:33–56) and simulated annealing based on the ideas of Nilges et al. (1988) FEBS Lett. 229:317–324 using X-PLOR 3.0 (Brünger (1992) X-PLOR Version 3.1: A System for X-ray Crystallography and NMR, Yale University Press, New Haven) according to the examples given by the X-PLOR manual (dg_sub_embed.inp, dgsa.inp, refine.inp). Residue numbers are derived from standard insulin residue numbering, residues in the B-chain are numbered B1–B29, residues in the C-peptide (e. g. MetTrpLys) are numbered C1–C3 and residues in the A-chain are numbered A1–A21.

Spectral assignment of the NMR spectra followed for most resonances the standard sequential assignment procedure described by Wüthrich (1986 NMR of Proteins and Nucleic Acids, Wiley, New York). The standard assignment procedure fails when the amid proton of a particular amino acid residue exchanges to rapidly with protons in the water. At pH 8.0 this occurs for several amino acid residues, however, comparison with earlier mutant insulin NMR spectral assignments and identification of neighbouring (in space) amino acid residues through NOEs allow an almost total spectral assignment. Analysis of the NOESY spectra showed that several amino acid residues had a NOE network to the surrounding residues similar to what has previously been determined for other insulin molecules, i.e., human insulin His$^{B16}$ mutant (Ludvigsen et al. (1994) Biochemistry 33:7998–8006) and these similar connections are found for residues B1–B10, B13–B14, B17–B24 and A4–A21. Additionally the dihedral angle restraints for the above listed residues were adopted from those used previously (Ludvigsen et al. (1994) supra).

Figure 5:
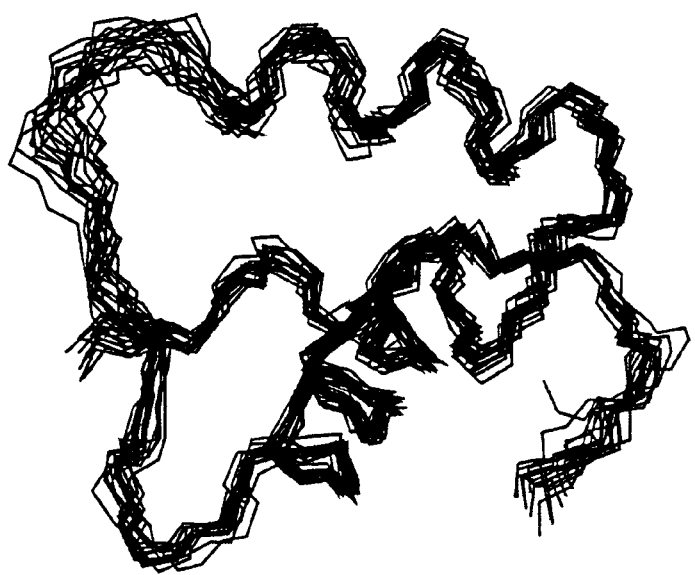
FIG. 5 shows the solution structures of Asp$^{B28}$IP (MetTrpLys) as backbone lines of ensemble of 20 converged structures.

Several amino acids in particular B27–B29, C1–C3, A1–A3 have cross peaks patterns which are consistent with peptide chains that are less well ordered than commonly well-defined secondary structural elements. Thus additional NOEs were converted into distance restraints without any further classification than upper limits of 5.5 Å or 6.0 Å if a methyl group were included. An ensemble of 20 converged structures (FIG. 5) was calculated and the relevant parameters listed in Table 3 for the converged structures. Each NOE here identical to a distance restraint is only counted once even though it might occur several times in the NOESY spectrum. Ramachandran plot quality assessment is standard quality parameters to evaluate local geometry quality. In general the described quality parameters are comparable to 2.5 Å resolution of X-ray based protein structures (Laskowski et al. (1996) J. Biol-mol.NMR 8:477–486).

TABLE 3

| Structurea quality assessment | | Asp$^{B28}$IP(MetTrpLys) |
|---|---|---|
| Number of NOEs | Total | 742 |
| | Intra | 319 |
| | short range (within 5 residue positions away but not intra NOEs) | 270 |
| | long range (more than 5 residue positions away) | 153 |
| Violations of NOEs >0.4 Å (average for 20 structures) | | 0 |
| RMS of NOE violations | | 0.013(±0.002) Å |
| RMS of dihedral angle restraints | | 0.30(±0.08)° |
| Deviations from ideal geometry | Impropers | 0.28(±0.02)° |
| | Angles | 0.38(±0.02)° |
| | Bonds | 0.0031(±0.0002) Å |
| Ramachandran Plot (Laskowski 1996) | Favoured regions | 77.2% |
| | additional allowed regions | 19.8% |
| | generously allowed regions | 2.6% |
| | disallowed regions | 0.4% |

Description of the Calculated Structure

Figure 6:
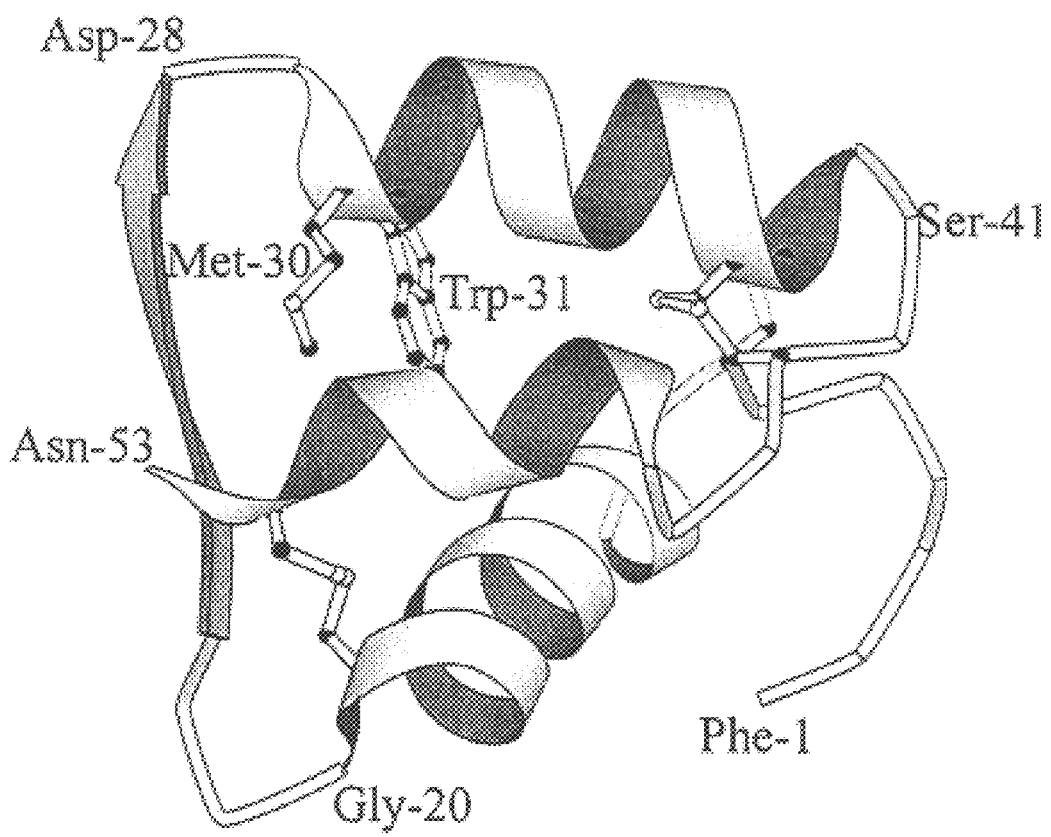
FIG. 6 shows a ribbon presentation of Asp$^{B28}$IP (MetTrpLys). The figure is produced using MOLSCRIPT (Kraulis (1991) J. Appl. Crystallog. 24:946–950). Amino acid residue annotations are derived as follows: B1–B29 (B chain) are numbered 1–29, residues C1–C3 (connecting peptide) are numbered 30–32, and residues A1–A21 (A chain) are numbered 33–53.

A representative structure most resembling the average of the ensemble is displayed in FIG. 6. Asp$^{B28}$IP(MetTrpLys) is structurally similar to the native insulin structure for regions comprising residues B1–B10, B14–B23, A4–A21. The differences are mostly pronounced for regions in the vicinity of the connecting peptide in positions B26–B29, C1–C3, A1–A3 and less pronounced for residues B11–B13. The structure of Asp$^{B28}$IP(MetTrpLys) near the C-peptide is strikingly different from the native like structure (Ludvigsen (1994) supra). The methionine and tryptophan side-chains in Asp$^{B28}$IP(MetTrpLys) opens the traditional insulin core structure by moving on one side the side-chains of particular Tyr$^{B26}$ and Phe$^{B25}$ away and leaving the otherwise usual neighboring hydrophobic patch comprised by the side-chains of Leu$^{B11}$, Val$^{B12}$, Ile$^{A2}$ and Tyr$^{A19}$ intact. This pocket created by moving Phe$^{B25}$, Tyr$^{B26}$ and the peptide chain comprised by residues B25 to B29 is apparently well suited to accommodate the packing of the side-chains Met$^{C1}$ and Trp$^{C2}$ from the C-peptide. Several NOEs from these two side-chains to structurally neighboring residues verify this very new arrangement of side-chains not previously observed in any insulin structure. Met$^{C1}$ is placed in a pocket composed by the residues Leu$^{B15}$, Phe$^{B24}$, Tyr$^{B26}$, Trp$^{C1}$, Ile$^{A2}$ and Tyr$^{A19}$ which all have NOEs to Met$^{C1}$. Trp$^{C2}$ has an even more extensive NOE network, but due to fast exchange of the indole amid proton only four resonances belonging to the aromatic ring system of Trp$^{C2}$ can be assigned. Despite this 21 inter-residue NOEs between Trp$^{C2}$ and its neighbors spanned by Leu$^{B11}$, Val$^{B12}$, Leu$^{B15}$, Tyr$^{B26}$, Met$^{C1}$ and Ile$^{A2}$ have been observed in the NOESY spectrum of Asp$^{B28}$IP(Met Trp Lys).

Figure 7:
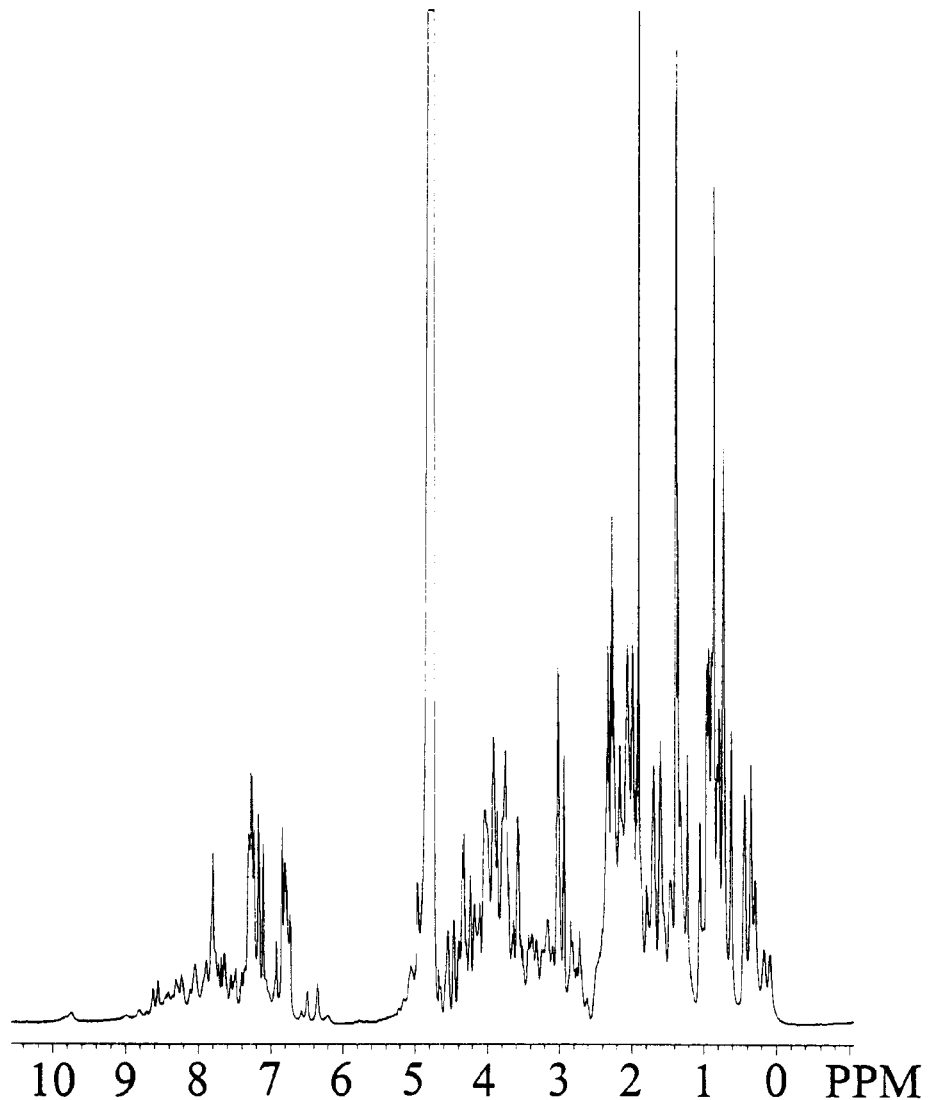
FIG. 7 is the ID proton NMR spectrum for Asp$^{B28}$IP (MetTrpLys) recorded at 27° C. at 1.0 mM concentration in 10%/90% D$_2$O/H$_2$O with 10 mM phosphate buffer at pH 8.0.

The presence of a tryptophan side-chain in the pocket also has extensive impact on the chemical shifts observed in the spectra of Asp$^{B28}$IP(Met Trp Lys). Under the conditions used for NMR the spectra of Asp$^{B28}$IP(Met Trp Lys) are influenced by some degree of self-association (FIG. 7) but the exchange between monomer and dimer is on the timescale of NMR only observed as an average between the two states. Between concentrations of 25 μM and 0.2 mM the degree of self-association does not change as seen by NMR.

Table 4 shows chemical shifts of Asp$^{B28}$IP(MetTrpLys) at 27° Celcius obtained at 600 MHz, pH 8 in 10%/90% D$_2$O/H$_2$O with 10 mM phosphate buffer. Chemical shifts are referenced by setting the residual water signal to 4.75 ppm. N/A means no assignment. Asp$^{B28}$IP(MetTrpLys) assignments (1–29=B1–B29; 30–32=C1–C3 and 33–53=A1–A21) and Table 5 provides the atomic coordinates of Asp$^{B28}$IP(MetTrpLys) in PDB format.

TABLE 4

NMR spectral assignments for Asp$^{B28}$IP(MetTrpLys)

| Spin system | MN | HA | Other: |
|---|---|---|---|
| Phe-1 | | 4.52 | HB#a: 2.976, HB#b: 3.040, HD#: 7.104, HE#: 7.214, HZ: 7.177 |
| Val-2 | N/A | N/A | HB: N/A, HG#a: N/A, HG#b: N/A |
| Asn-3 | | N/A | HB#a: N/A, HB#b: N/A, HD2#a: N/A, HD2#b: N/A |
| Glu-4 | | N/A | HB#a: N/A, HB#b: N/A |
| His-5 | | 4.30 | HB#a: 3.311, HB#b: 2.992, HD2: 6.850, HE1: 7.605 |
| Leu-6 | | 4.47 | HB#a: 1.635, HB#b: 0.807, HG: 1.506, HB#a: 0.753, HD#b: 0.675 |
| Cys-7 | 8.30 | 4.83 | HB#a: 2.901, HB#b: 3.173 |
| Gly-8 | | N/A, N/A | |
| Ser-9 | | N/A | HB#: N/A |
| His-10 | N/A | 4.41 | HB#a: 3.140, HB#b: 3.351, HD2: 7.112, HE1: 7.729 |
| Leu-11 | N/A | 3.93 | HB#a: N/A, HB#b: 1.143, HG: 1.257, HD#a: 0.375, HD#b: 0.559 |
| Val-12 | 7.25 | 3.37 | HB: 2.000, HG#a: 0.849, HG#b: N/A |
| Glu-13 | N/A | N/A | HB#a: N/A, HD#a: N/A, HG#b: N/A |
| Ala-14 | 7.71 | 3.98 | HB#: 1.307 |
| Leu-15 | 7.83 | 3.74 | HB#a: 0.871, HB#b: 1.254, HG: 1.157, HD#a: N/A, HD#b: 0.295 |
| Tyr-16 | 8.15 | 4.31 | HB#a: 3.115, HD: 7.204, HE#: 6.734 |
| Leu-17 | 7.99 | 4.05 | HB#a: 2.004, HB#b: 1.849, HG: 1.732, HD#a: 0.900, HD#b: 0.879 |
| Val-18 | 8.49 | 3.71 | HB: 1.996, HG#a: 0.994, HG#b: 0.834 |
| Cys-19 | 8.57 | 4.81 | HB#a: 2.820, HB#b: 3.250 |
| Gly-20 | 7.75 | 3.96, N/A | |
| Arg-22 | N/A | N/A | HB#a: N/A, HB#b: N/A, HG#a: N/A, HG#b: N/A, HD#a: N/A, HD#b: N/A |
| Gly-23 | 7.12 | 4.06, 3.76 | |
| Phe-24 | 7.56 | 4.99 | HB#a: 2.971, HB#b: 3.206, HD#: 6.746, HE#: 6.877, HZ: N/A |
| Phe-25 | N/A | 4.78 | HB#a: 3.051, HB#b: N/A, HD#: 7.172, HE#: 7.249 |
| Tyr-26 | N/A | 4.63 | HB#a: 2.770, HB#b: N/A, HD#: 6.894, HE#: 6.291 |
| Thr-27 | N/A | N/A | HB: N/A, HG#2: N/A |

TABLE 4-continued

NMR spectral assignments for Asp$^{B28}$IP(MetTrpLys)

| Spin system | MN | HA | Other: |
|---|---|---|---|
| Asp-28 | N/A | N/A | HB#a: N/A, HB#b: N/A |
| Lys-29 | | | |
| Met-30 | 7.84 | 4.18 | HB#: 2.627, HG#: 2.904, HE#: 2.110 |
| Trp-31 | | 4.19 | HB#a: 3.182, HE3: 7.037, HH2: 6.763, HZ2: 7.147, HZ3: 6.437 |
| Lys-32 | | | |
| Gly-33 | | N/A, N/A | |
| Ile-34 | 7.98 | 3.53 | HB: 0.953, HG1#a: 0.382, HG1#b: 0.562, HG2#: 0.234, HD#: 0.029 |
| Val-35 | 7.75 | N/A, 4.00 | HB: N/A, HB: 1.925, HG#a: N/A, HG#b: N/A, HG#b: 0.807 |
| Glu-36 | N/A | N/A | HB#a: N/A, HG#a: N/A |
| Gln-37 | 7.73 | 3.96 | HB#: 2.033, HG#: 2.313 |
| Cys-38 | 8.24 | 4.89 | HB#a: 3.103, HB#b: 2.700 |
| Cys-39 | N/A | N/A | HB#a: N/A, HB#b: N/A |
| Thr-40 | | 3.95 | HB: 4.411, HG2#: 1.167 |
| Ser-41 | 6.97 | 4.59 | HB#a: 3.698, HB#b: 3.867 |
| Ile-42 | 7.59 | 4.32 | HB: 1.399, HG1#a: N/A, HG2#: 0.573, HD#: 0.389 |
| Cys-43 | N/A | N/A | HB#a: N/A |
| Ser-44 | N/A | N/A | HB#a: N/A, HB#b: N/A |
| Leu-45 | | 3.86 | HB#a: 1.412, HB#b: 1.489, HG: 1.565, HD#a: 0.808, HD#b: 0.733 |
| Tyr-46 | 7.59 | 4.27 | HB#a: 2.938, HD#: 7.049, HE#: 6.784 |
| Gln-47 | 7.49 | 3.87 | HB#a: 2.235, HB#b: 1.948, HG#a: 2.305, HG#b: 2.076 |
| Leu-48 | 7.66 | 4.11 | HB#a: 1.930, HB#b: 1.409, HG: 1.683, HD#a: 0.677, HD#b: N/A |
| Glu-49 | 7.75 | 4.12 | HB#a: N/A, HB#b: 1.935, HG#a: 2.291, HG#b: 2.191 |
| Asn-50 | 7.21 | 4.34 | HB#a: 2.363, HB#b: N/A |
| Tyr-51 | 7.78 | 4.50 | HB#a: 3.269, HB#b: 2.774, HD#: 7.250, HE#: 6.670 |
| Cys-52 | 7.35 | 5.01 | HB#a: 2.765, HB#b: 3.322 |
| Asn-53 | 8.18 | 4.40 | HB#a: 2.555, EB#b: 2.716, HD2#a: 7.426, HD2#b: N/A |

TABLE 5

Atomic coordinates of Asp$^{28}$IP(MetTrpLys) in PDB format

| ATOM | 1 | CA | PHE | 1 | −6.075 | −6.762 | −0.761 | 1.00 | 0.00 |
|---|---|---|---|---|---|---|---|---|---|
| ATOM | 2 | HA | PHE | 1 | −5.526 | −6.571 | −0.150 | 1.00 | 0.00 |
| ATOM | 3 | CB | PHE | 1 | −5.359 | −6.093 | −1.942 | 1.00 | 0.00 |
| ATOM | 4 | HB1 | PHE | 1 | −5.934 | −6.258 | −2.842 | 1.00 | 0.00 |
| ATOM | 5 | HB2 | PHE | 1 | −4.382 | −6.535 | −2.061 | 1.00 | 0.00 |
| ATOM | 6 | CG | PHE | 1 | −5.208 | −4.597 | −1.715 | 1.00 | 0.00 |
| ATOM | 7 | CD1 | PHE | 1 | −4.925 | −4.081 | −0.436 | 1.00 | 0.00 |
| ATOM | 8 | HD1 | PHE | 1 | −4.817 | −4.749 | 0.405 | 1.00 | 0.00 |
| ATOM | 9 | CD2 | PHE | 1 | −5.346 | −3.722 | −2.799 | 1.00 | 0.00 |
| ATOM | 10 | HD2 | PHE | 1 | −5.563 | −4.112 | −3.783 | 1.00 | 0.00 |
| ATOM | 11 | CE1 | PHE | 1 | −4.787 | −2.702 | −0.251 | 1.00 | 0.00 |
| ATOM | 12 | HE1 | PHE | 1 | −4.573 | −2.308 | 0.732 | 1.00 | 0.00 |
| ATOM | 13 | CE2 | PHE | 1 | −5.204 | −2.341 | −2.612 | 1.00 | 0.00 |
| ATOM | 14 | HE2 | PHE | 1 | −5.310 | −1.668 | −3.451 | 1.00 | 0.00 |
| ATOM | 15 | CZ | PHE | 1 | −4.926 | −1.831 | −1.338 | 1.00 | 0.00 |
| ATOM | 16 | HZ | PHE | 1 | −4.818 | −0.768 | −1.195 | 1.00 | 0.00 |
| ATOM | 17 | C | PHE | 1 | −7.491 | −6.201 | −0.628 | 1.00 | 0.00 |
| ATOM | 18 | O | PHE | 1 | −8.361 | −6.497 | −1.425 | 1.00 | 0.00 |
| ATOM | 19 | N | PHE | 1 | −6.144 | −8.234 | −0.995 | 1.00 | 0.00 |
| ATOM | 20 | HT1 | PHE | 1 | −6.303 | −8.723 | −0.091 | 1.00 | 0.00 |
| ATOM | 21 | HT2 | PHE | 1 | −5.250 | −8.560 | −1.415 | 1.00 | 0.00 |
| ATOM | 22 | HT3 | PHE | 1 | −6.930 | −8.446 | −1.642 | 1.00 | 0.00 |
| ATOM | 23 | N | VAL | 2 | −7.730 | −5.399 | 0.380 | 1.00 | 0.00 |
| ATOM | 24 | HN | VAL | 2 | −7.013 | −5.181 | 1.011 | 1.00 | 0.00 |
| ATOM | 25 | CA | VAL | 2 | −9.095 | −4.819 | 0.578 | 1.00 | 0.00 |
| ATOM | 26 | HA | VAL | 2 | −9.838 | −5.571 | 0.354 | 1.00 | 0.00 |
| ATOM | 27 | CE | VAL | 2 | −9.270 | −4.345 | 2.030 | 1.00 | 0.00 |
| ATOM | 28 | HB | VAL | 2 | −8.787 | −3.387 | 2.154 | 1.00 | 0.00 |
| ATOM | 29 | CG1 | VAL | 2 | −10.760 | −4.206 | 2.339 | 1.00 | 0.00 |
| ATOM | 30 | HG11 | VAL | 2 | −11.281 | −3.863 | 1.457 | 1.00 | 0.00 |
| ATOM | 31 | HG12 | VAL | 2 | −10.897 | −3.493 | 3.139 | 1.00 | 0.00 |
| ATOM | 32 | HG13 | VAL | 2 | −11.156 | −5.164 | 2.641 | 1.00 | 0.00 |
| ATOM | 33 | CG2 | VAL | 2 | −8.653 | −5.362 | 3.001 | 1.00 | 0.00 |
| ATOM | 34 | HG21 | VAL | 2 | −8.836 | −6.363 | 2.637 | 1.00 | 0.00 |
| ATOM | 35 | HG22 | VAL | 2 | −9.103 | −5.245 | 3.976 | 1.00 | 0.00 |
| ATOM | 36 | HG23 | VAL | 2 | −7.589 | −5.193 | 3.071 | 1.00 | 0.00 |
| ATOM | 37 | C | VAL | 2 | −9.279 | −3.628 | −0.369 | 1.00 | 0.00 |
| ATOM | 38 | O | VAL | 2 | −8.349 | −2.892 | −0.637 | 1.00 | 0.00 |
| ATOM | 39 | N | ASN | 3 | −10.473 | −3.437 | −0.874 | 1.00 | 0.00 |
| ATOM | 40 | HN | ASN | 3 | −11.204 | −4.045 | −0.641 | 1.00 | 0.00 |
| ATOM | 41 | CA | ASN | 3 | −10.725 | −2.296 | −1.806 | 1.00 | 0.00 |

TABLE 5-continued

Atomic coordinates of Asp$^{28}$IP(MetTrpLys) in PDB format

| ATOM | 42 | HA | ASN | 3 | −9.782 | −1.927 | −2.184 | 1.00 | 0.00 |
|---|---|---|---|---|---|---|---|---|---|
| ATOM | 43 | CB | ASN | 3 | −11.594 | −2.772 | −2.975 | 1.00 | 0.00 |
| ATOM | 44 | HB1 | ASN | 3 | −12.168 | −1.940 | −3.357 | 1.00 | 0.00 |
| ATOM | 45 | HB2 | ASN | 3 | −12.265 | −3.545 | −2.633 | 1.00 | 0.00 |
| ATOM | 46 | CG | ASN | 3 | −10.702 | −3.324 | −4.087 | 1.00 | 0.00 |
| ATOM | 47 | OD1 | ASN | 3 | −9.628 | −3.832 | −3.824 | 1.00 | 0.00 |
| ATOM | 48 | ND2 | ASN | 3 | −11.103 | −3.251 | −5.327 | 1.00 | 0.00 |
| ATOM | 49 | HD21 | ASN | 3 | −11.968 | −2.842 | −5.538 | 1.00 | 0.00 |
| ATOM | 50 | HD22 | ASN | 3 | −10.539 | −3.603 | −6.046 | 1.00 | 0.00 |
| ATOM | 51 | C | ASN | 3 | −11.448 | −1.171 | −1.055 | 1.00 | 0.00 |
| ATOM | 52 | O | ASN | 3 | −12.648 | −1.002 | −1.182 | 1.00 | 0.00 |
| ATOM | 53 | N | GLN | 4 | −10.727 | −0.404 | −0.276 | 1.00 | 0.00 |
| ATOM | 54 | HN | GLN | 4 | −9.763 | −0.562 | −0.193 | 1.00 | 0.00 |
| ATOM | 55 | CA | GLN | 4 | −11.370 | 0.711 | 0.484 | 1.00 | 0.00 |
| ATOM | 56 | HA | GLN | 4 | −12.282 | 1.008 | −0.011 | 1.00 | 0.00 |
| ATOM | 57 | CB | GLN | 4 | −11.690 | 0.260 | 1.917 | 1.00 | 0.00 |
| ATOM | 58 | HB1 | GLN | 4 | −12.381 | 0.958 | 2.365 | 1.00 | 0.00 |
| ATOM | 59 | HB2 | GLN | 4 | −10.779 | 0.237 | 2.498 | 1.00 | 0.00 |
| ATOM | 60 | CG | GLN | 4 | −12.318 | −1.136 | 1.905 | 1.00 | 0.00 |
| ATOM | 61 | HG1 | GLN | 4 | −11.533 | −1.879 | 1.890 | 1.00 | 0.00 |
| ATOM | 62 | HG2 | GLN | 4 | −12.936 | −1.245 | 1.028 | 1.00 | 0.00 |
| ATOM | 63 | CD | GLN | 4 | −13.173 | −1.325 | 3.160 | 1.00 | 0.00 |
| ATOM | 64 | OE1 | GLN | 4 | −13.712 | −0.374 | 3.692 | 1.00 | 0.00 |
| ATOM | 65 | NE2 | GLN | 4 | −13.323 | −2.522 | 3.660 | 1.00 | 0.00 |
| ATOM | 66 | HE21 | GLN | 4 | −12.892 | −3.289 | 3.231 | 1.00 | 0.00 |
| ATOM | 67 | HE22 | GLN | 4 | −13.867 | −2.653 | 4.465 | 1.00 | 0.00 |
| ATOM | 68 | C | GLN | 4 | −10.410 | 1.903 | 0.543 | 1.00 | 0.00 |
| ATOM | 69 | O | GLN | 4 | −9.424 | 1.950 | −0.168 | 1.00 | 0.00 |
| ATOM | 70 | N | HIS | 5 | −10.690 | 2.857 | 1.392 | 1.00 | 0.00 |
| ATOM | 71 | HN | HIS | 5 | −11.488 | 2.787 | 1.958 | 1.00 | 0.00 |
| ATOM | 72 | CA | HIS | 5 | −9.799 | 4.044 | 1.516 | 1.00 | 0.00 |
| ATOM | 73 | HA | HIS | 5 | −9.334 | 4.246 | 0.562 | 1.00 | 0.00 |
| ATOM | 74 | CS | HIS | 5 | −10.622 | 5.258 | 1.951 | 1.00 | 0.00 |
| ATOM | 75 | HB1 | HIS | 5 | −9.995 | 6.137 | 1.964 | 1.00 | 0.00 |
| ATOM | 76 | HB2 | HIS | 5 | −11.024 | 5.087 | 2.939 | 1.00 | 0.00 |
| ATOM | 77 | CG | HIS | 5 | −11.749 | 5.459 | 0.974 | 1.00 | 0.00 |
| ATOM | 78 | ND1 | HIS | 5 | −12.883 | 4.665 | 0.982 | 1.00 | 0.00 |
| ATOM | 79 | HD1 | HIS | 5 | −13.076 | 3.934 | 1.608 | 1.00 | 0.00 |
| ATOM | 80 | CD2 | HIS | 5 | −11.918 | 6.343 | −0.064 | 1.00 | 0.00 |
| ATOM | 81 | HD2 | HIS | 5 | −11.211 | 7.103 | −0.355 | 1.00 | 0.00 |
| ATOM | 82 | CE1 | HIS | 5 | −13.677 | 5.080 | −0.021 | 1.00 | 0.00 |
| ATOM | 83 | HE1 | HIS | 5 | −14.629 | 4.635 | −0.264 | 1.00 | 0.00 |
| ATOM | 84 | NE2 | HIS | 5 | −13.136 | 6.102 | −0.690 | 1.00 | 0.00 |
| ATOM | 85 | C | HIS | 5 | −8.718 | 3.742 | 2.554 | 1.00 | 0.00 |
| ATOM | 86 | O | HIS | 5 | −9.006 | 3.446 | 3.697 | 1.00 | 0.00 |
| ATOM | 87 | N | LEU | 6 | −7.475 | 3.794 | 2.152 | 1.00 | 0.00 |
| ATOM | 88 | HN | LEU | 6 | −7.277 | 4.020 | 1.219 | 1.00 | 0.00 |
| ATOM | 89 | CA | LEU | 6 | −6.360 | 3.485 | 3.093 | 1.00 | 0.00 |
| ATOM | 90 | HA | LEU | 6 | −6.687 | 2.754 | 3.815 | 1.00 | 0.00 |
| ATOM | 91 | CS | LEU | 6 | −5.180 | 2.923 | 2.298 | 1.00 | 0.00 |
| ATOM | 92 | HB1 | LEU | 6 | −4.416 | 2.580 | 2.979 | 1.00 | 0.00 |
| ATOM | 93 | HB2 | LEU | 6 | −4.776 | 3.705 | 1.667 | 1.00 | 0.00 |
| ATOM | 94 | CG | LEU | 6 | −5.654 | 1.752 | 1.428 | 1.00 | 0.00 |
| ATOM | 95 | HO | LEU | 6 | −6.504 | 2.065 | 0.841 | 1.00 | 0.00 |
| ATOM | 96 | CD1 | LEU | 6 | −4.523 | 1.318 | 0.486 | 1.00 | 0.00 |
| ATOM | 97 | HD11 | LEU | 6 | −3.801 | 2.116 | 0.395 | 1.00 | 0.00 |
| ATOM | 98 | HD12 | LEU | 6 | −4.935 | 1.094 | −0.487 | 1.00 | 0.00 |
| ATOM | 99 | HD13 | LEU | 6 | −4.039 | 0.437 | 0.881 | 1.00 | 0.00 |
| ATOM | 100 | CD2 | LEU | 6 | −6.058 | 0.574 | 2.328 | 1.00 | 0.00 |
| ATOM | 101 | HD21 | LEU | 6 | −5.710 | −0.352 | 1.892 | 1.00 | 0.00 |
| ATOM | 102 | HD22 | LEU | 6 | −7.136 | 0.544 | 2.417 | 1.00 | 0.00 |
| ATOM | 103 | HD23 | LEU | 6 | −5.621 | 0.699 | 3.308 | 1.00 | 0.00 |
| ATOM | 104 | C | LEU | 6 | −5.912 | 4.757 | 3.814 | 1.00 | 0.00 |
| ATOM | 105 | O | LEU | 6 | −5.356 | 5.654 | 3.213 | 1.00 | 0.00 |
| ATOM | 106 | N | CYS | 7 | −6.143 | 4.833 | 5.101 | 1.00 | 0.00 |
| ATOM | 107 | HN | CYS | 7 | −6.585 | 4.090 | 5.563 | 1.00 | 0.00 |
| ATOM | 108 | CA | CYS | 7 | −5.721 | 6.041 | 5.870 | 1.00 | 0.00 |
| ATOM | 109 | HA | CYS | 7 | −4.835 | 6.453 | 5.422 | 1.00 | 0.00 |
| ATOM | 110 | HB1 | CYS | 7 | −7.133 | 7.322 | 6.855 | 1.00 | 0.00 |
| ATOM | 111 | HB2 | CYS | 7 | −7.695 | 6.688 | 5.314 | 1.00 | 0.00 |
| ATOM | 112 | C | CYS | 7 | −5.408 | 5.640 | 7.314 | 1.00 | 0.00 |
| ATOM | 113 | O | CYS | 7 | −6.280 | 5.231 | 8.058 | 1.00 | 0.00 |
| ATOM | 114 | CB | CYS | 7 | −6.844 | 7.087 | 5.846 | 1.00 | 0.00 |
| ATOM | 115 | SG | CYS | 7 | −6.272 | 8.597 | 5.019 | 1.00 | 0.00 |
| ATOM | 116 | N | GLY | 8 | −4.167 | 5.760 | 7.712 | 1.00 | 0.00 |
| ATOM | 117 | HN | GLY | 8 | −3.488 | 6.094 | 7.090 | 1.00 | 0.00 |
| ATOM | 118 | CA | GLY | 8 | −3.781 | 5.394 | 9.105 | 1.00 | 0.00 |

TABLE 5-continued

Atomic coordinates of Asp²⁸IP(MetTrpLys) in PDB format

| ATOM | 119 | HA1 | GLY | 8 | −4.671 | 5.213 | 9.690 | 1.00 | 0.00 |
|---|---|---|---|---|---|---|---|---|---|
| ATOM | 120 | HA2 | GLY | 8 | −3.219 | 6.205 | 9.546 | 1.00 | 0.00 |
| ATOM | 121 | C | GLY | 8 | −2.923 | 4.129 | 9.095 | 1.00 | 0.00 |
| ATOM | 122 | O | GLY | 8 | −1.949 | 4.041 | 8.360 | 1.00 | 0.00 |
| ATOM | 123 | N | SER | 9 | −3.278 | 3.150 | 9.877 | 1.00 | 0.00 |
| ATOM | 124 | HN | HER | 9 | −4.068 | 3.251 | 10.451 | 1.00 | 0.00 |
| ATOM | 125 | CA | SER | 9 | −2.490 | 1.883 | 9.916 | 1.00 | 0.00 |
| ATOM | 126 | HA | SER | 9 | −1.437 | 2.116 | 9.986 | 1.00 | 0.00 |
| ATOM | 127 | CB | HER | 9 | −2.912 | 1.063 | 11.135 | 1.00 | 0.00 |
| ATOM | 128 | HB1 | SER | 9 | −3.777 | 0.464 | 10.881 | 1.00 | 0.00 |
| ATOM | 129 | HB2 | HER | 9 | −3.164 | 1.724 | 11.947 | 1.00 | 0.00 |
| ATOM | 130 | OG | SER | 9 | −1.837 | 0.222 | 11.531 | 1.00 | 0.00 |
| ATOM | 131 | HG | SER | 9 | −1.789 | −0.510 | 10.913 | 1.00 | 0.00 |
| ATOM | 132 | C | SER | 9 | −2.751 | 1.076 | 8.643 | 1.00 | 0.00 |
| ATOM | 133 | O | SER | 9 | −1.897 | 0.350 | 8.173 | 1.00 | 0.00 |
| ATOM | 134 | N | HIS | 10 | −3.929 | 1.197 | 8.088 | 1.00 | 0.00 |
| ATOM | 135 | HN | HIS | 10 | −4.599 | 1.790 | 8.489 | 1.00 | 0.00 |
| ATOM | 136 | CA | HIS | 10 | −4.258 | 0.439 | 6.843 | 1.00 | 0.00 |
| ATOM | 137 | HA | HIS | 10 | −4.122 | −0.614 | 7.021 | 1.00 | 0.00 |
| ATOM | 138 | CB | HIS | 10 | −5.720 | 0.706 | 6.456 | 1.00 | 0.00 |
| ATOM | 139 | HB1 | HIS | 10 | −5.771 | 0.967 | 5.413 | 1.00 | 0.00 |
| ATOM | 140 | HB2 | HIS | 10 | −6.107 | 1.522 | 7.049 | 1.00 | 0.00 |
| ATOM | 141 | CG | HIS | 10 | −6.547 | −0.528 | 6.700 | 1.00 | 0.00 |
| ATOM | 142 | ND1 | HIS | 10 | −6.371 | −1.687 | 5.963 | 1.00 | 0.00 |
| ATOM | 143 | HD1 | HIS | 10 | −5.723 | −1.822 | 5.241 | 1.00 | 0.00 |
| ATOM | 144 | CD2 | HIS | 10 | −7.556 | −0.797 | 7.591 | 1.00 | 0.00 |
| ATOM | 145 | HD2 | HIS | 10 | −7.945 | −0.101 | 8.319 | 1.00 | 0.00 |
| ATOM | 146 | CE1 | HIS | 10 | −7.253 | −2.594 | 6.419 | 1.00 | 0.00 |
| ATOM | 147 | HE1 | HIS | 10 | −7.345 | −3.595 | 6.027 | 1.00 | 0.00 |
| ATOM | 148 | NE2 | HIS | 10 | −8.001 | −2.104 | 7.412 | 1.00 | 0.00 |
| ATOM | 149 | C | HIS | 10 | −3.332 | 0.880 | 5.701 | 1.00 | 0.00 |
| ATOM | 150 | O | HIS | 10 | −3.149 | 0.160 | 4.737 | 1.00 | 0.00 |
| ATOM | 151 | N | LEU | 11 | −2.755 | 2.052 | 5.797 | 1.00 | 0.00 |
| ATOM | 152 | HN | LEU | 11 | −2.922 | 2.619 | 6.578 | 1.00 | 0.00 |
| ATOM | 153 | CA | LEU | 11 | −1.851 | 2.536 | 4.713 | 1.00 | 0.00 |
| ATOM | 154 | HA | LEU | 11 | −2.384 | 2.534 | 3.774 | 1.00 | 0.00 |
| ATOM | 155 | CE | LEU | 11 | −1.392 | 3.961 | 5.031 | 1.00 | 0.00 |
| ATOM | 156 | HB1 | LEU | 11 | −0.726 | 3.942 | 5.880 | 1.00 | 0.00 |
| ATOM | 157 | HB2 | LEU | 11 | −2.253 | 4.572 | 5.261 | 1.00 | 0.00 |
| ATOM | 158 | CG | LEU | 11 | −0.658 | 4.543 | 3.823 | 1.00 | 0.00 |
| ATOM | 159 | HG | LEU | 11 | 0.144 | 3.879 | 3.533 | 1.00 | 0.00 |
| ATOM | 160 | CD1 | LEU | 11 | −1.635 | 4.701 | 2.655 | 1.00 | 0.00 |
| ATOM | 161 | HD11 | LEU | 11 | −2.565 | 5.114 | 3.017 | 1.00 | 0.00 |
| ATOM | 162 | HD12 | LEU | 11 | −1.821 | 3.735 | 2.209 | 1.00 | 0.00 |
| ATOM | 163 | HD13 | LEU | 11 | −1.209 | 5.362 | 1.916 | 1.00 | 0.00 |
| ATOM | 164 | CD2 | LEU | 11 | −0.082 | 5.912 | 4.194 | 1.00 | 0.00 |
| ATOM | 165 | HD21 | LEU | 11 | −0.855 | 6.660 | 4.114 | 1.00 | 0.00 |
| ATOM | 166 | HD22 | LEU | 11 | 0.727 | 6.156 | 3.522 | 1.00 | 0.00 |
| ATOM | 167 | HD23 | LEU | 11 | 0.288 | 5.883 | 5.207 | 1.00 | 0.00 |
| ATOM | 168 | C | LEU | 11 | −0.628 | 1.620 | 4.604 | 1.00 | 0.00 |
| ATOM | 169 | O | LEU | 11 | −0.303 | 1.133 | 3.539 | 1.00 | 0.00 |
| ATOM | 170 | N | VAL | 12 | 0.055 | 1.390 | 5.699 | 1.00 | 0.00 |
| ATOM | 171 | HN | VAL | 12 | −0.226 | 1.800 | 6.543 | 1.00 | 0.00 |
| ATOM | 172 | CA | VAL | 12 | 1.265 | 0.514 | 5.663 | 1.00 | 0.00 |
| ATOM | 173 | HA | VAL | 12 | 1.903 | 0.819 | 4.847 | 1.00 | 0.00 |
| ATOM | 174 | CB | VAL | 12 | 2.033 | 0.651 | 6.981 | 1.00 | 0.00 |
| ATOM | 175 | HB | VAL | 12 | 1.442 | 0.243 | 7.787 | 1.00 | 0.00 |
| ATOM | 176 | CD1 | VAL | 12 | 3.356 | −0.110 | 6.883 | 1.00 | 0.00 |
| ATOM | 177 | HG11 | VAL | 12 | 3.936 | 0.059 | 7.777 | 1.00 | 0.00 |
| ATOM | 178 | HG12 | VAL | 12 | 3.909 | 0.239 | 6.023 | 1.00 | 0.00 |
| ATOM | 179 | HG13 | VAL | 12 | 3.157 | −1.167 | 6.778 | 1.00 | 0.00 |
| ATOM | 180 | CG2 | VAL | 12 | 2.321 | 2.130 | 7.253 | 1.00 | 0.00 |
| ATOM | 181 | HG21 | VAL | 12 | 2.917 | 2.534 | 6.446 | 1.00 | 0.00 |
| ATOM | 182 | HG22 | VAL | 12 | 2.862 | 2.225 | 8.182 | 1.00 | 0.00 |
| ATOM | 183 | HG23 | VAL | 12 | 1.390 | 2.673 | 7.322 | 1.00 | 0.00 |
| ATOM | 184 | C | VAL | 12 | 0.852 | −0.950 | 5.461 | 1.00 | 0.00 |
| ATOM | 185 | O | VAL | 12 | 1.637 | −1.764 | 5.009 | 1.00 | 0.00 |
| ATOM | 186 | N | GLU | 13 | −0.365 | −1.294 | 5.802 | 1.00 | 0.00 |
| ATOM | 187 | HN | GLU | 13 | −0.978 | −0.625 | 6.171 | 1.00 | 0.00 |
| ATOM | 188 | CA | GLU | 13 | −0.827 | −2.706 | 5.640 | 1.00 | 0.00 |
| ATOM | 189 | HA | GLU | 13 | −0.099 | −3.371 | 6.080 | 1.00 | 0.00 |
| ATOM | 190 | CB | GLU | 13 | −2.165 | −2.882 | 6.361 | 1.00 | 0.00 |
| ATOM | 191 | HB1 | GLU | 13 | −2.707 | −3.703 | 5.916 | 1.00 | 0.00 |
| ATOM | 192 | HB2 | GLU | 13 | −2.745 | −1.975 | 6.270 | 1.00 | 0.00 |
| ATOM | 193 | CG | GLU | 13 | −1.913 | −3.185 | 7.840 | 1.00 | 0.00 |
| ATOM | 194 | HD1 | GLU | 13 | −2.783 | −2.910 | 3.417 | 1.00 | 0.00 |
| ATOM | 195 | HG2 | GLU | 13 | −1.060 | −2.619 | 8.182 | 1.00 | 0.00 |

TABLE 5-continued

Atomic coordinates of Asp[28]IP(MetTrpLys) in PDB format

| ATOM | 196 | CD   | GLU | 13 | −1.638 | −4.680 | 8.016  | 1.00 | 0.00 |
|------|-----|------|-----|----|--------|--------|--------|------|------|
| ATOM | 197 | OE1  | GLU | 13 | −2.032 | −5.217 | 9.038  | 1.00 | 0.00 |
| ATOM | 198 | OE2  | GLU | 13 | −1.036 | −5.261 | 7.128  | 1.00 | 0.00 |
| ATOM | 199 | C    | GLU | 13 | −1.001 | −3.058 | 4.154  | 1.00 | 0.00 |
| ATOM | 200 | O    | GLU | 13 | −1.130 | −4.219 | 3.805  | 1.00 | 0.00 |
| ATOM | 201 | N    | ALA | 14 | −1.020 | −2.079 | 3.277  | 1.00 | 0.00 |
| ATOM | 202 | HN   | ALA | 14 | −0.923 | −1.151 | 3.574  | 1.00 | 0.00 |
| ATOM | 203 | CA   | ALA | 14 | −1.200 | −2.381 | 1.824  | 1.00 | 0.00 |
| ATOM | 204 | HA   | ALA | 14 | −1.699 | −3.333 | 1.714  | 1.00 | 0.00 |
| ATOM | 205 | CB   | ALA | 14 | −2.055 | −1.288 | 1.178  | 1.00 | 0.00 |
| ATOM | 206 | HB1  | ALA | 14 | −2.984 | −1.191 | 1.722  | 1.00 | 0.00 |
| ATOM | 207 | HB2  | ALA | 14 | −2.266 | −1.556 | 0.152  | 1.00 | 0.00 |
| ATOM | 208 | HB3  | ALA | 14 | −1.522 | −0.350 | 1.203  | 1.00 | 0.00 |
| ATOM | 209 | C    | ALA | 14 | 0.160  | −2.443 | 1.120  | 1.00 | 0.00 |
| ATOM | 210 | O    | ALA | 14 | 0.340  | −3.189 | 0.176  | 1.00 | 0.00 |
| ATOM | 211 | N    | LEU | 15 | 1.114  | −1.662 | 1.565  | 1.00 | 0.00 |
| ATOM | 212 | HN   | LEU | 15 | 0.943  | −1.065 | 2.324  | 1.00 | 0.00 |
| ATOM | 213 | CA   | LEU | 15 | 2.459  | −1.675 | 0.914  | 1.00 | 0.00 |
| ATOM | 214 | HA   | LEU | 15 | 2.338  | −1.551 | −0.153 | 1.00 | 0.00 |
| ATOM | 215 | CB   | LEU | 15 | 3.309  | −0.529 | 1.462  | 1.00 | 0.00 |
| ATOM | 216 | HB1  | LEU | 15 | 4.336  | −0.661 | 1.152  | 1.00 | 0.00 |
| ATOM | 217 | HB2  | LEU | 15 | 3.256  | −0.525 | 2.542  | 1.00 | 0.00 |
| ATOM | 218 | CG   | LEU | 15 | 2.785  | 0.801  | 0.921  | 1.00 | 0.00 |
| ATOM | 219 | HG   | LEU | 15 | 1.729  | 0.885  | 1.137  | 1.00 | 0.00 |
| ATOM | 220 | CD1  | LEU | 15 | 3.533  | 1.956  | 1.590  | 1.00 | 0.00 |
| ATOM | 221 | HD11 | LEU | 15 | 3.903  | 1.635  | 2.554  | 1.00 | 0.00 |
| ATOM | 222 | HD12 | LEU | 15 | 2.863  | 2.791  | 1.723  | 1.00 | 0.00 |
| ATOM | 223 | HD13 | LEU | 15 | 4.364  | 2.256  | 0.969  | 1.00 | 0.00 |
| ATOM | 224 | CD2  | LEU | 15 | 3.006  | 0.859  | −0.594 | 1.00 | 0.00 |
| ATOM | 225 | HD21 | LEU | 15 | 2.950  | 1.884  | −0.927 | 1.00 | 0.00 |
| ATOM | 226 | HD22 | LEU | 15 | 2.243  | 0.278  | −1.092 | 1.00 | 0.00 |
| ATOM | 227 | HD23 | LEU | 15 | 3.978  | 0.456  | −0.834 | 1.00 | 0.00 |
| ATOM | 228 | C    | LEU | 15 | 3.156  | −3.009 | 1.190  | 1.00 | 0.00 |
| ATOM | 229 | O    | LEU | 15 | 3.865  | −3.528 | 0.349  | 1.00 | 0.00 |
| ATOM | 230 | N    | TYR | 16 | 2.957  | −3.571 | 2.358  | 1.00 | 0.00 |
| ATOM | 231 | HN   | TYR | 16 | 2.378  | −3.135 | 3.018  | 1.00 | 0.00 |
| ATOM | 232 | CA   | TYR | 16 | 3.606  | −4.876 | 2.681  | 1.00 | 0.00 |
| ATOM | 233 | HA   | TYR | 16 | 4.609  | −4.869 | 2.277  | 1.00 | 0.00 |
| ATOM | 234 | CB   | TYR | 16 | 3.689  | −5.037 | 4.230  | 1.00 | 0.00 |
| ATOM | 235 | HB1  | TYR | 16 | 3.494  | −4.076 | 4.686  | 1.00 | 0.00 |
| ATOM | 236 | HB2  | TYR | 16 | 4.688  | −5.346 | 4.492  | 1.00 | 0.00 |
| ATOM | 237 | CG   | TYR | 16 | 2.704  | −6.057 | 4.783  | 1.00 | 0.00 |
| ATOM | 238 | CD1  | TYR | 16 | 3.181  | −7.209 | 5.421  | 1.00 | 0.00 |
| ATOM | 239 | HD1  | TYR | 16 | 4.244  | −7.371 | 5.517  | 1.00 | 0.00 |
| ATOM | 240 | CD2  | TYR | 16 | 1.324  | −5.846 | 4.659  | 1.00 | 0.00 |
| ATOM | 241 | HD2  | TYR | 16 | 0.954  | −4.960 | 4.166  | 1.00 | 0.00 |
| ATOM | 242 | CE1  | TYR | 16 | 2.282  | −8.150 | 5.934  | 1.00 | 0.00 |
| ATOM | 243 | HE1  | TYR | 16 | 2.651  | −9.038 | 6.425  | 1.00 | 0.00 |
| ATOM | 244 | CE2  | TYR | 16 | 0.423  | −6.790 | 5.171  | 1.00 | 0.00 |
| ATOM | 245 | HE2  | TYR | 16 | −0.640 | −6.628 | 5.076  | 1.00 | 0.00 |
| ATOM | 246 | CZ   | TYR | 16 | 0.902  | −7.941 | 5.809  | 1.00 | 0.00 |
| ATOM | 247 | OH   | TYR | 16 | 0.016  | −8.868 | 6.315  | 1.00 | 0.00 |
| ATOM | 248 | HH   | TYR | 16 | −0.479 | −8.451 | 7.024  | 1.00 | 0.00 |
| ATOM | 249 | C    | TYR | 16 | 2.815  | −6.006 | 1.997  | 1.00 | 0.00 |
| ATOM | 250 | O    | TYR | 16 | 3.363  | −7.026 | 1.626  | 1.00 | 0.00 |
| ATOM | 251 | N    | LEU | 17 | 1.531  | −5.816 | 1.825  | 1.00 | 0.00 |
| ATOM | 252 | HN   | LEU | 17 | 1.118  | −4.981 | 2.129  | 1.00 | 0.00 |
| ATOM | 253 | CA   | LEU | 17 | 0.691  | −6.853 | 1.160  | 1.00 | 0.00 |
| ATOM | 254 | HA   | LEU | 17 | 0.816  | −7.799 | 1.665  | 1.00 | 0.00 |
| ATOM | 255 | CB   | LEU | 17 | −0.778 | −6.421 | 1.227  | 1.00 | 0.00 |
| ATOM | 256 | HB1  | LEU | 17 | −0.897 | −5.483 | 0.705  | 1.00 | 0.00 |
| ATOM | 257 | HB2  | LEU | 17 | −1.068 | −6.295 | 2.260  | 1.00 | 0.00 |
| ATOM | 258 | CG   | LEU | 17 | −1.668 | −7.480 | 0.573  | 1.00 | 0.00 |
| ATOM | 259 | HG   | LEU | 17 | −1.242 | −7.773 | −0.377 | 1.00 | 0.00 |
| ATOM | 260 | CD1  | LEU | 17 | −1.767 | −8.704 | 1.484  | 1.00 | 0.00 |
| ATOM | 261 | HD11 | LEU | 17 | −2.581 | −9.332 | 1.154  | 1.00 | 0.00 |
| ATOM | 262 | HD12 | LEU | 17 | −1.950 | −8.384 | 2.499  | 1.00 | 0.00 |
| ATOM | 263 | HD13 | LEU | 17 | −0.844 | −9.260 | 1.442  | 1.00 | 0.00 |
| ATOM | 264 | CD2  | LEU | 17 | −3.064 | −6.898 | 0.350  | 1.00 | 0.00 |
| ATOM | 265 | HD21 | LEU | 17 | −3.522 | −7.382 | −0.499 | 1.00 | 0.00 |
| ATOM | 266 | HD22 | LEU | 17 | −2.985 | −5.838 | 0.163  | 1.00 | 0.00 |
| ATOM | 267 | HD23 | LEU | 17 | −3.668 | −7.065 | 1.228  | 1.00 | 0.00 |
| ATOM | 268 | C    | LEU | 17 | 1.128  | −6.987 | −0.302 | 1.00 | 0.00 |
| ATOM | 269 | O    | LEU | 17 | 1.024  | −8.044 | −0.897 | 1.00 | 0.00 |
| ATOM | 270 | N    | VAL | 18 | 1.614  | −5.919 | −0.883 | 1.00 | 0.00 |
| ATOM | 271 | HN   | VAL | 18 | 1.683  | −5.081 | −0.380 | 1.00 | 0.00 |
| ATOM | 272 | CA   | VAL | 18 | 2.059  | −5.966 | −2.306 | 1.00 | 0.00 |

TABLE 5-continued

Atomic coordinates of Asp[28]IP(MetTrpLys) in PDB format

| ATOM | 273 | HA   | VAL | 18 | 1.392  | −6.595  | −2.875 | 1.00 | 0.00 |
|------|-----|------|-----|----|--------|---------|--------|------|------|
| ATOM | 274 | CB   | VAL | 18 | 2.052  | −4.548  | −2.886 | 1.00 | 0.00 |
| ATOM | 275 | HB   | VAL | 18 | 2.802  | −3.954  | −2.382 | 1.00 | 0.00 |
| ATOM | 276 | CG1  | VAL | 18 | 2.375  | −4.606  | −4.380 | 1.00 | 0.00 |
| ATOM | 277 | HG11 | VAL | 18 | 1.457  | −4.614  | −4.947 | 1.00 | 0.00 |
| ATOM | 278 | HG12 | VAL | 18 | 2.939  | −5.504  | −4.594 | 1.00 | 0.00 |
| ATOM | 279 | HG13 | VAL | 18 | 2.961  | −3.741  | −4.656 | 1.00 | 0.00 |
| ATOM | 280 | CG2  | VAL | 18 | 0.674  | −3.907  | −2.683 | 1.00 | 0.00 |
| ATOM | 281 | HG21 | VAL | 18 | 0.117  | −4.466  | −1.943 | 1.00 | 0.00 |
| ATOM | 282 | HG22 | VAL | 18 | 0.131  | −3.910  | −3.617 | 1.00 | 0.00 |
| ATOM | 283 | HG23 | VAL | 18 | 0.799  | −2.889  | −2.345 | 1.00 | 0.00 |
| ATOM | 284 | C    | VAL | 18 | 3.480  | −6.523  | −2.376 | 1.00 | 0.00 |
| ATOM | 285 | O    | VAL | 18 | 3.801  | −7.325  | −3.233 | 1.00 | 0.00 |
| ATOM | 286 | N    | CYS | 19 | 4.334  | −6.086  | −1.490 | 1.00 | 0.00 |
| ATOM | 287 | HN   | CYS | 19 | 4.048  | −5.430  | −0.821 | 1.00 | 0.00 |
| ATOM | 288 | CA   | CYS | 19 | 5.746  | −6.566  | −1.501 | 1.00 | 0.00 |
| ATOM | 289 | HA   | CYS | 19 | 5.981  | −6.963  | −2.478 | 1.00 | 0.00 |
| ATOM | 290 | HB1  | CYS | 19 | 7.708  | −5.690  | −1.396 | 1.00 | 0.00 |
| ATOM | 291 | HB2  | CYS | 19 | 6.603  | −5.126  | −0.146 | 1.00 | 0.00 |
| ATOM | 292 | C    | CYS | 19 | 5.910  | −7.669  | −0.451 | 1.00 | 0.00 |
| ATOM | 293 | O    | CYS | 19 | 6.116  | −8.822  | −0.782 | 1.00 | 0.00 |
| ATOM | 294 | CB   | CYS | 19 | 6.693  | −5.394  | −1.186 | 1.00 | 0.00 |
| ATOM | 295 | SG   | CYS | 19 | 6.271  | −3.960  | −2.210 | 1.00 | 0.00 |
| ATOM | 296 | N    | GLY | 20 | 5.806  | −7.326  | 0.809  | 1.00 | 0.00 |
| ATOM | 297 | HN   | GLY | 20 | 5.629  | −6.392  | 1.048  | 1.00 | 0.00 |
| ATOM | 298 | CA   | GLY | 20 | 5.938  | −8.354  | 1.885  | 1.00 | 0.00 |
| ATOM | 299 | HA1  | GLY | 20 | 5.615  | −9.313  | 1.508  | 1.00 | 0.00 |
| ATOM | 300 | HA2  | GLY | 20 | 5.319  | −8.074  | 2.725  | 1.00 | 0.00 |
| ATOM | 301 | C    | GLY | 20 | 7.395  | −8.458  | 2.341  | 1.00 | 0.00 |
| ATOM | 302 | O    | GLY | 20 | 7.969  | −7.508  | 2.837  | 1.00 | 0.00 |
| ATOM | 303 | N    | GLU | 21 | 7.991  | −9.615  | 2.186  | 1.00 | 0.00 |
| ATOM | 304 | HN   | GLU | 21 | 7.499  | −10.364 | 1.789  | 1.00 | 0.00 |
| ATOM | 305 | CA   | GLU | 21 | 9.410  | −9.809  | 2.615  | 1.00 | 0.00 |
| ATOM | 306 | HA   | GLU | 21 | 9.482  | −9.667  | 3.684  | 1.00 | 0.00 |
| ATOM | 307 | CB   | GLU | 21 | 9.856  | −11.229 | 2.262  | 1.00 | 0.00 |
| ATOM | 308 | HB1  | GLU | 21 | 10.92  | −11.314 | 2.391  | 1.00 | 0.00 |
| ATOM | 309 | HB2  | GLU | 21 | 9.598  | −11.441 | 1.235  | 1.00 | 0.00 |
| ATOM | 310 | CG   | GLU | 21 | 9.154  | −12.227 | 3.183  | 1.00 | 0.00 |
| ATOM | 311 | HG1  | GLU | 21 | 8.975  | −13.149 | 2.647  | 1.00 | 0.00 |
| ATOM | 312 | HG2  | GLU | 21 | 8.212  | −11.813 | 3.513  | 1.00 | 0.00 |
| ATOM | 313 | CD   | GLU | 21 | 10.040 | −12.513 | 4.398  | 1.00 | 0.00 |
| ATOM | 314 | OE1  | GLU | 21 | 9.858  | −11.851 | 5.407  | 1.00 | 0.00 |
| ATOM | 315 | OE2  | GLU | 21 | 10.885 | −13.387 | 4.298  | 1.00 | 0.00 |
| ATOM | 316 | C    | GLU | 21 | 10.321 | −8.800  | 1.908  | 1.00 | 0.00 |
| ATOM | 317 | O    | GLU | 21 | 11.338 | −8.394  | 2.441  | 1.00 | 0.00 |
| ATOM | 318 | N    | ARG | 22 | 9.965  | −8.395  | 0.715  | 1.00 | 0.00 |
| ATOM | 319 | HN   | ARG | 22 | 9.141  | −8.739  | 0.310  | 1.00 | 0.00 |
| ATOM | 320 | CA   | ARG | 22 | 10.807 | −7.413  | −0.030 | 1.00 | 0.00 |
| ATOM | 321 | HA   | ARG | 22 | 11.805 | −7.809  | −0.145 | 1.00 | 0.00 |
| ATOM | 322 | CB   | ARG | 22 | 10.198 | −7.162  | −1.410 | 1.00 | 0.00 |
| ATOM | 323 | HH1  | ARG | 22 | 10.595 | −6.244  | −1.813 | 1.00 | 0.00 |
| ATOM | 324 | HH2  | ARG | 22 | 9.126  | −7.079  | −1.314 | 1.00 | 0.00 |
| ATOM | 325 | CG   | ARG | 22 | 10.537 | −8.329  | −2.351 | 1.00 | 0.00 |
| ATOM | 326 | HG1  | ARG | 22 | 9.626  | −8.727  | −2.767 | 1.00 | 0.00 |
| ATOM | 327 | HG2  | ARG | 22 | 11.050 | −9.104  | −1.801 | 1.00 | 0.00 |
| ATOM | 328 | CD   | ARG | 22 | 11.438 | −7.835  | −3.489 | 1.00 | 0.00 |
| ATOM | 329 | HD1  | ARG | 22 | 10.951 | −7.021  | −4.006 | 1.00 | 0.00 |
| ATOM | 330 | HD2  | ARG | 22 | 11.618 | −8.644  | −4.182 | 1.00 | 0.00 |
| ATOM | 331 | NE   | ARG | 22 | 12.735 | −7.363  | −2.928 | 1.00 | 0.00 |
| ATOM | 332 | HE   | ARG | 22 | 12.747 | −6.827  | −2.107 | 1.00 | 0.00 |
| ATOM | 333 | CZ   | ARG | 22 | 13.854 | −7.662  | −3.527 | 1.00 | 0.00 |
| ATOM | 334 | NH1  | ARG | 22 | 13.963 | −7.517  | −4.820 | 1.00 | 0.00 |
| ATOM | 335 | HB11 | ARG | 22 | 13.186 | −7.175  | −5.351 | 1.00 | 0.00 |
| ATOM | 336 | HB12 | ARG | 22 | 14.821 | −7.746  | −5.280 | 1.00 | 0.00 |
| ATOM | 337 | NH2  | ARG | 22 | 14.867 | −8.105  | −2.835 | 1.00 | 0.00 |
| ATOM | 338 | HH21 | ARG | 22 | 14.785 | −8.216  | −1.845 | 1.00 | 0.00 |
| ATOM | 339 | HH22 | ARG | 22 | 15.726 | −8.335  | −3.294 | 1.00 | 0.00 |
| ATOM | 340 | C    | ARG | 22 | 10.870 | −6.098  | 0.750  | 1.00 | 0.00 |
| ATOM | 341 | O    | ARG | 22 | 11.919 | −5.497  | 0.889  | 1.00 | 0.00 |
| ATOM | 342 | N    | GLY | 23 | 9.752  | −5.652  | 1.266  | 1.00 | 0.00 |
| ATOM | 343 | HN   | GLY | 23 | 8.923  | −6.159  | 1.141  | 1.00 | 0.00 |
| ATOM | 344 | CA   | GLY | 23 | 9.734  | −4.378  | 2.045  | 1.00 | 0.00 |
| ATOM | 345 | HA1  | GLY | 23 | 10.693 | −4.233  | 2.520  | 1.00 | 0.00 |
| ATOM | 346 | HA2  | GLY | 23 | 8.962  | −4.434  | 2.800  | 1.00 | 0.00 |
| ATOM | 347 | C    | GLY | 23 | 9.450  | −3.200  | 1.111  | 1.00 | 0.00 |
| ATOM | 348 | O    | GLY | 23 | 9.449  | −3.339  | −0.098 | 1.00 | 0.00 |
| ATOM | 349 | N    | PHE | 24 | 9.207  | −2.041  | 1.668  | 1.00 | 0.00 |

TABLE 5-continued

Atomic coordinates of Asp[28]IP(MetTrpLys) in PDB format

| ATOM | 350 | HN | PHE | 24 | 9.214 | −1.961 | 2.646 | 1.00 | 0.00 |
|---|---|---|---|---|---|---|---|---|---|
| ATOM | 351 | CA | PHE | 24 | 8.919 | −0.838 | 0.829 | 1.00 | 0.00 |
| ATOM | 352 | HA | PHE | 24 | 9.341 | −0.984 | −0.155 | 1.00 | 0.00 |
| ATOM | 353 | CB | PHE | 24 | 7.400 | −0.629 | 0.703 | 1.00 | 0.00 |
| ATOM | 354 | HB1 | PHE | 24 | 7.001 | −1.341 | −0.004 | 1.00 | 0.00 |
| ATOM | 355 | HB2 | PHE | 24 | 7.203 | 0.372 | 0.350 | 1.00 | 0.00 |
| ATOM | 356 | CG | PHE | 24 | 6.723 | −0.828 | 2.043 | 1.00 | 0.00 |
| ATOM | 357 | CD1 | PHE | 24 | 6.408 | −2.122 | 2.472 | 1.00 | 0.00 |
| ATOM | 358 | HD1 | PHE | 24 | 6.652 | −2.968 | 1.848 | 1.00 | 0.00 |
| ATOM | 359 | CD2 | PHE | 24 | 6.406 | 0.272 | 2.848 | 1.00 | 0.00 |
| ATOM | 360 | HD2 | PHE | 24 | 6.648 | 1.272 | 2.520 | 1.00 | 0.00 |
| ATOM | 361 | CE1 | PHE | 24 | 5.778 | −2.318 | 3.706 | 1.00 | 0.00 |
| ATOM | 362 | HE1 | PHE | 24 | 5.537 | −3.318 | 4.036 | 1.00 | 0.00 |
| ATOM | 363 | CE2 | PHE | 24 | 5.776 | 0.077 | 4.083 | 1.00 | 0.00 |
| ATOM | 364 | HE2 | PHE | 24 | 5.531 | 0.926 | 4.706 | 1.00 | 0.00 |
| ATOM | 365 | CZ | PHE | 24 | 5.461 | −1.220 | 4.513 | 1.00 | 0.00 |
| ATOM | 366 | HZ | PHE | 24 | 4.975 | −1.370 | 5.464 | 1.00 | 0.00 |
| ATOM | 367 | C | PHE | 24 | 9.557 | 0.396 | 1.472 | 1.00 | 0.00 |
| ATOM | 368 | O | PHE | 24 | 9.004 | 0.992 | 2.376 | 1.00 | 0.00 |
| ATOM | 369 | N | PHE | 25 | 10.722 | 0.780 | 1.010 | 1.00 | 0.00 |
| ATOM | 370 | HN | PHE | 25 | 11.146 | 0.278 | 0.283 | 1.00 | 0.00 |
| ATOM | 371 | CA | PHE | 25 | 11.408 | 1.972 | 1.590 | 1.00 | 0.00 |
| ATOM | 372 | HA | PHE | 25 | 11.138 | 2.074 | 2.631 | 1.00 | 0.00 |
| ATOM | 373 | CB | PHE | 25 | 12.924 | 1.791 | 1.474 | 1.00 | 0.00 |
| ATOM | 374 | HB1 | PHE | 25 | 13.411 | 2.748 | 1.591 | 1.00 | 0.00 |
| ATOM | 375 | HB2 | PHE | 25 | 13.163 | 1.382 | 0.503 | 1.00 | 0.00 |
| ATOM | 376 | CG | PHE | 25 | 13.407 | 0.848 | 2.551 | 1.00 | 0.00 |
| ATOM | 377 | CD1 | PHE | 25 | 13.976 | −0.381 | 2.200 | 1.00 | 0.00 |
| ATOM | 378 | HD1 | PHE | 25 | 14.069 | −0.657 | 1.161 | 1.00 | 0.00 |
| ATOM | 379 | CD2 | PHE | 25 | 13.284 | 1.206 | 3.898 | 1.00 | 0.00 |
| ATOM | 380 | HD2 | PHE | 25 | 12.845 | 2.154 | 4.169 | 1.00 | 0.00 |
| ATOM | 381 | CE1 | PHE | 25 | 14.423 | −1.255 | 3.197 | 1.00 | 0.00 |
| ATOM | 382 | HE1 | PHE | 25 | 14.864 | −2.204 | 2.927 | 1.00 | 0.00 |
| ATOM | 383 | CE2 | PHE | 25 | 13.732 | 0.332 | 4.896 | 1.00 | 0.00 |
| ATOM | 384 | HE2 | PHE | 25 | 13.639 | 0.606 | 5.937 | 1.00 | 0.00 |
| ATOM | 385 | CZ | PHE | 25 | 14.302 | −0.900 | 4.545 | 1.00 | 0.00 |
| ATOM | 386 | HZ | PHE | 25 | 14.648 | −1.573 | 5.315 | 1.00 | 0.00 |
| ATOM | 387 | C | PHE | 25 | 10.991 | 3.230 | 0.826 | 1.00 | 0.00 |
| ATOM | 388 | O | PHE | 25 | 10.374 | 3.155 | −0.220 | 1.00 | 0.00 |
| ATOM | 389 | N | TYR | 26 | 11.325 | 4.386 | 1.345 | 1.00 | 0.00 |
| ATOM | 390 | HN | TYR | 26 | 11.823 | 4.414 | 2.188 | 1.00 | 0.00 |
| ATOM | 391 | CA | TYR | 26 | 10.956 | 5.659 | 0.659 | 1.00 | 0.00 |
| ATOM | 392 | HA | TYR | 26 | 10.108 | 5.486 | 0.011 | 1.00 | 0.00 |
| ATOM | 393 | CB | TYR | 26 | 10.594 | 6.719 | 1.703 | 1.00 | 0.00 |
| ATOM | 394 | HB1 | TYR | 26 | 10.213 | 7.598 | 1.205 | 1.00 | 0.00 |
| ATOM | 395 | HB2 | TYR | 26 | 11.475 | 6.980 | 2.270 | 1.00 | 0.00 |
| ATOM | 396 | CG | TYR | 26 | 9.539 | 6.173 | 2.635 | 1.00 | 0.00 |
| ATOM | 397 | CD1 | TYR | 26 | 8.289 | 5.794 | 2.131 | 1.00 | 0.00 |
| ATOM | 398 | HD1 | TYR | 26 | 8.079 | 5.891 | 1.076 | 1.00 | 0.00 |
| ATOM | 399 | CD2 | TYR | 26 | 9.809 | 6.046 | 4.002 | 1.00 | 0.00 |
| ATOM | 400 | HD2 | TYR | 26 | 10.772 | 6.339 | 4.392 | 1.00 | 0.00 |
| ATOM | 401 | CE1 | TYR | 26 | 7.311 | 5.287 | 2.993 | 1.00 | 0.00 |
| ATOM | 402 | HE1 | TYR | 26 | 6.348 | 4.994 | 2.604 | 1.00 | 0.00 |
| ATOM | 403 | CE2 | TYR | 26 | 8.829 | 5.540 | 4.866 | 1.00 | 0.00 |
| ATOM | 404 | HE2 | TYR | 26 | 9.038 | 5.442 | 5.922 | 1.00 | 0.00 |
| ATOM | 405 | CZ | TYR | 26 | 7.581 | 5.161 | 4.362 | 1.00 | 0.00 |
| ATOM | 406 | OH | TYR | 26 | 6.616 | 4.661 | 5.212 | 1.00 | 0.00 |
| ATOM | 407 | HH | TYR | 26 | 6.614 | 3.707 | 5.129 | 1.00 | 0.00 |
| ATOM | 408 | C | TYR | 26 | 12.143 | 6.150 | −0.171 | 1.00 | 0.00 |
| ATOM | 409 | O | TYR | 26 | 13.211 | 5.565 | −0.147 | 1.00 | 0.00 |
| ATOM | 410 | N | THR | 27 | 11.966 | 7.221 | −0.907 | 1.00 | 0.00 |
| ATOM | 411 | HN | THR | 27 | 11.096 | 7.673 | −0.908 | 1.00 | 0.00 |
| ATOM | 412 | CA | THR | 27 | 13.084 | 7.753 | −1.741 | 1.00 | 0.00 |
| ATOM | 413 | HA | THR | 27 | 14.023 | 7.574 | −1.237 | 1.00 | 0.00 |
| ATOM | 414 | CB | THR | 27 | 13.094 | 7.039 | −3.097 | 1.00 | 0.00 |
| ATOM | 415 | HB | THR | 27 | 13.715 | 7.589 | −3.787 | 1.00 | 0.00 |
| ATOM | 416 | OG1 | THR | 27 | 11.770 | 6.969 | −3.604 | 1.00 | 0.00 |
| ATOM | 417 | HG1 | THR | 27 | 11.816 | 6.651 | −4.509 | 1.00 | 0.00 |
| ATOM | 418 | CG2 | THR | 27 | 13.657 | 5.627 | −2.928 | 1.00 | 0.00 |
| ATOM | 419 | HG21 | THR | 27 | 13.880 | 5.211 | −3.899 | 1.00 | 0.00 |
| ATOM | 420 | HG22 | THR | 27 | 12.925 | 5.007 | −2.429 | 1.00 | 0.00 |
| ATOM | 421 | HG23 | THR | 27 | 14.559 | 5.666 | −2.337 | 1.00 | 0.00 |
| ATOM | 422 | C | THR | 27 | 12.906 | 9.258 | −1.960 | 1.00 | 0.00 |
| ATOM | 423 | O | THR | 27 | 13.757 | 10.048 | −1.596 | 1.00 | 0.00 |
| ATOM | 424 | N | ASP | 28 | 11.813 | 9.660 | −2.564 | 1.00 | 0.00 |
| ATOM | 425 | HN | ASP | 28 | 11.147 | 9.003 | −2.857 | 1.00 | 0.00 |
| ATOM | 426 | CA | ASP | 28 | 11.588 | 11.115 | −2.820 | 1.00 | 0.00 |

TABLE 5-continued

Atomic coordinates of Asp[28]IP(MetTrpLys) in PDB format

| ATOM | 427 | HA | ASP | 28 | 12.312 | 11.692 | −2.264 | 1.00 | 0.00 |
|---|---|---|---|---|---|---|---|---|---|
| ATOM | 428 | CB | ASP | 28 | 11.759 | 11.396 | −4.315 | 1.00 | 0.00 |
| ATOM | 429 | HB1 | ASP | 28 | 11.472 | 12.415 | −4.524 | 1.00 | 0.00 |
| ATOM | 430 | HB2 | ASP | 28 | 11.133 | 10.722 | −4.881 | 1.00 | 0.00 |
| ATOM | 431 | CG | ASP | 28 | 13.222 | 11.188 | −4.712 | 1.00 | 0.00 |
| ATOM | 432 | OD1 | ASP | 28 | 13.942 | 12.170 | −4.780 | 1.00 | 0.00 |
| ATOM | 433 | OD2 | ASP | 28 | 13.597 | 10.050 | −4.941 | 1.00 | 0.00 |
| ATOM | 434 | C | ASP | 28 | 10.176 | 11.519 | −2.384 | 1.00 | 0.00 |
| ATOM | 435 | O | ASP | 28 | 9.993 | 12.153 | −1.363 | 1.00 | 0.00 |
| ATOM | 436 | N | LYS | 29 | 9.177 | 11.162 | −3.157 | 1.00 | 0.00 |
| ATOM | 437 | HN | LYS | 29 | 9.353 | 10.656 | −3.978 | 1.00 | 0.00 |
| ATOM | 438 | CA | LYS | 29 | 7.776 | 11.533 | −2.797 | 1.00 | 0.00 |
| ATOM | 439 | HA | LYS | 29 | 7.756 | 11.902 | −1.782 | 1.00 | 0.00 |
| ATOM | 440 | CB | LYS | 29 | 7.278 | 12.631 | −3.746 | 1.00 | 0.00 |
| ATOM | 441 | HB1 | LYS | 29 | 7.869 | 13.523 | −3.607 | 1.00 | 0.00 |
| ATOM | 442 | HB2 | LYS | 29 | 6.242 | 12.850 | −3.528 | 1.00 | 0.00 |
| ATOM | 443 | CG | LYS | 29 | 7.404 | 12.159 | −5.200 | 1.00 | 0.00 |
| ATOM | 444 | HG1 | LYS | 29 | 6.628 | 11.440 | −5.413 | 1.00 | 0.00 |
| ATOM | 445 | HG2 | LYS | 29 | 8.370 | 11.697 | −5.344 | 1.00 | 0.00 |
| ATOM | 446 | CD | LYS | 29 | 7.258 | 13.356 | −6.151 | 1.00 | 0.00 |
| ATOM | 447 | HD1 | LYS | 29 | 6.898 | 14.215 | −5.604 | 1.00 | 0.00 |
| ATOM | 448 | HD2 | LYS | 29 | 6.553 | 13.107 | −6.931 | 1.00 | 0.00 |
| ATOM | 449 | CE | LYS | 29 | 8.613 | 13.691 | −6.780 | 1.00 | 0.00 |
| ATOM | 450 | HE1 | LYS | 29 | 9.391 | 13.596 | −6.036 | 1.00 | 0.00 |
| ATOM | 451 | HE2 | LYS | 29 | 8.596 | 14.702 | −7.156 | 1.00 | 0.00 |
| ATOM | 452 | NZ | LYS | 29 | 8.885 | 12.749 | −7.905 | 1.00 | 0.00 |
| ATOM | 453 | HZ1 | LYS | 29 | 8.366 | 13.060 | −8.750 | 1.00 | 0.00 |
| ATOM | 454 | HZ2 | LYS | 29 | 8.574 | 11.792 | −7.638 | 1.00 | 0.00 |
| ATOM | 455 | HZ3 | LYS | 29 | 9.904 | 12.739 | −8.110 | 1.00 | 0.00 |
| ATOM | 456 | C | LYS | 29 | 6.874 | 10.299 | −2.904 | 1.00 | 0.00 |
| ATOM | 457 | O | LYS | 29 | 5.911 | 10.280 | −3.649 | 1.00 | 0.00 |
| ATOM | 458 | N | MET | 30 | 7.179 | 9.270 | −2.156 | 1.00 | 0.00 |
| ATOM | 459 | HN | MET | 30 | 7.957 | 9.312 | −1.562 | 1.00 | 0.00 |
| ATOM | 460 | CA | MET | 30 | 6.346 | 8.032 | −2.201 | 1.00 | 0.00 |
| ATOM | 461 | HA | MET | 30 | 5.882 | 7.948 | −3.171 | 1.00 | 0.00 |
| ATOM | 462 | CB | MET | 30 | 7.237 | 6.813 | −1.957 | 1.00 | 0.00 |
| ATOM | 463 | HB1 | MET | 30 | 7.274 | 6.597 | −0.900 | 1.00 | 0.00 |
| ATOM | 464 | HB2 | MET | 30 | 8.235 | 7.018 | −2.319 | 1.00 | 0.00 |
| ATOM | 465 | CG | MET | 30 | 6.664 | 5.607 | −2.701 | 1.00 | 0.00 |
| ATOM | 466 | HG1 | MET | 30 | 6.455 | 5.880 | −3.724 | 1.00 | 0.00 |
| ATOM | 467 | HG2 | MET | 30 | 5.751 | 5.288 | −2.219 | 1.00 | 0.00 |
| ATOM | 468 | SD | MET | 30 | 7.863 | 4.254 | −2.670 | 1.00 | 0.00 |
| ATOM | 469 | CE | MET | 30 | 7.265 | 3.464 | −1.156 | 1.00 | 0.00 |
| ATOM | 470 | HE1 | MET | 30 | 6.460 | 4.055 | −0.737 | 1.00 | 0.00 |
| ATOM | 471 | HE2 | MET | 30 | 8.069 | 3.399 | −0.441 | 1.00 | 0.00 |
| ATOM | 472 | HE3 | MET | 30 | 6.907 | 2.471 | −1.387 | 1.00 | 0.00 |
| ATOM | 473 | C | MET | 30 | 5.260 | 8.094 | −1.119 | 1.00 | 0.00 |
| ATOM | 474 | O | MET | 30 | 4.242 | 7.434 | −1.221 | 1.00 | 0.00 |
| ATOM | 475 | N | TRP | 31 | 5.469 | 8.873 | −0.086 | 1.00 | 0.00 |
| ATOM | 476 | HN | TRP | 31 | 6.298 | 9.389 | −0.024 | 1.00 | 0.00 |
| ATOM | 477 | CA | TRP | 31 | 4.455 | 8.970 | 1.007 | 1.00 | 0.00 |
| ATOM | 478 | HA | TRP | 31 | 3.952 | 8.022 | 1.116 | 1.00 | 0.00 |
| ATOM | 479 | CB | TRP | 31 | 5.158 | 9.324 | 2.319 | 1.00 | 0.00 |
| ATOM | 480 | HB1 | TRP | 31 | 5.222 | 10.397 | 2.414 | 1.00 | 0.00 |
| ATOM | 481 | HB2 | TRP | 31 | 6.154 | 8.903 | 2.317 | 1.00 | 0.00 |
| ATOM | 482 | CG | TRP | 31 | 4.385 | 8.766 | 3.468 | 1.00 | 0.00 |
| ATOM | 483 | CD1 | TRP | 31 | 3.902 | 9.490 | 4.503 | 1.00 | 0.00 |
| ATOM | 484 | HD1 | TRP | 31 | 4.010 | 10.557 | 4.630 | 1.00 | 0.00 |
| ATOM | 485 | CD2 | TRP | 31 | 3.999 | 7.384 | 3.719 | 1.00 | 0.00 |
| ATOM | 486 | NE1 | TRP | 31 | 3.246 | 8.639 | 5.376 | 1.00 | 0.00 |
| ATOM | 487 | HE1 | TRP | 31 | 2.807 | 8.913 | 6.208 | 1.00 | 0.00 |
| ATOM | 488 | CE2 | TRP | 31 | 3.277 | 7.331 | 4.935 | 1.00 | 0.00 |
| ATOM | 489 | CE3 | TRP | 31 | 4.203 | 6.185 | 3.016 | 1.00 | 0.00 |
| ATOM | 490 | HE3 | TRP | 31 | 4.748 | 6.195 | 2.084 | 1.00 | 0.00 |
| ATOM | 491 | CZ2 | TRP | 31 | 2.778 | 6.127 | 5.435 | 1.00 | 0.00 |
| ATOM | 492 | HZ2 | TRP | 31 | 2.231 | 6.112 | 6.367 | 1.00 | 0.00 |
| ATOM | 493 | CZ3 | TRP | 31 | 3.703 | 4.972 | 3.516 | 1.00 | 0.00 |
| ATOM | 494 | HZ3 | TRP | 31 | 3.866 | 4.056 | 2.968 | 1.00 | 0.00 |
| ATOM | 495 | CH2 | TRP | 31 | 2.991 | 4.944 | 4.724 | 1.00 | 0.00 |
| ATOM | 496 | HH2 | TRP | 31 | 2.610 | 4.007 | 5.104 | 1.00 | 0.00 |
| ATOM | 497 | C | TRP | 31 | 3.421 | 10.058 | 0.691 | 1.00 | 0.00 |
| ATOM | 498 | O | TRP | 31 | 2.338 | 10.065 | 1.243 | 1.00 | 0.00 |
| ATOM | 499 | N | LYS | 32 | 3.745 | 10.983 | −0.178 | 1.00 | 0.00 |
| ATOM | 500 | HN | LYS | 32 | 4.625 | 10.969 | −0.605 | 1.00 | 0.00 |
| ATOM | 501 | CA | LYS | 32 | 2.775 | 12.072 | −0.503 | 1.00 | 0.00 |
| ATOM | 502 | HA | LYS | 32 | 2.200 | 12.313 | 0.378 | 1.00 | 0.00 |
| ATOM | 503 | CB | LYS | 32 | 3.542 | 13.314 | −0.962 | 1.00 | 0.00 |

TABLE 5-continued

Atomic coordinates of Asp[28]IP(MetTrpLys) in PDB format

| ATOM | 504 | HB1 | LYS | 32 | 3.751 | 13.236 | −2.019 | 1.00 | 0.00 |
|---|---|---|---|---|---|---|---|---|---|
| ATOM | 505 | HB2 | LYS | 32 | 4.473 | 13.381 | −0.417 | 1.00 | 0.00 |
| ATOM | 506 | CG | LYS | 32 | 2.700 | 14.570 | −0.696 | 1.00 | 0.00 |
| ATOM | 507 | HG1 | LYS | 32 | 3.132 | 15.122 | 0.125 | 1.00 | 0.00 |
| ATOM | 508 | HG2 | LYS | 32 | 1.690 | 14.284 | −0.442 | 1.00 | 0.00 |
| ATOM | 509 | CD | LYS | 32 | 2.679 | 15.456 | −1.946 | 1.00 | 0.00 |
| ATOM | 510 | HD1 | LYS | 32 | 1.794 | 16.073 | −1.933 | 1.00 | 0.00 |
| ATOM | 511 | HD2 | LYS | 32 | 2.669 | 14.831 | −2.826 | 1.00 | 0.00 |
| ATOM | 512 | CE | LYS | 32 | 3.923 | 16.347 | −1.966 | 1.00 | 0.00 |
| ATOM | 513 | HE1 | LYS | 32 | 4.337 | 16.417 | −0.971 | 1.00 | 0.00 |
| ATOM | 514 | HE2 | LYS | 32 | 3.652 | 17.333 | −2.314 | 1.00 | 0.00 |
| ATOM | 515 | NZ | LYS | 32 | 4.935 | 15.758 | −2.887 | 1.00 | 0.00 |
| ATOM | 516 | HZ1 | LYS | 32 | 5.633 | 16.483 | −3.145 | 1.00 | 0.00 |
| ATOM | 517 | HZ2 | LYS | 32 | 4.461 | 15.410 | −3.745 | 1.00 | 0.00 |
| ATOM | 518 | HZ3 | LYS | 32 | 5.418 | 14.970 | −2.412 | 1.00 | 0.00 |
| ATOM | 519 | C | LYS | 32 | 1.829 | 11.620 | −1.617 | 1.00 | 0.00 |
| ATOM | 520 | O | LYS | 32 | 0.658 | 11.951 | −1.616 | 1.00 | 0.00 |
| ATOM | 521 | N | GLY | 33 | 2.328 | 10.879 | −2.574 | 1.00 | 0.00 |
| ATOM | 522 | HN | GLY | 33 | 3.277 | 10.635 | −2.556 | 1.00 | 0.00 |
| ATOM | 523 | CA | GLY | 33 | 1.463 | 10.419 | −3.697 | 1.00 | 0.00 |
| ATOM | 524 | HA1 | GLY | 33 | 2.079 | 10.208 | −4.559 | 1.00 | 0.00 |
| ATOM | 525 | HA2 | GLY | 33 | 0.756 | 11.198 | −3.947 | 1.00 | 0.00 |
| ATOM | 526 | C | GLY | 33 | 0.698 | 9.149 | −3.306 | 1.00 | 0.00 |
| ATOM | 527 | O | GLY | 33 | 0.296 | 8.811 | −3.921 | 1.00 | 0.00 |
| ATOM | 528 | N | ILE | 34 | 1.156 | 8.431 | −2.306 | 1.00 | 0.00 |
| ATOM | 529 | HN | ILE | 34 | 1.965 | 8.711 | −1.830 | 1.00 | 0.00 |
| ATOM | 530 | CA | ILE | 34 | 0.449 | 7.175 | −1.908 | 1.00 | 0.00 |
| ATOM | 531 | HA | ILE | 34 | 0.084 | 6.687 | −2.798 | 1.00 | 0.00 |
| ATOM | 532 | CB | ILE | 34 | 1.427 | 6.230 | −1.189 | 1.00 | 0.00 |
| ATOM | 533 | HB | ILE | 34 | 2.272 | 6.041 | −1.832 | 1.00 | 0.00 |
| ATOM | 534 | CG1 | ILE | 34 | 0.714 | 4.903 | −0.882 | 1.00 | 0.00 |
| ATOM | 535 | HG11 | ILE | 34 | 0.348 | 4.473 | −1.803 | 1.00 | 0.00 |
| ATOM | 536 | HG12 | ILE | 34 | −0.119 | 5.089 | −0.218 | 1.00 | 0.00 |
| ATOM | 537 | CG2 | ILE | 34 | 1.922 | 6.864 | 0.119 | 1.00 | 0.00 |
| ATOM | 538 | HG21 | ILE | 34 | 1.094 | 6.969 | 0.804 | 1.00 | 0.00 |
| ATOM | 539 | HG22 | ILE | 34 | 2.346 | 7.835 | −0.087 | 1.00 | 0.00 |
| ATOM | 540 | HG23 | ILE | 34 | 2.677 | 6.228 | 0.561 | 1.00 | 0.00 |
| ATOM | 541 | CD1 | ILE | 34 | 1.685 | 3.924 | −0.218 | 1.00 | 0.00 |
| ATOM | 542 | HD11 | ILE | 34 | 1.227 | 2.947 | −0.158 | 1.00 | 0.00 |
| ATOM | 543 | HD12 | ILE | 34 | 1.922 | 4.272 | 0.778 | 1.00 | 0.00 |
| ATOM | 544 | HD13 | ILE | 34 | 2.592 | 3.862 | −0.801 | 1.00 | 0.00 |
| ATOM | 545 | C | ILE | 34 | −0.743 | 7.490 | −0.992 | 1.00 | 0.00 |
| ATOM | 546 | O | ILE | 34 | −1.738 | 6.797 | −1.017 | 1.00 | 0.00 |
| ATOM | 547 | N | VAL | 35 | −0.644 | 8.509 | −0.177 | 1.00 | 0.00 |
| ATOM | 548 | HN | VAL | 35 | 0.175 | 9.048 | −0.161 | 1.00 | 0.00 |
| ATOM | 549 | CA | VAL | 35 | −1.773 | 8.837 | 0.750 | 1.00 | 0.00 |
| ATOM | 550 | HA | VAL | 35 | −2.296 | 7.928 | 1.006 | 1.00 | 0.00 |
| ATOM | 551 | CB | VAL | 35 | −1.216 | 9.472 | 2.028 | 1.00 | 0.00 |
| ATOM | 552 | HB | VAL | 35 | −0.771 | 10.427 | 1.791 | 1.00 | 0.00 |
| ATOM | 553 | CG1 | VAL | 35 | −2.352 | 9.673 | 3.034 | 1.00 | 0.00 |
| ATOM | 554 | HG11 | VAL | 35 | −3.111 | 8.923 | 2.874 | 1.00 | 0.00 |
| ATOM | 555 | HG12 | VAL | 35 | −2.781 | 10.655 | 2.900 | 1.00 | 0.00 |
| ATOM | 556 | HG13 | VAL | 35 | −1.964 | 9.584 | 4.037 | 1.00 | 0.00 |
| ATOM | 557 | CD2 | VAL | 35 | −0.158 | 8.546 | 2.637 | 1.00 | 0.00 |
| ATOM | 558 | HG21 | VAL | 35 | −0.220 | 8.585 | 3.714 | 1.00 | 0.00 |
| ATOM | 559 | HG22 | VAL | 35 | 0.823 | 8.866 | 2.323 | 1.00 | 0.00 |
| ATOM | 560 | HG23 | VAL | 35 | −0.329 | 7.533 | 2.305 | 1.00 | 0.00 |
| ATOM | 561 | C | VAL | 35 | −2.751 | 9.808 | 0.080 | 1.00 | 0.00 |
| ATOM | 562 | O | VAL | 35 | −3.919 | 9.847 | 0.420 | 1.00 | 0.00 |
| ATOM | 563 | N | GLU | 36 | −2.289 | 10.591 | −0.858 | 1.00 | 0.00 |
| ATOM | 564 | HN | GLU | 36 | −1.341 | 10.547 | −1.110 | 1.00 | 0.00 |
| ATOM | 565 | CA | GLU | 36 | −3.195 | 11.563 | −1.539 | 1.00 | 0.00 |
| ATOM | 566 | HA | GLU | 36 | −3.896 | 11.962 | −0.820 | 1.00 | 0.00 |
| ATOM | 567 | CB | GLU | 36 | −2.362 | 12.709 | −2.121 | 1.00 | 0.00 |
| ATOM | 568 | HB1 | GLU | 36 | −2.130 | 12.494 | −3.154 | 1.00 | 0.00 |
| ATOM | 569 | HB2 | GLU | 36 | −1.442 | 12.803 | −1.560 | 1.00 | 0.00 |
| ATOM | 570 | CG | GLU | 36 | −3.148 | 14.022 | −2.036 | 1.00 | 0.00 |
| ATOM | 571 | HG1 | GLU | 36 | −2.483 | 14.820 | −1.745 | 1.00 | 0.00 |
| ATOM | 572 | HG2 | GLU | 36 | −3.935 | 13.924 | −1.300 | 1.00 | 0.00 |
| ATOM | 573 | CD | GLU | 36 | −3.764 | 14.346 | −3.399 | 1.00 | 0.00 |
| ATOM | 574 | OE1 | GLU | 36 | −3.838 | 15.520 | −3.730 | 1.00 | 0.00 |
| ATOM | 575 | OE2 | GLU | 36 | −4.152 | 13.417 | −4.088 | 1.00 | 0.00 |
| ATOM | 576 | C | GLU | 36 | −3.962 | 10.866 | −2.667 | 1.00 | 0.00 |
| ATOM | 577 | O | GLU | 36 | −5.076 | 11.237 | −2.987 | 1.00 | 0.00 |
| ATOM | 578 | N | GLN | 37 | −3.372 | 9.874 | −3.281 | 1.00 | 0.00 |
| ATOM | 579 | HN | GLN | 37 | −2.470 | 9.602 | −3.012 | 1.00 | 0.00 |
| ATOM | 580 | CA | GLN | 37 | −4.059 | 9.163 | −4.402 | 1.00 | 0.00 |

TABLE 5-continued

Atomic coordinates of Asp[28]IP(MetTrpLys) in PDB format

| | | | | | | | | |
|---|---|---|---|---|---|---|---|---|
| ATOM | 581 | HA | GLN | 37 | −4.738 | 9.848 | −4.893 | 1.00 | 0.00 |
| ATOM | 582 | CB | GLN | 37 | −3.018 | 8.680 | −5.413 | 1.00 | 0.00 |
| ATOM | 583 | HB1 | GLN | 37 | −2.589 | 7.751 | −5.071 | 1.00 | 0.00 |
| ATOM | 584 | HB2 | GLN | 37 | −2.239 | 9.423 | −5.511 | 1.00 | 0.00 |
| ATOM | 585 | CG | GLN | 37 | −3.690 | 8.460 | −6.770 | 1.00 | 0.00 |
| ATOM | 586 | HG1 | GLN | 37 | −3.755 | 9.399 | −7.298 | 1.00 | 0.00 |
| ATOM | 587 | HG2 | GLN | 37 | −4.683 | 8.063 | −6.617 | 1.00 | 0.00 |
| ATOM | 588 | CD | GLN | 37 | −2.867 | 7.468 | −7.592 | 1.00 | 0.00 |
| ATOM | 589 | OE1 | GLN | 37 | −2.395 | 7.794 | −8.663 | 1.00 | 0.00 |
| ATOM | 590 | NE2 | GLN | 37 | −2.672 | 6.264 | −7.133 | 1.00 | 0.00 |
| ATOM | 591 | HE21 | GLN | 37 | −3.052 | 6.001 | −6.268 | 1.00 | 0.00 |
| ATOM | 592 | HE22 | GLN | 37 | −2.145 | 5.620 | −7.652 | 1.00 | 0.00 |
| ATOM | 593 | C | GLN | 37 | −4.852 | 7.960 | −3.883 | 1.00 | 0.00 |
| ATOM | 594 | O | GLN | 37 | −5.831 | 7.556 | −4.480 | 1.00 | 0.00 |
| ATOM | 595 | N | CYS | 38 | −4.422 | 7.368 | −2.797 | 1.00 | 0.00 |
| ATOM | 596 | HN | CYS | 38 | −3.618 | 7.697 | −2.345 | 1.00 | 0.00 |
| ATOM | 597 | CA | CYS | 38 | −5.138 | 6.167 | −2.265 | 1.00 | 0.00 |
| ATOM | 598 | HA | CYS | 38 | −5.589 | 5.631 | −3.086 | 1.00 | 0.00 |
| ATOM | 599 | HB1 | CYS | 38 | −4.649 | 4.387 | −1.174 | 1.00 | 0.00 |
| ATOM | 600 | HB2 | CYS | 38 | −3.674 | 5.787 | −0.749 | 1.00 | 0.00 |
| ATOM | 601 | C | CYS | 38 | −6.231 | 6.567 | −1.272 | 1.00 | 0.00 |
| ATOM | 602 | O | CYS | 38 | −7.400 | 6.350 | −1.513 | 1.00 | 0.00 |
| ATOM | 603 | CB | CYS | 38 | −4.136 | 5.252 | −1.563 | 1.00 | 0.00 |
| ATOM | 604 | SG | CYS | 38 | −2.871 | 4.725 | −2.746 | 1.00 | 0.00 |
| ATOM | 605 | N | CYS | 39 | −5.860 | 7.122 | −0.147 | 1.00 | 0.00 |
| ATOM | 606 | HN | CYS | 39 | −4.906 | 7.264 | 0.032 | 1.00 | 0.00 |
| ATOM | 607 | CA | CYS | 39 | −6.874 | 7.508 | 0.889 | 1.00 | 0.00 |
| ATOM | 608 | HA | CYS | 39 | −7.297 | 6.610 | 1.316 | 1.00 | 0.00 |
| ATOM | 609 | HB1 | CYS | 39 | −5.793 | 9.221 | 1.592 | 1.00 | 0.00 |
| ATOM | 610 | HB2 | CYS | 39 | −5.368 | 7.724 | 2.406 | 1.00 | 0.00 |
| ATOM | 611 | C | CYS | 39 | −8.010 | 8.348 | 0.274 | 1.00 | 0.00 |
| ATOM | 612 | O | CYS | 39 | −9.169 | 8.146 | 0.589 | 1.00 | 0.00 |
| ATOM | 613 | CB | CYS | 39 | −6.181 | 8.305 | 2.000 | 1.00 | 0.00 |
| ATOM | 614 | SG | CYS | 39 | −7.365 | 8.682 | 3.324 | 1.00 | 0.00 |
| ATOM | 615 | N | THR | 40 | −7.696 | 9.288 | −0.585 | 1.00 | 0.00 |
| ATOM | 616 | HN | THR | 40 | −6.757 | 9.440 | −0.821 | 1.00 | 0.00 |
| ATOM | 617 | CA | THR | 40 | −8.770 | 10.135 | −1.197 | 1.00 | 0.00 |
| ATOM | 618 | HA | THR | 40 | −9.290 | 10.671 | −0.415 | 1.00 | 0.00 |
| ATOM | 619 | CB | THR | 40 | −8.143 | 11.138 | −2.166 | 1.00 | 0.00 |
| ATOM | 620 | HB | THR | 40 | −8.918 | 11.747 | −2.607 | 1.00 | 0.00 |
| ATOM | 621 | OG1 | THR | 40 | −7.452 | 10.438 | −3.192 | 1.00 | 0.00 |
| ATOM | 622 | HG1 | THR | 40 | −6.826 | 9.844 | −2.773 | 1.00 | 0.00 |
| ATOM | 623 | CG2 | THR | 40 | −7.168 | 12.038 | −1.408 | 1.00 | 0.00 |
| ATOM | 624 | HG21 | THR | 40 | −6.743 | 12.762 | −2.087 | 1.00 | 0.00 |
| ATOM | 625 | HG22 | THR | 40 | −6.380 | 11.434 | −0.983 | 1.00 | 0.00 |
| ATOM | 626 | HG23 | THR | 40 | −7.695 | 12.552 | −0.619 | 1.00 | 0.00 |
| ATOM | 627 | C | THR | 40 | −9.766 | 9.251 | −1.954 | 1.00 | 0.00 |
| ATOM | 628 | O | THR | 40 | −10.959 | 9.491 | −1.933 | 1.00 | 0.00 |
| ATOM | 629 | N | SER | 41 | −9.284 | 8.238 | −2.620 | 1.00 | 0.00 |
| ATOM | 630 | HN | SER | 41 | −8.318 | 8.071 | −2.619 | 1.00 | 0.00 |
| ATOM | 631 | CA | SER | 41 | −10.192 | 7.333 | −3.385 | 1.00 | 0.00 |
| ATOM | 632 | HA | SER | 41 | −11.218 | 7.626 | −3.211 | 1.00 | 0.00 |
| ATOM | 633 | CB | SER | 41 | −9.865 | 7.469 | −4.877 | 1.00 | 0.00 |
| ATOM | 634 | HB1 | SER | 41 | −10.646 | 6.998 | −5.460 | 1.00 | 0.00 |
| ATOM | 635 | HB2 | SER | 41 | −8.924 | 6.989 | −5.088 | 1.00 | 0.00 |
| ATOM | 636 | OG | SER | 41 | −9.772 | 8.847 | −5.212 | 1.00 | 0.00 |
| ATOM | 637 | HG | SER | 41 | −8.925 | 9.172 | −4.895 | 1.00 | 0.00 |
| ATOM | 638 | C | SER | 41 | −9.981 | 5.884 | −2.900 | 1.00 | 0.00 |
| ATOM | 639 | O | SER | 41 | −9.741 | 5.659 | −1.728 | 1.00 | 0.00 |
| ATOM | 640 | N | ILE | 42 | −10.066 | 4.901 | −3.772 | 1.00 | 0.00 |
| ATOM | 641 | HN | ILE | 42 | −10.263 | 5.091 | −4.711 | 1.00 | 0.00 |
| ATOM | 642 | CA | ILE | 42 | −9.857 | 3.491 | −3.335 | 1.00 | 0.00 |
| ATOM | 643 | HA | ILE | 42 | −9.606 | 3.477 | −2.283 | 1.00 | 0.00 |
| ATOM | 644 | CB | ILE | 42 | −11.139 | 2.683 | −3.562 | 1.00 | 0.00 |
| ATOM | 645 | HB | ILE | 42 | −11.390 | 2.690 | −4.611 | 1.00 | 0.00 |
| ATOM | 646 | CG1 | ILE | 42 | −12.270 | 3.324 | −2.756 | 1.00 | 0.00 |
| ATOM | 647 | HG11 | ILE | 42 | −12.357 | 4.365 | −3.023 | 1.00 | 0.00 |
| ATOM | 648 | HG12 | ILE | 42 | −12.052 | 3.240 | −1.701 | 1.00 | 0.00 |
| ATOM | 649 | CG2 | ILE | 42 | −10.933 | 1.237 | −3.093 | 1.00 | 0.00 |
| ATOM | 650 | HG21 | ILE | 42 | −10.172 | 1.212 | −2.326 | 1.00 | 0.00 |
| ATOM | 651 | HG22 | ILE | 42 | −10.622 | 0.626 | −3.928 | 1.00 | 0.00 |
| ATOM | 652 | HG23 | ILE | 42 | −11.860 | 0.853 | −2.694 | 1.00 | 0.00 |
| ATOM | 653 | CD1 | ILE | 42 | −13.589 | 2.614 | −3.059 | 1.00 | 0.00 |
| ATOM | 654 | HD11 | ILE | 42 | −13.641 | 2.388 | −4.112 | 1.00 | 0.00 |
| ATOM | 655 | HD12 | ILE | 42 | −14.413 | 3.255 | −2.785 | 1.00 | 0.00 |
| ATOM | 656 | HD13 | ILE | 42 | −13.642 | 1.696 | −2.490 | 1.00 | 0.00 |
| ATOM | 657 | C | ILE | 42 | −8.699 | 2.897 | −4.139 | 1.00 | 0.00 |

TABLE 5-continued

Atomic coordinates of Asp$^{28}$IP(MetTrpLys) in PDB format

| ATOM | 658 | O | ILE | 42 | -8.885 | 2.325 | -5.197 | 1.00 | 0.00 |
|---|---|---|---|---|---|---|---|---|---|
| ATOM | 659 | N | CYS | 43 | -7.499 | 3.050 | -3.643 | 1.00 | 0.00 |
| ATOM | 660 | HN | CYS | 43 | -7.387 | 3.527 | -2.793 | 1.00 | 0.00 |
| ATOM | 661 | CA | CYS | 43 | -6.295 | 2.525 | -4.354 | 1.00 | 0.00 |
| ATOM | 662 | HA | CYS | 43 | -6.180 | 3.043 | -5.293 | 1.00 | 0.00 |
| ATOM | 663 | HB1 | CYS | 43 | -4.550 | 1.830 | -3.290 | 1.00 | 0.00 |
| ATOM | 664 | HB2 | CYS | 43 | -5.378 | 3.183 | -2.530 | 1.00 | 0.00 |
| ATOM | 665 | C | CYS | 43 | -6.442 | 1.022 | -4.617 | 1.00 | 0.00 |
| ATOM | 666 | O | CYS | 43 | -7.100 | 0.312 | -3.880 | 1.00 | 0.00 |
| ATOM | 667 | CB | CYS | 43 | -5.059 | 2.767 | -3.471 | 1.00 | 0.00 |
| ATOM | 668 | SG | CYS | 43 | -3.918 | 3.924 | -4.276 | 1.00 | 0.00 |
| ATOM | 669 | N | SER | 44 | -5.813 | 0.539 | -5.657 | 1.00 | 0.00 |
| ATOM | 670 | HN | SER | 44 | -5.283 | 1.137 | -6.225 | 1.00 | 0.00 |
| ATOM | 671 | CA | SER | 44 | -5.883 | -0.912 | -5.981 | 1.00 | 0.00 |
| ATOM | 672 | HA | SER | 44 | -6.568 | -1.404 | -5.305 | 1.00 | 0.00 |
| ATOM | 673 | CB | SER | 44 | -6.360 | -1.092 | -7.422 | 1.00 | 0.00 |
| ATOM | 674 | HB1 | SER | 44 | -7.440 | -1.078 | -7.445 | 1.00 | 0.00 |
| ATOM | 675 | HB2 | SER | 44 | -6.006 | -2.033 | -7.808 | 1.00 | 0.00 |
| ATOM | 676 | OG | SER | 44 | -5.843 | -0.035 | -8.221 | 1.00 | 0.00 |
| ATOM | 677 | HG | PHE | 44 | -6.246 | -0.095 | -9.091 | 1.00 | 0.00 |
| ATOM | 678 | C | PHE | 44 | -4.485 | -1.511 | -5.823 | 1.00 | 0.00 |
| ATOM | 679 | O | PHE | 44 | -3.498 | -0.798 | -5.827 | 1.00 | 0.00 |
| ATOM | 680 | N | LEU | 45 | -4.387 | -2.808 | -5.682 | 1.00 | 0.00 |
| ATOM | 681 | HN | LEU | 45 | -5.194 | -3.364 | -5.681 | 1.00 | 0.00 |
| ATOM | 682 | CA | LEU | 45 | -3.045 | -3.444 | -5.521 | 1.00 | 0.00 |
| ATOM | 683 | HA | LEU | 45 | -2.560 | -3.041 | -4.644 | 1.00 | 0.00 |
| ATOM | 684 | CB | LEU | 45 | -3.206 | -4.956 | -5.361 | 1.00 | 0.00 |
| ATOM | 685 | HB1 | LEU | 45 | -3.320 | -5.413 | -6.332 | 1.00 | 0.00 |
| ATOM | 686 | HB2 | LEU | 45 | -4.079 | -5.164 | -4.759 | 1.00 | 0.00 |
| ATOM | 687 | CG | LEU | 45 | -1.965 | -5.522 | -4.677 | 1.00 | 0.00 |
| ATOM | 688 | HG | LEU | 45 | -1.079 | -5.102 | -5.132 | 1.00 | 0.00 |
| ATOM | 689 | CD1 | LEU | 45 | -1.995 | -5.150 | -3.193 | 1.00 | 0.00 |
| ATOM | 690 | HD11 | LEU | 45 | -2.974 | -5.355 | -2.791 | 1.00 | 0.00 |
| ATOM | 691 | HD12 | LEU | 45 | -1.774 | -4.099 | -3.081 | 1.00 | 0.00 |
| ATOM | 692 | HD13 | LEU | 45 | -1.257 | -5.732 | -2.660 | 1.00 | 0.00 |
| ATOM | 693 | CD2 | LEU | 45 | -1.947 | -7.044 | -4.825 | 1.00 | 0.00 |
| ATOM | 694 | HD21 | LEU | 45 | -2.936 | -7.435 | -4.638 | 1.00 | 0.00 |
| ATOM | 695 | HD22 | LEU | 45 | -1.252 | -7.467 | -4.114 | 1.00 | 0.00 |
| ATOM | 696 | HD23 | LEU | 45 | -1.640 | -7.303 | -5.827 | 1.00 | 0.00 |
| ATOM | 697 | C | LEU | 4S | -2.187 | -3.154 | -6.754 | 1.00 | 0.00 |
| ATOM | 698 | O | LEU | 45 | -0.976 | -3.060 | -6.671 | 1.00 | 0.00 |
| ATOM | 699 | N | TYR | 46 | -2.809 | -3.008 | -7.895 | 1.00 | 0.00 |
| ATOM | 700 | HN | TYR | 46 | -3.786 | -3.087 | -7.930 | 1.00 | 0.00 |
| ATOM | 701 | CA | TYR | 46 | -2.045 | -2.721 | -9.141 | 1.00 | 0.00 |
| ATOM | 702 | HA | TYR | 46 | -1.290 | -3.477 | -9.281 | 1.00 | 0.00 |
| ATOM | 703 | CB | TYR | 46 | -3.007 | -2.732 | -10.336 | 1.00 | 0.00 |
| ATOM | 704 | HB1 | TYR | 46 | -3.810 | -2.033 | -10.158 | 1.00 | 0.00 |
| ATOM | 705 | HB2 | TYR | 46 | -3.414 | -3.724 | -10.459 | 1.00 | 0.00 |
| ATOM | 706 | CG | TYR | 46 | -2.264 | -2.335 | -11.590 | 1.00 | 0.00 |
| ATOM | 707 | CD1 | TYR | 46 | -2.461 | -1.062 | -12.137 | 1.00 | 0.00 |
| ATOM | 708 | HD1 | TYR | 46 | -3.146 | -0.369 | -11.659 | 1.00 | 0.00 |
| ATOM | 709 | CD2 | TYR | 46 | -1.376 | -3.233 | -12.193 | 1.00 | 0.00 |
| ATOM | 710 | HD2 | TYR | 46 | -1.220 | -4.211 | -11.760 | 1.00 | 0.00 |
| ATOM | 711 | CE1 | TYR | 46 | -1.770 | -0.686 | -13.295 | 1.00 | 0.00 |
| ATOM | 712 | HE1 | TYR | 46 | -1.921 | 0.296 | -13.719 | 1.00 | 0.00 |
| ATOM | 713 | CE2 | TYR | 46 | -0.683 | -2.856 | -13.349 | 1.00 | 0.00 |
| ATOM | 714 | HE2 | TYR | 46 | 0.002 | -3.547 | -13.819 | 1.00 | 0.00 |
| ATOM | 715 | CZ | TYR | 46 | -0.882 | -1.583 | -13.902 | 1.00 | 0.00 |
| ATOM | 716 | OH | TYR | 46 | -0.199 | -1.212 | -15.042 | 1.00 | 0.00 |
| ATOM | 717 | HH | TYR | 46 | 0.494 | -0.600 | -14.786 | 1.00 | 0.00 |
| ATOM | 718 | C | TYR | 46 | -1.371 | -1.349 | -9.025 | 1.00 | 0.00 |
| ATOM | 719 | O | TYR | 46 | -0.223 | -1.183 | -9.391 | 1.00 | 0.00 |
| ATOM | 720 | N | GLN | 47 | -2.080 | -0.369 | -8.541 | 1.00 | 0.00 |
| ATOM | 721 | HN | GLN | 47 | -3.008 | -0.524 | -8.266 | 1.00 | 0.00 |
| ATOM | 722 | CA | GLN | 47 | -1.485 | 0.990 | -8.416 | 1.00 | 0.00 |
| ATOM | 723 | HA | GLN | 47 | -1.092 | 1.295 | -9.376 | 1.00 | 0.00 |
| ATOM | 724 | CB | GLN | 47 | -2.567 | 1.969 | -7.974 | 1.00 | 0.00 |
| ATOM | 725 | HB1 | GLN | 47 | -2.118 | 2.917 | -7.729 | 1.00 | 0.00 |
| ATOM | 726 | HB2 | GLU | 47 | -3.075 | 1.572 | -7.110 | 1.00 | 0.00 |
| ATOM | 727 | CG | GLN | 47 | -3.573 | 2.161 | -9.110 | 1.00 | 0.00 |
| ATOM | 728 | HG1 | GLN | 47 | -4.325 | 1.388 | -9.057 | 1.00 | 0.00 |
| ATOM | 729 | HG2 | GLN | 47 | -3.060 | 2.100 | -10.060 | 1.00 | 0.00 |
| ATOM | 730 | CD | GLN | 47 | -4.246 | 3.531 | -8.980 | 1.00 | 0.00 |
| ATOM | 731 | OE1 | GLN | 47 | -4.262 | 4.117 | -7.915 | 1.00 | 0.00 |
| ATOM | 732 | NE2 | GLN | 47 | -4.809 | 4.068 | -10.028 | 1.00 | 0.00 |
| ATOM | 733 | HE21 | GLN | 47 | -4.797 | 3.595 | -10.887 | 1.00 | 0.00 |
| ATOM | 734 | HE22 | GLN | 47 | -5.241 | 4.943 | -9.957 | 1.00 | 0.00 |

TABLE 5-continued

Atomic coordinates of Asp[28]IP(MetTrpLys) in PDB format

| ATOM | 735 | C    | GLN | 47 | -0.346 | 0.951  | -7.393  | 1.00 | 0.00 |
|------|-----|------|-----|----|--------|--------|---------|------|------|
| ATOM | 736 | O    | GLN | 47 | 0.610  | 1.696  | -7.495  | 1.00 | 0.00 |
| ATOM | 737 | N    | LEU | 48 | -0.436 | 0.081  | -6.417  | 1.00 | 0.00 |
| ATOM | 738 | HN   | LEU | 48 | -1.212 | -0.516 | -6.363  | 1.00 | 0.00 |
| ATOM | 739 | CA   | LEU | 48 | 0.651  | -0.016 | -5.396  | 1.00 | 0.00 |
| ATOM | 740 | HA   | LEU | 48 | 1.124  | 0.947  | -5.295  | 1.00 | 0.00 |
| ATOM | 741 | CB   | LEU | 48 | 0.065  | -0.441 | -4.042  | 1.00 | 0.00 |
| ATOM | 742 | HB1  | LEU | 48 | 0.833  | -0.930 | -3.460  | 1.00 | 0.00 |
| ATOM | 743 | HB2  | LEU | 48 | -0.748 | -1.132 | -4.208  | 1.00 | 0.00 |
| ATOM | 744 | CG   | LEU | 48 | -0.457 | 0.777  | -3.266  | 1.00 | 0.00 |
| ATOM | 745 | HG   | LEU | 48 | -1.261 | 1.240  | -3.821  | 1.00 | 0.00 |
| ATOM | 746 | CD1  | LEU | 48 | -0.977 | 0.309  | -1.910  | 1.00 | 0.00 |
| ATOM | 747 | HD11 | LEU | 48 | -2.009 | 0.009  | -2.004  | 1.00 | 0.00 |
| ATOM | 748 | HD12 | LEU | 48 | -0.896 | 1.117  | -1.199  | 1.00 | 0.00 |
| ATOM | 749 | HD13 | LEU | 48 | -0.385 | -0.528 | -1.572  | 1.00 | 0.00 |
| ATOM | 750 | CD2  | LEU | 48 | 0.667  | 1.794  | -3.037  | 1.00 | 0.00 |
| ATOM | 751 | HD21 | LEU | 48 | 1.622  | 1.292  | -3.091  | 1.00 | 0.00 |
| ATOM | 752 | HD22 | LEU | 48 | 0.555  | 2.248  | -2.064  | 1.00 | 0.00 |
| ATOM | 753 | HD23 | LEU | 48 | 0.617  | 2.558  | -3.797  | 1.00 | 0.00 |
| ATOM | 754 | C    | LEU | 48 | 1.707  | -1.051 | -5.829  | 1.00 | 0.00 |
| ATOM | 755 | O    | LEU | 48 | 2.726  | -1.202 | -5.182  | 1.00 | 0.00 |
| ATOM | 756 | N    | GLU | 49 | 1.473  | -1.775 | -6.905  | 1.00 | 0.00 |
| ATOM | 757 | HN   | GLU | 49 | 0.646  | -1.650 | -7.410  | 1.00 | 0.00 |
| ATOM | 758 | CA   | GLU | 49 | 2.467  | -2.800 | -7.360  | 1.00 | 0.00 |
| ATOM | 759 | HA   | GLU | 49 | 2.543  | -3.576 | -6.616  | 1.00 | 0.00 |
| ATOM | 760 | CB   | GLU | 49 | 2.004  | -3.420 | -8.684  | 1.00 | 0.00 |
| ATOM | 761 | HB1  | GLU | 49 | 2.865  | -3.647 | -9.297  | 1.00 | 0.00 |
| ATOM | 762 | HB2  | GLU | 49 | 1.371  | -2.717 | -9.205  | 1.00 | 0.00 |
| ATOM | 763 | CG   | GLU | 49 | 1.215  | -4.711 | -8.413  | 1.00 | 0.00 |
| ATOM | 764 | HG1  | GLU | 49 | 0.227  | -4.613 | -8.820  | 1.00 | 0.00 |
| ATOM | 765 | HG2  | GLU | 49 | 1.144  | -4.879 | -7.351  | 1.00 | 0.00 |
| ATOM | 766 | CD   | GLU | 49 | 1.916  | -5.902 | -9.074  | 1.00 | 0.00 |
| ATOM | 767 | OE1  | GLU | 49 | 2.492  | -6.701 | -8.351  | 1.00 | 0.00 |
| ATOM | 768 | OE2  | GLU | 49 | 1.866  | -5.996 | -10.289 | 1.00 | 0.00 |
| ATOM | 769 | C    | GLU | 49 | 3.844  | -2.156 | -7.574  | 1.00 | 0.00 |
| ATOM | 770 | O    | GLU | 49 | 4.860  | -2.823 | -7.537  | 1.00 | 0.00 |
| ATOM | 771 | N    | ASN | 50 | 3.881  | -0.869 | -7.823  | 1.00 | 0.00 |
| ATOM | 772 | HN   | ASN | 50 | 3.046  | -0.357 | -7.869  | 1.00 | 0.00 |
| ATOM | 773 | CA   | ASN | 50 | 5.185  | -0.185 | -8.071  | 1.00 | 0.00 |
| ATOM | 774 | HA   | ASN | 50 | 5.893  | -0.902 | -8.457  | 1.00 | 0.00 |
| ATOM | 775 | CB   | ASN | 50 | 4.975  | 0.920  | -9.111  | 1.00 | 0.00 |
| ATOM | 776 | HB1  | ASN | 50 | 5.648  | 1.741  | -8.908  | 1.00 | 0.00 |
| ATOM | 777 | HB2  | ASN | 50 | 3.953  | 1.271  | -9.062  | 1.00 | 0.00 |
| ATOM | 778 | CG   | ASN | 50 | 5.258  | 0.368  | -10.509 | 1.00 | 0.00 |
| ATOM | 779 | OD1  | ASN | 50 | 6.361  | 0.475  | -11.005 | 1.00 | 0.00 |
| ATOM | 780 | ND2  | ASN | 50 | 4.300  | -0.219 | -11.169 | 1.00 | 0.00 |
| ATOM | 781 | HD21 | ASN | 50 | 3.409  | -0.305 | -10.770 | 1.00 | 0.00 |
| ATOM | 782 | HD22 | ASN | 50 | 4.469  | -0.577 | -12.066 | 1.00 | 0.00 |
| ATOM | 783 | C    | ASN | 50 | 5.743  | 0.428  | -6.778  | 1.00 | 0.00 |
| ATOM | 784 | O    | ASN | 50 | 6.350  | 1.482  | -6.806  | 1.00 | 0.00 |
| ATOM | 785 | N    | TYR | 51 | 5.553  | -0.216 | -5.650  | 1.00 | 0.00 |
| ATOM | 786 | HN   | TYR | 51 | 5.063  | -1.063 | -5.643  | 1.00 | 0.00 |
| ATOM | 787 | CA   | TYR | 51 | 6.088  | 0.349  | -4.372  | 1.00 | 0.00 |
| ATOM | 788 | HA   | TYR | 51 | 6.472  | 1.335  | -4.569  | 1.00 | 0.00 |
| ATOM | 789 | CB   | TYR | 51 | 4.956  | 0.454  | -3.351  | 1.00 | 0.00 |
| ATOM | 790 | HB1  | TYR | 51 | 5.360  | 0.475  | -2.351  | 1.00 | 0.00 |
| ATOM | 791 | HB2  | TYR | 51 | 4.289  | -0.387 | -3.464  | 1.00 | 0.00 |
| ATOM | 792 | CG   | TYR | 51 | 4.204  | 1.725  | -3.623  | 1.00 | 0.00 |
| ATOM | 793 | CD1  | TYR | 51 | 3.397  | 1.803  | -4.753  | 1.00 | 0.00 |
| ATOM | 794 | HD1  | TYR | 51 | 3.300  | 0.945  | -5.398  | 1.00 | 0.00 |
| ATOM | 795 | CD2  | TYR | 51 | 4.331  | 2.827  | -2.772  | 1.00 | 0.00 |
| ATOM | 796 | HD2  | TYR | 51 | 4.953  | 2.763  | -1.891  | 1.00 | 0.00 |
| ATOM | 797 | CE1  | TYR | 51 | 2.709  | 2.982  | -5.046  | 1.00 | 0.00 |
| ATOM | 798 | HE1  | TYR | 51 | 2.086  | 3.038  | -5.925  | 1.00 | 0.00 |
| ATOM | 799 | CE2  | TYR | 51 | 3.641  | 4.011  | -3.057  | 1.00 | 0.00 |
| ATOM | 800 | HE2  | TYR | 51 | 3.738  | 4.862  | -2.402  | 1.00 | 0.00 |
| ATOM | 801 | CZ   | TYR | 51 | 2.830  | 4.090  | -4.197  | 1.00 | 0.00 |
| ATOM | 802 | OH   | TYR | 51 | 2.152  | 5.257  | -4.482  | 1.00 | 0.00 |
| ATOM | 803 | HH   | TYR | 51 | 1.390  | 5.308  | -3.900  | 1.00 | 0.00 |
| ATOM | 804 | C    | TYR | 51 | 7.230  | -0.518 | -3.818  | 1.00 | 0.00 |
| ATOM | 805 | O    | TYR | 51 | 7.923  | -0.117 | -2.901  | 1.00 | 0.00 |
| ATOM | 806 | N    | CYS | 52 | 7.442  | -1.687 | -4.368  | 1.00 | 0.00 |
| ATOM | 807 | HN   | CYS | 52 | 6.879  | -1.991 | -5.103  | 1.00 | 0.00 |
| ATOM | 808 | CA   | CYS | 52 | 8.546  | -2.564 | -3.875  | 1.00 | 0.00 |
| ATOM | 809 | HA   | CYS | 52 | 8.538  | -2.580 | -2.794  | 1.00 | 0.00 |
| ATOM | 810 | HB1  | CYS | 52 | 9.063  | -4.649 | -3.923  | 1.00 | 0.00 |
| ATOM | 811 | HB2  | CYS | 52 | 8.548  | -3.997 | -5.475  | 1.00 | 0.00 |

TABLE 5-continued

Atomic coordinates of Asp²⁸IP(MetTrpLys) in PDB format

| ATOM | 812 | C | CYS | 52 | 9.886 | −2.011 | −4.367 | 1.00 | 0.00 |
|---|---|---|---|---|---|---|---|---|---|
| ATOM | 813 | O | CYS | 52 | 10.029 | −1.645 | −5.519 | 1.00 | 0.00 |
| ATOM | 814 | CB | CYS | 52 | 8.362 | −3.989 | −4.411 | 1.00 | 0.00 |
| ATOM | 815 | SG | CYS | 52 | 6.671 | −4.570 | −4.093 | 1.00 | 0.00 |
| ATOM | 816 | N | ASN | 53 | 10.868 | −1.949 | −3.501 | 1.00 | 0.00 |
| ATOM | 817 | HN | ASN | 53 | 10.726 | −2.252 | −2.580 | 1.00 | 0.00 |
| ATOM | 818 | CA | ASN | 53 | 12.203 | −1.421 | −3.913 | 1.00 | 0.00 |
| ATOM | 819 | HA | ASN | 53 | 12.072 | −0.513 | −4.483 | 1.00 | 0.00 |
| ATOM | 820 | CB | ASN | 53 | 13.041 | −1.123 | −2.665 | 1.00 | 0.00 |
| ATOM | 821 | HB1 | ASN | 53 | 13.670 | −1.974 | −2.443 | 1.00 | 0.00 |
| ATOM | 822 | HB2 | ASN | 53 | 12.384 | −0.933 | −1.828 | 1.00 | 0.00 |
| ATOM | 823 | CG | ASN | 53 | 13.918 | 0.105 | −2.919 | 1.00 | 0.00 |
| ATOM | 824 | OD1 | ASN | 53 | 15.130 | 0.023 | −2.861 | 1.00 | 0.00 |
| ATOM | 825 | ND2 | ASN | 53 | 13.354 | 1.248 | −3.198 | 1.00 | 0.00 |
| ATOM | 826 | HD21 | ASN | 53 | 12.378 | 1.316 | −3.245 | 1.00 | 0.00 |
| ATOM | 827 | HD22 | ASN | 53 | 13.908 | 2.041 | −3.361 | 1.00 | 0.00 |
| ATOM | 828 | C | ASN | 53 | 12.920 | −2.464 | −4.773 | 1.00 | 0.00 |
| ATOM | 829 | OT1 | ASN | 53 | 13.826 | −2.084 | −5.497 | 1.00 | 0.00 |
| ATOM | 830 | OT2 | ASN | 53 | 12.553 | −3.625 | −4.690 | 1.00 | 0.00 |
| END | | | | | | | | | |

Example 3

Relative Folding Stability of Asp$^{B28}$IP Analogs

For evaluation of folding stability for insulin precursor analogs, denaturation samples were prepared by combining different ratios of insulin precursor analog and GuHCl stock solutions with 10 mM Tris/ClO$_4^-$, pH 8.0. Protein stock solutions were typically 0.06 mM in 10 mM Tris/ClO$_4^-$, pH 8.0. GuHCl stock solutions were 8.25 M in 10 mM Tris/ClO$_4^-$, pH 8.0. CD spectra were recorded with a Jasco J-715 Spectropolarimeter calibrated with (+)-10-camphorsulfonic acid. All spectra were recorded at 20° C. The denaturation samples were scanned from 250 to 218 nm. Typical cell path length and protein concentration were 0.5 cm and 3 μM, respectively. All spectra were smoothed before subtraction of appropriate solvent blanks. The circular dichroism is expressed as, Δε, based on the molar concentration of peptide bond. For presentation purpose each curve is normalized to a 0–1 scale by dividing the observed change at each point by the total change observed in the experiment.

Data analysis. GuHCl denaturation curves were analyzed by assuming that the folding/unfolding transition is two-state as described by Santoro & Bolen (1988) Biochemistry 27:8063–8068 and Kaarsholm et al. (1993) Biochemistry 32:10773–10778, both of which publications are specifically incorporated herein by reference for teaching methods of calculating stability by GuHCl denaturation. This analysis yields a number of parameters including the GuHCl concentration at the midpoint of the denaturation curve, Cmid reflecting the concentration of denaturant necessary to unfold one-half of the protein population. An increase in folding stability is thus manifest by an increased value of Cmid. Equilibrium constants can be obtained at each denaturant concentration using $K=(\Delta\epsilon_N-\Delta\epsilon)/(\Delta\epsilon-\Delta\epsilon_U)$, where Δε is the observed value of the CD, and $\Delta\epsilon_N$ and $\Delta\epsilon_U$ represent the CD values for native and unfolded forms, respectively, at the given GuHCl concentration (Pace, 1975). Values for $\Delta\epsilon_N$ and $\Delta\epsilon_U$ at GuHCl concentrations in the transition region are obtained by linear extrapolation of the pre- and post-transition baselines into the transition region, i.e. $\Delta\epsilon_N = \Delta\epsilon^0_N + m_N[GuHCl]$, and $\Delta\epsilon_U = \Delta\epsilon^0_U + m_U[GuHCl]$, where $\Delta\epsilon^0_N$ and $\Delta\epsilon^0_U$ are intercepts, and $m_N$ and $m_U$ are slopes of the pre- and post-transition baselines, respectively. The free energy of unfolding at a given denaturant concentration in the transition zone is given by $\Delta G = -RT\ln K$. Assuming a linear dependence of ΔG on denaturant concentration: $\Delta G = \Delta G_{H_2O} - m[GuHCl]$, where $\Delta G_{H_2O}$ is the value of ΔG in the absence of denaturant, and m is a measure of the dependence of ΔG on denaturant concentration. Hence, ΔG values derived from K in the transition zone may be extrapolated back to 0 M denaturant to give $\Delta G_{H_2O}$. The relationship between Δε and [GuHCl] for the complete unfolding curve is shown in Eq. 1 (Santoro & Bolen, 1988):

$$\Delta\varepsilon = \frac{(\Delta\varepsilon^0_N + m_N[GuHCl]) + (\Delta\varepsilon^0_U + m_U[GuHCl])\exp(-(\Delta G_{H_2O} - m[GuHCl])/RT)}{1 + \exp(-(\Delta G_{H_2O} - m[GuHCl])/RT)} \quad (1)$$

With Δε as the response and [GuHCl] as the independent variable, eq. (1) is subject to nonlinear least squares analysis using the NLIN procedure of PC SAS (SAS Inc. Cary, N.C.). Six parameters then describe the denaturation curve: $\Delta\epsilon^0_N$, $\Delta\epsilon^0_U$, $m_N$, $m_U$, m, and $\Delta G_{H_2O}$. In addition, the GuHCl concentration at the midpoint of the denaturation curve, Cmid, is given by $\Delta G_{H_2O}/m$.

Evaluation of the relative folding stability of Asp$^{B28}$IP derivative molecules with C-peptide Met Trp Lys (Asp$^{B28}$IP (MetTrpLys)) was evaluated relative to Asp$^{B28}$IP. The results show that the Asp$^{B28}$IP(MetTrpLys) molecule was much more stable than Asp$^{B28}$IP (FIG. 5), as evidenced by the change in Cmid. While Cmid for Asp$^{B28}$IP is approximately about 5.5 M GuHCl, that of Asp$^{B28}$IP(MetTrpLys) is increased to at least about 6.5 M GuHCl, an increase of approximately 18%.

Example 4

The insulin analogue precursor Asp$^{B28}$IP(EWK) was produced culturing yeast strain MT663 transformed with an expression plasmid expressing a YAP3-TA39-EEGEPK (SEQ ID NO:17)-Asp$^{B28}$IP(EWK) fusion protein or a YAP3-TA57-EEGEPK(SEQ ID NO:17)-Asp$^{B28}$IP(EWK) fusion protein.

cDNA encoding the leader sequences YAP3-TA39 and YAP3-TA57 and cDNA encoding the Asp$^{B28}$IP(EWK) and the N-terminal extension were cloned into an expression vector of the C-POT type using standard techniques (Sambrook J, Fritsch E F and Maniatis T, Molecular cloning, Cold spring Harbour laboratory press, 1989). The DNA and inferred amino acids sequences are shown in FIGS. 8 and 9.

Table 6 shows the yields. Fermentation was conducted at 30° C. for 72 h in 5 ml YPD. IP yield was determined by RP-HPLC of the culture supernatant and is expressed relative to the IP yield of a control strain.

In Table 6, "α*" indicates an α-factor leader in which the C-terminus up to the LysArg has been modified from "SLD (SerLeuAsp)" to "SMA (SerMet Ala)" and "ex4" is an N-terminal extension with the amino acid sequence EEAEAEAPK(SEQ ID NO:4). YAP3 is the YAP3 signal sequence. TA39 is a synthetic pro-sequence QPID-DTESNTTSVNLMADDTESRFATNTTLAG-GLDWNLISMAKR (SEQ ID NO:16). The sequence EEGEPK(SEQ ID NO:17) is an N-terminal extension to the B-chain of the insulin analogue. TA57 is a synthetic pro-sequence QPIDDTESQTTSVNLMADDTESAFATQT-NSGGLDWGLISMAKR (SEQ ID NO: 18).

TABLE 6

| Leader | Precursor | N-terminal extension | C-peptide | Yield* |
|---|---|---|---|---|
| α*-ex4 | Asp$^{B28}$IP | GluGluAlaGluAlaGluAlaProLys (SEQ ID NO: 4) | None | 100 |
| YAP3-TA39 | Asp$^{B28}$IP | GluGluGlyGluProLys (SEQ ID NO: 17) | GluTrpLys | 531% |
| YAP3-TA57 | Asp$^{B28}$IP | GluGluGlyGluProLys (SEQ ID NO: 17) | GluTrpLys | 500% |

What is claimed is:

1. An insulin precursor or insulin analog precursor comprising a connecting peptide (C-peptide) being cleavable from the A and B chains said connecting peptide comprising at least one aromatic amino acid residue and a cleavage site enabling cleavage of the peptide bond between the A-chain and the connecting peptide, wherein one aromatic amino acid residue is immediately N-terminal to said cleavage site.

2. An insulin precursor or insulin analog precursor according to claim 1, wherein the connecting peptide is of up to 15 amino acid residues in length.

3. An insulin precursor or insulin analog precursor according to claim 1, wherein the connecting peptide is of up to 9 amino acid residues.

4. An insulin precursor or insulin analog precursor according to claim 1, wherein the connecting peptide is of up to 5 amino acid residues.

5. An insulin precursor or insulin analog precursor according to claim 1, wherein the cleavage site enabling cleavage of the peptide bond between die A-chain and the connecting peptide is Lys or Arg.

6. An insulin precursor or insulin analog precursor according to claim 1, wherein the connecting peptide comprises up to 5 aromatic amino acid residues.

7. An insulin precursor or insulin analog precursor according to claim 1, wherein the connecting peptide comprises up to 3 aromatic amino acid residues.

8. An insulin precursor or insulin analog precursor according to claim 7, wherein one of die aromatic amino acid residues is less than 5 Å away from at least one of the amino acid residues in position B11, B12 or B26 in the B chain.

9. An insulin precursor or insulin analog precursor according to claim 1, wherein the aromatic amino acid residue immediately N-terminal to the cleavage site is less than 5 Å away from at least one of the amino acid residues in position B11, B12 or B26 in the B chain.

10. An insulin precursor or insulin analog precursor having the formula:

$$B(1-27)-X_2-X_3-X_1-Y-A(1-21)$$

wherein $X_1$ is a peptide sequence of 1–6 amino acid residues of which at least one is an aromatic amino acid residue, $X_2$ is one of Pro, Asp, Lys, or Ile at position 28 of the B chain, $X_3$ is one of Pro, Lys, Ala, Arg, or Pro-Thr at position 29 of the B chain, and Y is Lys or Arg.

11. An insulin precursor or insulin analog precursor of claim 10, wherein $X_1$ is 1–4 amino acid residues.

12. An insulin precursor or insulin analog precursor of claim 10, wherein $X_1$ is 1–3 amino acid residues.

13. An insulin precursor or insulin analog precursor of claim 10, wherein $X_1$ is 1–2 amino acid residues.

14. An insulin precursor or insulin analog precursor of claim 10 wherein X1-Y is selected from the group of: (a) Met-Trp-Lys, (b) Ala-Trp-Lys, (c) Val-Trp-Lys, (d) Ile-Trp-Lys, (e) Leu-Trp-Lys, (f) Glu-Glu-Phe-Lys (SEQ ID NO: 15), (g) Glu-Phe-Lys, (h) Glu-Trp-Lys, (i) Ser-Trp-Lys, (j) Thr-Trp-Lys, (k) Arg-Trp-Lys, (l) Glu-Met-Trp-Lys (SEQ ID NO: 1), (m) Gln-Met-Trp-Lys (SEQ ID NO: 2), and (n) Asp-Trp-Lys.

15. An insulin precursor or insulin analog precursor of claim 10 wherein $X_2$ is Asp, $X_3$ is Lys and $X_1$ is 1–3 amino acid residues of which one is Trp or Phe.

16. An insulin precursor or insulin analog precursor having the formula:

$$B(1\text{-}27)\text{-}X_2\text{-}X_3\text{-}X_1\text{-}Y\text{-}A(1\text{-}21)$$

wherein $X_1$ is a peptide sequence of 1–8 amino acid residues of which 2–5 are aromatic amino acid residues, $X_2$ is one of Pro, Asp, Lys, or Ile at position 28 of the B chain, $X_1$ is one of Pro, Lys, Ala, Arg or Pro-Thr at position 29 of the B chain, and Y is Lys or Arg.

17. An insulin precursor or insulin analog precursor of claim 16 wherein $X_1$ comprises 2–3 aromatic amino acid residues.

18. An insulin precursor or insulin analog precursor having the formula:

$$B(1\text{-}27)\text{-}X_2\text{-}X_3\text{-}X_1\text{-}Y\text{-}A(1\text{-}21)$$

wherein $X_1$ is a peptide sequence of 1–8 amino acid residues of which at least one is Trp, $X_2$ is one of Pro, Asp, Lys, or Ile at position 28 of the B chain, $X_3$ is one of Pro, Lys, Ala, Arg or Pro-Thr at position 29 of the B chain, and Y is Lys or Arg.

19. An insulin precursor or insulin analog precursor having the formula:

$$B(1\text{-}27)\text{-}X_2\text{-}X_3\text{-}X_1\text{-}Y\text{-}A(1\text{-}21)$$

wherein $X_1$ is a peptide sequence of 1–8 amino acid residues of which at least one is an aromatic amino acid residue, $X_2$ is one of Pro, Asp, Lys, or Ile at position 28 of the B chain, $X_3$ is one of Pro, Lys, Ala, Arg or Pro-Thr at position 29 of the B chain, and Y is Lys or Arg, wherein one aromatic amino acid residues is less than 5 Å away from at least one of file amino acid residues in position B11, B12 or B26 in the B chain.

20. An insulin precursor or insulin analog precursor having the formula:

$$B(1\text{-}27)\text{-}X_2\text{-}X_3\text{-}X_1\text{-}Y\text{-}A(1\text{-}21)$$

wherein $X_1$ is a peptide sequence of 1–8 amino acid residues of which at least one is an aromatic amino acid residue immediately N-terminal to Y, $X_2$ is one of Pro, Asp, Lys, or Ile at position 28 of the B chain, $X_3$ is one of Pro, Lys, Ala, Arg or Pro-Thr at position 29 of the B chain, and Y is Lys or Arg.

21. An insulin precursor or insulin analog precursor according to claim 20, wherein the aromatic amino acid residue immediately N-terminal to Y is less than 5 Å away from at least one of the amino acid residues in position B11, B12 or B26 in the B chain.

22. An insulin precursor or insulin analog precursor having the formula:

$$B(1\text{-}27)\text{-}X_2\text{-}X_3\text{-}X_1\text{-}Y\text{-}A(1\text{-}21)$$

wherein $X_1$ is a peptide sequence of 1–15 amino acid residues of which one is an aromatic amino acid residue immediately N-terminal to Y, $X_2$ is one of Pro, Asp, Lys, or Ile at position 28 of the B chain, $X_3$ is one of Pro, Lys, Ala, Arg or Pro-Thr at position 29 of the B chain, aud Y is Lys or Arg.

23. An insulin analog precursor having the formula:

$$B(1\text{-}27)\text{-}X_2\text{-}X_3\text{-}X_1\text{-}Y\text{-}A(1\text{-}21)$$

wherein $X_1$ is a peptide sequence of 1–15 amino acid residues of which one is an aromatic amino acid residue which is less than 5 Å away from at least one of the amino acid residues in position B11, B12 or B26 in the B chain, $X_2$ is one of Asp, Lys, or Ile at position 28 of the B chain, $X_3$ is one of Pro, Lys, Ala, Arg or Pro-Thr at position 29 of the B chain, and Y is Lys or Arg.

24. An insulin precursor or insulin analog precursor having the formula:

$$B(1\text{-}27)\text{-}X_2\text{-}X_3\text{-}X_1\text{-}Y\text{-}A(1\text{-}21)$$

wherein $X_1$ consists of one aromatic amino acid residue, $X_2$ is one of Pro, Asp, Lys, or Ile at position 28 of the B chain, $X_3$ is one of Pro, Lys, Ala, Arg or Pro-Thr at position 29 of the B chain, and Y is Lys or Arg.

25. An insulin analog precursor having the formula:

$$B(1\text{-}27)\text{-}X_2\text{-}X_3\text{-}X_1\text{-}Y\text{-}A(1\text{-}21)$$

wherein $X_1$ is a peptide sequence of 1–15 amino acid residues of which one is an aromatic amino acid residue immediately N-terminal to Y, $X_2$ is one of Pro, Asp, Lys, or Ile at position 28 of the B chain, $X_3$ is one of Pro, Ala, Arg or Pro-Thr at position 29 of the B chain, and Y is Lys or Arg.

26. An insulin analog precursor having the formula:

$$B(1\text{-}27)\text{-}X_2\text{-}X_3\text{-}X_1\text{-}Y\text{-}A(1\text{-}21)$$

wherein $X_1$ is a peptide sequence of 1–15 amino acid residues of which one is an aromatic amino acid residue which is less than 5 Å away from at least one of the amino acid residues in position B11, B12 or B26 in the B chain, $X_2$ is one of Pro, Asp, Lys, or Ile at position 28 of the B chain, $X_3$ is one of Pro, Ala, Arg or Pro-Thr at position 29 of the B chain, and Y is Lys or Arg.

27. An insulin analog precursor having the formula:

$$B(1-27)-X_2-X_3-X_1-Y-A(1-21)$$

wherein
- $X_1$ is a peptide sequence of 1–8 amino acid residues of which at least one is an aromatic amino acid residue,
- $X_2$ is one of Asp, Lys, or Ile at position 28 of the B chain,
- $X_3$ is one of Pro, Lys, Ala, Arg or Pro-Thr at position 29 of the B chain, and
- Y is Lys or Arg.

wherein the insulin precursor or insulin precursor analog exhibits an increased Cmid stability in solution relative to an insulin analog precursor lacking an aromatic amino acid residue in $X_1$.

28. An insulin analog precursor according to claim 27, wherein Cmid is higher than about 5.5 M GuHCl.

29. An insulin analog precursor according to claim 28, wherein Cmid is higher than about 6.0 M GuHCl.

30. An insulin analog precursor according to claim 29, wherein Cmid is at least about 6.5 M GuHCl.

31. A polynucleotide sequence encoding an insulin precursor or insulin analog precursor according to claim 1.

32. An expression vector comprising the polynucleotide sequence of claim 31.

33. A host cell transformed with a vector of claim 32.

34. A process for making an insulin precursor or an insulin analog precursor, said method comprising (i) culturing a host cell comprising the polynucleotide sequence of claim 31 under suitable culture conditions for expressing the precursor; and (ii) isolating the expressed precursor.

35. A process according to claim 34, wherein the host cell is a yeast host cell.

36. A process for making insulin or an insulin analog, said method comprising (i) culturing a host cell comprising the polynucleotide sequence of claim 31 under suitable culture conditions for expressing the precursor; (ii) isolating the precursor from the culture medium and (iii) converting the precursor into insulin or an insulin analog by in vitro chemical or enzymatic conversion.

37. A process according to claim 36, wherein the host cell is a yeast host cell.

38. An insulin precursor or insulin analog precursor according to claim 4, wherein the connecting peptide is of up to 3 amino acid residues.

39. An insulin precursor or insulin analog precursor according to claim 7, wherein the connecting peptide comprises only one aromatic amino acid residue.

40. A process for making insulin or an insulin analog, said method comprising (i) culturing a host cell expressing the insulin precursor or insulin analog precursor according to claim 10 under suitable culture conditions for expressing the precursor; (ii) isolating the precursor from the culture medium and (iii) converting the precursor into insulin or an insulin analog by in vitro chemical or enzymatic conversion.

* * * * *

UNITED STATES PATENT AND TRADEMARK OFFICE
CERTIFICATE OF CORRECTION

PATENT NO.    : 6,521,738 B2
DATED         : February 18, 2003
INVENTOR(S)   : Thomas Kjeldsen et al.

It is certified that error appears in the above-identified patent and that said Letters Patent is hereby corrected as shown below:

Column 55,
Line 64, "wherein one of die aromatic amino" should read -- wherein one of the aromatic amino --.

Column 56,
Line 61, "wherein X1-Y is selected from the group" should read -- wherein $X_1$-Y is selected from the group --.

Column 57,
Line 14, "X1 is one of the Pro," should read -- $X_3$ is one of the Pro, --.

Signed and Sealed this

Second Day of December, 2003

JAMES E. ROGAN
*Director of the United States Patent and Trademark Office*

SEQUENCE LISTING

```
<160> NUMBER OF SEQ ID NOS:  18

<210> SEQ ID NO 1
<211> LENGTH: 4
<212> TYPE: PRT
<213> ORGANISM: Mini C peptide

<400> SEQUENCE: 1

Glu Met Trp Lys
 1

<210> SEQ ID NO 2
<211> LENGTH: 4
<212> TYPE: PRT
<213> ORGANISM: Mini C peptide

<400> SEQUENCE: 2

Gln Met Trp Lys
 1

<210> SEQ ID NO 3
<211> LENGTH: 10
<212> TYPE: PRT
<213> ORGANISM: N-terminal extension

<400> SEQUENCE: 3

Glu Glu Ala Glu Ala Glu Ala Glu Pro Lys
 1               5                   10

<210> SEQ ID NO 4
<211> LENGTH: 9
<212> TYPE: PRT
<213> ORGANISM: N-terminal extension

<400> SEQUENCE: 4

Glu Glu Ala Glu Ala Glu Ala Pro Lys
 1               5

<210> SEQ ID NO 5
<211> LENGTH: 600
<212> TYPE: DNA
<213> ORGANISM: N-terminally extension
```

```
<220> FEATURE:
<221> NAME/KEY: CDS
<222> LOCATION: (114)...(545)

<400> SEQUENCE: 5
tcttgcttaa atctataact acaaaaaaca catacaggaa ttccattcaa gatctgttca      60
aacaagaaga ttacaaacta tcaatttcat acacaatata aacgattaaa aga atg       116
                                                         Met
                                                           1 aga ttt cct tca att ttt act gca gtt tta ttc gca gca tcc tcc gca      164
Arg Phe Pro Ser Ile Phe Thr Ala Val Leu Phe Ala Ala Ser Ser Ala
          5                  10                  15 tta gct gct cca gtc aac act aca aca gaa gat gaa acg gca caa att      212
Leu Ala Ala Pro Val Asn Thr Thr Thr Glu Asp Glu Thr Ala Gln Ile
     20                  25                  30 ccg gct gaa gct gtc atc ggt tac tca gat tta gaa ggg gat ttc gat      260
Pro Ala Glu Ala Val Ile Gly Tyr Ser Asp Leu Glu Gly Asp Phe Asp
 35                  40                  45 gtt gct gtt ttg cca ttt tcc aac agc aca aat aac ggg tta ttg ttt      308
Val Ala Val Leu Pro Phe Ser Asn Ser Thr Asn Asn Gly Leu Leu Phe
 50                  55                  60                  65 ata aat act act att gcc agc att gct gct aaa gaa gaa ggg gta tcc      356
Ile Asn Thr Thr Ile Ala Ser Ile Ala Ala Lys Glu Glu Gly Val Ser
             70                  75                  80 atg gct aag aga gaa gaa gct gaa gct gaa gct cca aag ttc gtt aac      404
Met Ala Lys Arg Glu Glu Ala Glu Ala Glu Ala Pro Lys Phe Val Asn
         85                  90                  95 caa cac ttg tgt ggt tct cac ttg gtt gaa gct ttg tac ttg gtt tgt      452
Gln His Leu Cys Gly Ser His Leu Val Glu Ala Leu Tyr Leu Val Cys
     100                 105                 110 ggt gaa aga ggt ttc ttc tac act gac aag ggt atc gtt gaa caa tgt      500
Gly Glu Arg Gly Phe Phe Tyr Thr Asp Lys Gly Ile Val Glu Gln Cys
 115                 120                 125 tgt act tct atc tgt tct ttg tac caa ttg gaa aac tac tgt aac          545
Cys Thr Ser Ile Cys Ser Leu Tyr Gln Leu Glu Asn Tyr Cys Asn
130                 135                 140 tagacgcagc ccgcaggctc tagaaactaa gattaatata attatataaa aatat         600

<210> SEQ ID NO 6
<211> LENGTH: 144
<212> TYPE: PRT
<213> ORGANISM: N-terminally extension

<400> SEQUENCE: 6

Met Arg Phe Pro Ser Ile Phe Thr Ala Val Leu Phe Ala Ala Ser Ser
  1               5                  10                  15

Ala Leu Ala Ala Pro Val Asn Thr Thr Thr Glu Asp Glu Thr Ala Gln
                 20                  25                  30

Ile Pro Ala Glu Ala Val Ile Gly Tyr Ser Asp Leu Glu Gly Asp Phe
             35                  40                  45

Asp Val Ala Val Leu Pro Phe Ser Asn Ser Thr Asn Asn Gly Leu Leu
         50                  55                  60

Phe Ile Asn Thr Thr Ile Ala Ser Ile Ala Ala Lys Glu Glu Gly Val
 65                  70                  75                  80

Ser Met Ala Lys Arg Glu Glu Ala Glu Ala Glu Ala Pro Lys Phe Val
                 85                  90                  95

Asn Gln His Leu Cys Gly Ser His Leu Val Glu Ala Leu Tyr Leu Val
            100                 105                 110
```

```
Cys Gly Glu Arg Gly Phe Phe Tyr Thr Asp Lys Gly Ile Val Glu Gln
            115                 120                 125

Cys Cys Thr Ser Ile Cys Ser Leu Tyr Gln Leu Glu Asn Tyr Cys Asn
130                 135                 140

<210> SEQ ID NO 7
<211> LENGTH: 600
<212> TYPE: DNA
<213> ORGANISM: N-terminal extension
<220> FEATURE:
<221> NAME/KEY: CDS
<222> LOCATION: (114)...(554)

<400> SEQUENCE: 7
tcttgcttaa atctataact acaaaaaaca catacaggaa ttccattcaa gatctgttca      60
aacaagaaga ttacaaacta tcaatttcat acacaatata aacgattaaa aga atg       116
                                                            Met
                                                             1 aga ttt cct tca att ttt act gca gtt tta ttc gca gca tcc tcc gca       164
Arg Phe Pro Ser Ile Phe Thr Ala Val Leu Phe Ala Ala Ser Ser Ala
            5                   10                  15 tta gct gct cca gtc aac act aca aca gaa gat gaa acg gca caa att       212
Leu Ala Ala Pro Val Asn Thr Thr Thr Glu Asp Glu Thr Ala Gln Ile
        20                  25                  30 ccg gct gaa gct gtc atc ggt tac tca gat tta gaa ggg gat ttc gat       260
Pro Ala Glu Ala Val Ile Gly Tyr Ser Asp Leu Glu Gly Asp Phe Asp
    35                  40                  45 gtt gct gtt ttg cca ttt tcc aac agc aca aat aac ggg tta ttg ttt       308
Val Ala Val Leu Pro Phe Ser Asn Ser Thr Asn Asn Gly Leu Leu Phe
50                  55                  60                  65 ata aat act act att gcc agc att gct gct aaa gaa gaa ggg gta tcc       356
Ile Asn Thr Thr Ile Ala Ser Ile Ala Ala Lys Glu Glu Gly Val Ser
                70                  75                  80 atg gct aag aga gaa gaa gct gaa gct gaa gct cca aag ttc gtt aac       404
Met Ala Lys Arg Glu Glu Ala Glu Ala Glu Ala Pro Lys Phe Val Asn
            85                  90                  95 caa cac ttg tgt ggt tct cac ttg gtt gaa gct ttg tac ttg gtt tgt       452
Gln His Leu Cys Gly Ser His Leu Val Glu Ala Leu Tyr Leu Val Cys
        100                 105                 110 ggt gaa aga ggt ttc ttc tac act gac aag gag tgg aag ggt atc gtt       500
Gly Glu Arg Gly Phe Phe Tyr Thr Asp Lys Glu Trp Lys Gly Ile Val
    115                 120                 125 gaa caa tgt tgt act tct atc tgt tct ttg tac caa ttg gaa aac tac       548
Glu Gln Cys Cys Thr Ser Ile Cys Ser Leu Tyr Gln Leu Glu Asn Tyr
130                 135                 140                 145 tgt aac tagacgcagc ccgcaggctc tagaaactaa gattaatata attata           600
Cys Asn <210> SEQ ID NO 8
<211> LENGTH: 147
<212> TYPE: PRT
<213> ORGANISM: N-terminal extension

<400> SEQUENCE: 8

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45
```

```
Asp Val Ala Val Leu Pro Phe Ser Asn Ser Thr Asn Asn Gly Leu Leu
 50                  55                  60

Phe Ile Asn Thr Thr Ile Ala Ser Ile Ala Ala Lys Glu Glu Gly Val
 65                  70                  75                  80

Ser Met Ala Lys Arg Glu Glu Ala Glu Ala Glu Ala Pro Lys Phe Val
                 85                  90                  95

Asn Gln His Leu Cys Gly Ser His Leu Val Glu Ala Leu Tyr Leu Val
                100                 105                 110

Cys Gly Glu Arg Gly Phe Phe Tyr Thr Asp Lys Glu Trp Lys Gly Ile
                115                 120                 125

Val Glu Gln Cys Cys Thr Ser Ile Cys Ser Leu Tyr Gln Leu Glu Asn
                130                 135                 140

Tyr Cys Asn
145

<210> SEQ ID NO 9
<211> LENGTH: 550
<212> TYPE: DNA
<213> ORGANISM: N-terminal extension
<220> FEATURE:
<221> NAME/KEY: CDS
<222> LOCATION: (115)...(489)

<400> SEQUENCE: 9
ttcttgctta aatctataac tacaaaaaac acatacagga attccattca agaatagttc       60
aaacaagaag attacaaact atcaatttca tacacaatat aaacgattaa aaga atg      117
                                                             Met
                                                              1 aaa ctg aaa act gta aga tct gcg gtc ctt tcg tca ctc ttt gca tct      165
Lys Leu Lys Thr Val Arg Ser Ala Val Leu Ser Ser Leu Phe Ala Ser
          5                  10                  15 cag gtc ctt ggc caa cca att gac gac act gaa tct aac act act tct      213
Gln Val Leu Gly Gln Pro Ile Asp Asp Thr Glu Ser Asn Thr Thr Ser
     20                  25                  30 gtc aac ttg atg gct gac gac act gaa tct aga ttc gct act aac act      261
Val Asn Leu Met Ala Asp Asp Thr Glu Ser Arg Phe Ala Thr Asn Thr
 35                  40                  45 act ttg gct ggt ggt ttg gat gtt gtt aac ttg atc tcc atg gct aag      309
Thr Leu Ala Gly Gly Leu Asp Val Val Asn Leu Ile Ser Met Ala Lys
 50                  55                  60                  65 aga gaa gaa ggt gaa cca aag ttc gtt aac caa cac ttg tgt ggt tcc      357
Arg Glu Glu Gly Glu Pro Lys Phe Val Asn Gln His Leu Cys Gly Ser
                 70                  75                  80 cac ttg gtt gaa gct ttg tac ttg gtt tgt ggt gaa aga ggt ttc ttc      405
His Leu Val Glu Ala Leu Tyr Leu Val Cys Gly Glu Arg Gly Phe Phe
             85                  90                  95 tac act gac aag gaa tgg aag ggt atc gtt gaa caa tgt tgt act tct      453
Tyr Thr Asp Lys Glu Trp Lys Gly Ile Val Glu Gln Cys Cys Thr Ser
            100                 105                 110 atc tgt tct ttg tac caa ttg gaa aac tac tgt aac tagacgcagc            499
Ile Cys Ser Leu Tyr Gln Leu Glu Asn Tyr Cys Asn
        115                 120                 125 ccgcaggctc tagaaactaa gattaatata attatataaa aatattatct t              550

<210> SEQ ID NO 10
<211> LENGTH: 125
<212> TYPE: PRT
<213> ORGANISM: N-terminal extension

<400> SEQUENCE: 10
```

```
Met Lys Leu Lys Thr Val Arg Ser Ala Val Leu Ser Ser Leu Phe Ala
 1               5                  10                  15

Ser Gln Val Leu Gly Gln Pro Ile Asp Asp Thr Glu Ser Asn Thr Thr
            20                  25                  30

Ser Val Asn Leu Met Ala Asp Asp Thr Glu Ser Arg Phe Ala Thr Asn
        35                  40                  45

Thr Thr Leu Ala Gly Gly Leu Asp Val Val Asn Leu Ile Ser Met Ala
    50                  55                  60

Lys Arg Glu Glu Gly Glu Pro Lys Phe Val Asn Gln His Leu Cys Gly
65                  70                  75                  80

Ser His Leu Val Glu Ala Leu Tyr Leu Val Cys Gly Glu Arg Gly Phe
                85                  90                  95

Phe Tyr Thr Asp Lys Glu Trp Lys Gly Ile Val Glu Gln Cys Cys Thr
            100                 105                 110

Ser Ile Cys Ser Leu Tyr Gln Leu Glu Asn Tyr Cys Asn
        115                 120                 125

<210> SEQ ID NO 11
<211> LENGTH: 550
<212> TYPE: DNA
<213> ORGANISM: N-terminal extension
<220> FEATURE:
<221> NAME/KEY: CDS
<222> LOCATION: (115)...(486)

<400> SEQUENCE: 11
ttcttgctta aatctataac tacaaaaaac acatacagga attccattca agaatagttc    60
aaacaagaag attacaaact atcaatttca tacacaatat aaacgattaa aaga atg    117
                                                              Met
                                                                1 aaa ctg aaa act gta aga tct gcg gtc ctt tcg tca ctc ttt gca tct    165
Lys Leu Lys Thr Val Arg Ser Ala Val Leu Ser Ser Leu Phe Ala Ser
        5                  10                  15 cag gtc ctt ggc caa cca att gac gac act gaa tct caa act act tct    213
Gln Val Leu Gly Gln Pro Ile Asp Asp Thr Glu Ser Gln Thr Thr Ser
            20                  25                  30 gtc aac ttg atg gct gac gac act gaa tct gct ttc gct act caa act    261
Val Asn Leu Met Ala Asp Asp Thr Glu Ser Ala Phe Ala Thr Gln Thr
        35                  40                  45 aac tct ggt ggt ttg gat gtt gtt ggt ttg atc tcc atg gct aag aga    309
Asn Ser Gly Gly Leu Asp Val Val Gly Leu Ile Ser Met Ala Lys Arg
    50                  55                  60                  65 gaa gaa ggt gaa cca aag ttc gtt aac caa cac ttg tgc ggt tcc cac    357
Glu Glu Gly Glu Pro Lys Phe Val Asn Gln His Leu Cys Gly Ser His
                70                  75                  80 ttg gtt gaa gct ttg tac ttg gtt tgc ggt gaa aga ggt ttc ttc tac    405
Leu Val Glu Ala Leu Tyr Leu Val Cys Gly Glu Arg Gly Phe Phe Tyr
            85                  90                  95 act gac aag gaa tgg aag ggt atc gtt gaa caa tgc tgt acc tcc atc    453
Thr Asp Lys Glu Trp Lys Gly Ile Val Glu Gln Cys Cys Thr Ser Ile
        100                 105                 110 tgc tcc ttg tac caa ttg gaa aac tac tgc aac tagacgcagc ccgcaggctc    506
Cys Ser Leu Tyr Gln Leu Glu Asn Tyr Cys Asn
    115                 120 tagaaactaa gattaatata attatataaa aatattatct tctt    550

<210> SEQ ID NO 12
<211> LENGTH: 124
```

```
<212> TYPE: PRT
<213> ORGANISM: N-terminal extension

<400> SEQUENCE: 12

Met Lys Leu Lys Thr Val Arg Ser Ala Val Leu Ser Ser Leu Phe Ala
 1               5                  10                  15

Ser Gln Val Leu Gly Gln Pro Ile Asp Asp Thr Glu Ser Gln Thr Thr
            20                  25                  30

Ser Val Asn Leu Met Ala Asp Asp Thr Glu Ser Ala Phe Ala Thr Gln
        35                  40                  45

Thr Asn Ser Gly Gly Leu Asp Val Val Gly Leu Ile Ser Met Ala Lys
    50                  55                  60

Arg Glu Glu Gly Glu Pro Lys Phe Val Asn Gln His Leu Cys Gly Ser
65                  70                  75                  80

His Leu Val Glu Ala Leu Tyr Leu Val Cys Gly Glu Arg Gly Phe Phe
                85                  90                  95

Tyr Thr Asp Lys Glu Trp Lys Gly Ile Val Glu Gln Cys Cys Thr Ser
            100                 105                 110

Ile Cys Ser Leu Tyr Gln Leu Glu Asn Tyr Cys Asn
            115                 120

<210> SEQ ID NO 13
<211> LENGTH: 27
<212> TYPE: DNA
<213> ORGANISM: Primer

<400> SEQUENCE: 13
taaatctata actacaaaaa acacata                                         27

<210> SEQ ID NO 14
<211> LENGTH: 107
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(107)
<223> OTHER INFORMATION: n = A,T,C or G
<221> NAME/KEY: misc_feature
<222> LOCATION: (1)...(107)
<223> OTHER INFORMATION: m = C or A

<400> SEQUENCE: 14
cttagtttct agactagtta cagtagtttt ccaattggta caaagaacag atagaagtac     60
aacattgttc aacgataccc ttccamnnct tgtcagtgta ggaaacc                  107

<210> SEQ ID NO 15
<211> LENGTH: 4
<212> TYPE: PRT
<213> ORGANISM: N-terminal  extension

<400> SEQUENCE: 15

Glu Glu Phe Lys
 1

<210> SEQ ID NO 16
<211> LENGTH: 45
<212> TYPE: PRT
<213> ORGANISM: Artificial Sequence
<220> FEATURE:
<223> OTHER INFORMATION: Synthetic

<400> SEQUENCE: 16
```

-continued

```
Gln Pro Ile Asp Asp Thr Glu Ser Asn Thr Thr Ser Val Asn Leu Met
1               5                   10                  15

Ala Asp Asp Thr Glu Ser Arg Phe Ala Thr Asn Thr Thr Leu Ala Gly
            20                  25                  30

Gly Leu Asp Val Val Asn Leu Ile Ser Met Ala Lys Arg
        35                  40                  45

<210> SEQ ID NO 17
<211> LENGTH: 6
<212> TYPE: PRT
<213> ORGANISM: N-terminal extension

<400> SEQUENCE: 17

Glu Glu Gly Glu Pro Lys
1               5

<210> SEQ ID NO 18
<211> LENGTH: 44
<212> TYPE: PRT
<213> ORGANISM: Artificial Sequence
<220> FEATURE:
<223> OTHER INFORMATION: Synthetic

<400> SEQUENCE: 18

Gln Pro Ile Asp Asp Thr Glu Ser Gln Thr Thr Ser Val Asn Leu Met
1               5                   10                  15

Ala Asp Asp Thr Glu Ser Ala Phe Ala Thr Gln Thr Asn Ser Gly Gly
            20                  25                  30

Leu Asp Val Val Gly Leu Ile Ser Met Ala Lys Arg
        35                  40
```